US006689368B1

(12) United States Patent
Leroux-Roels et al.

(10) Patent No.: US 6,689,368 B1
(45) Date of Patent: Feb. 10, 2004

(54) IMMUNODOMINANT HUMAN T-CELL EPITOPES OF HEPATITIS C VIRUS

(75) Inventors: Geert Leroux-Roels, Ghent (BE); Robert Deleys, Grimbergen (BE); Geert Maertens, Brugge (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 08/974,685

(22) Filed: Nov. 19, 1997

Related U.S. Application Data

(62) Division of application No. 08/635,886, filed as application No. PCT/EP94/03555 on Oct. 28, 1994.

(30) Foreign Application Priority Data

Nov. 4, 1993 (EP) .............................................. 93402718
Oct. 28, 1994 (WO) ................................. PCTEP9403555

(51) Int. Cl.$^7$ .......................... A61K 39/29; A61K 39/12
(52) U.S. Cl. ............................... 424/228.1; 424/185.1; 424/186.1; 424/189.1; 424/192.1; 424/204.1; 530/300; 530/328; 530/350; 530/806; 530/826; 435/5
(58) Field of Search ................................ 530/300, 350, 530/328, 806, 826; 424/228.1, 185.1, 186.1, 189.1, 192.1, 204.1; 435/5

(56) References Cited

U.S. PATENT DOCUMENTS

| | | | |
|---|---|---|---|
| 5,350,671 A | | 9/1994 | Houghton et al. |
| 5,428,145 A | | 6/1995 | Okamoto |
| 5,639,594 A | * | 6/1997 | Wang et al. ..................... 435/5 |
| 5,709,995 A | * | 1/1998 | Chisari et al. |
| 5,747,239 A | * | 5/1998 | Wang et al. ..................... 435/5 |
| 5,747,339 A | * | 5/1998 | Okayama et al. ............ 435/350 |
| 5,756,666 A | * | 5/1998 | Takiguchi et al. ........ 424/184.1 |
| 5,847,101 A | * | 12/1998 | Okayama et al. ......... 536/23.72 |
| 6,027,729 A | * | 2/2000 | Houghton et al. |

FOREIGN PATENT DOCUMENTS

| | | |
|---|---|---|
| EP | 0 468 527 A2 | 1/1992 |
| EP | 0 468 657 A2 | 1/1992 |
| EP | 0 485 209 A1 | 5/1992 |
| EP | 0 759 937 | 3/1997 |
| WO | WO 92/22571 | 12/1992 |
| WO | WO 9300365 | 1/1993 |
| WO | 9300365 | 1/1993 |
| WO | WO 93/06126 | 4/1993 |
| WO | 93-06247 * | 4/1993 |
| WO | WO 93/15207 | 8/1993 |
| WO | WO 93/18054 | 9/1993 |

OTHER PUBLICATIONS

Janeway et al, Immunology, pp. 8.2, 8.3 (copyright 1994) Current Biology Ltd./Garland Publishing.
Koziel et al, Journal of Immunology, 149, 3339–3344 (1992).
Virus Research, vol 30, No. 1, Oct. 1993, Amsterdam, NL, pp27–41, Lin H.J. et al 'The Hepatitis C Virus Genome: a guide to its conserved Sequences and Candidate Epitopes' see p 22, line 25–line 26 table 3.
Gastroenterology, vol 104, No. 4PT2, Apr. 1993, pA660, Journal of Virology, vol 67, No. 12, 1993, pp7522–7532.
Jornal of Medical Virology, Vol 40, no2, Jun. 1993 NY, NY, pp150–156, Lesniewski et al Hypervariable 5'–Terminus of Hepatitis C Virus E2/NS1 Encodes Antigenically Distinct Variants.
Proceedings of the National Academy of Sciences USA, Vol 89, Apr. 1992, Washington, D.C., pp3468–3472, Weiner et al, Evidence For Immune Selection of Hepatitis C Virus (HCV) Putative et al.
Kozie et al Hepatitis C Virus 9HCV)–specific cytotoxic T lymphocytes recognize et al.
Roitt et al, "Immunology", pp. 8.3, 8.4 (copyright 1985), Gower Medical Publishing, London, England.
Roitt et al, "Immunology", pp. 7.6, 7.7 (copyright 1989), Gower Medical Publishing, London, England.
Farci et al 1992 Science 258 p 135–140.
Falk et al 1991 Nature 351 p 290–296.
Janeway et al, "Immunology", pp. 8.2, 8.3 (copyright 1994), Current Biology Ltd./Garland Publishing.
Koziel et al, Journal of Immunology, 149, 3339–3344 (1992).
Lin et al. "The Hepatitis C Virus Genome: a Guide to its Conserved Sequences and Candidate Epitopes", Virus Research, 30 (1993) 27–41.
Stuyver et al., "Analysis of the Putative $E^1$ Envelope and NS4a Epitope Regions of HCV Type $3^{1}$", Biochemical and Biophysical Research Communications, vol. 192, No. 2, 1993, pp 635–641.
Falk et al "Consensus Motifs and Peptide Ligands of MHC Class I Molecules", Seminars in Immunology, vol. 5, 1993:pp 81–94.
Roitt et al, "Immunology", pp. 7.6, 7.7 (copyright 1989), Gower Medical Publishing, London, England.
Roitt et al, "Immunology", pp. 8.3, 8.4 (copyright 1985), Gower Medical Publishing, London, England.
Alignment of Okayama et al. with SEQ ID NO:57.*
Farci et al. 1992 Science 258 p 135–140.*
Falk et al. 1991 Nature 351 p 290–296.*

* cited by examiner

*Primary Examiner*—Mary K. Zeman
(74) *Attorney, Agent, or Firm*—Nixon & Vanderhye, P.C.

(57) ABSTRACT

The present invention relates to a polypeptide of about 8 to about 100 amino acids comprising or consisting of at least 8 contiguous amino acids selected from the core, and/or the NS3 regions of the HCV polyprotein, with said contiguous amino acids containing a T-cell stimulating epitope.

66 Claims, 31 Drawing Sheets

FIGURE 1. Evolution of lymphoproliferative responses and transaminase activities in HCV patient #632

BE8309 NS3 SEQUENCE

GVAKAVDFVPVESMETTMRSPVFTDNSSPPAVPQTFQVAHLHAPTGSGKSTKVPAAYAA
QGYKVLVLNPSVAATLGFGAYMSKAHGVDPNIRTGVRTITTGAPITYSTYGKFLADGGC
SGGAYDIIICDECHSIDSTSILGIGTVLDQAETAGARLVVLATATPPGSVTVPHPNIEE
VALSSTGEIPFYGKAIPIEVIKGGRHLIFCHSKKKCDELAAKLSGFGINAVAYYRGLDV
SVIPTSGDVVVVATDALMTGFTGDFDSVIDCNTCVTQTVDFS

FIGURE 3

```
                1                                                 50
HCV-H     1a    MSTNPKPQRKTKRNTNRRPQDVKFPGGGQIVGGVYLLPRRGPRLGVRATR
HCV-1     1a    --------------------------------------------------
HC-J1     1a    ---I----------------------------------------------
HCVEC1    1a    --------------------------------------------------
HCVHCT18  1a    --------------------------------------------------
HCVHCT23  1a    --------------------------------------------------
HCVHCT27  1a    --------------------------------------------------
HCVTH     1a    --------------------------------------------------
HCV-J     1b    --------------------------------------------------
HC-J4.83  1b    --------------------------------------------------
HC-J4.91  1b    --------------------------------------------------
HCV-China 1b    --------------------------------------------------
HCV-JTA   1b    ----------------Y----------------V-------T--------
HCV-JTB   1b    ----------------Y----------------V-------T--------
HCV-BK    1b    -----------------------------------------------P--
HCV-JK1   1b    --------------------------------------------------
HCV-T     1b    ---G----------------------------------------------
BNL1      1d    --------------------------------------------------
BNL2      1d    --------------------------------------------------
CAM1078   1e    -----------------------------------V-----------A--
FR2       1f    --------------------------------------------------
HC-J6     2a    --------------------------------------------------
HC-J8     2b    --------------------------------------------------
```

FIGURE 4A

|        |    | 1 | | | | | | | | | | | | | | | | | | | | | | | | | | | | | | | | | | | | | | | | | | | | | | | | 50 |
|--------|----|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| CH610  | 2c | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| CH114  | 2c | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| NE92   | 2d | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| BNL3   | 2e | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| FR4    | 2f | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | P | - | - | - |
| HD10   | 3a | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| BR33   | 3a | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| BR36   | 3a | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| N2L1   | 3b | - | - | - | L | - | - | - | - | Q | - | - | - | - | L | - | - | - | - | N | - | - | - | - | - | - | - | - | - | - | - | - | - | - | - | - | - | - | - | - | - | - | - | - | - | - | - | - | V | - | - |
| HCVTR  |    | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | V | - | - |
| GB809-4| 4a | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| GB116  | 4c | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| GB215  | 4c | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| GB358  | 4c | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| GB809  | 4c | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| DK13   | 4d | - | - | - | - | - | - | - | - | - | - | - | - | - | - | - | - | - | - | - | - | - | - | - | - | - | - | - | - | - | - | - | M | - | - | - | - | - | - | - | - | - | - | - | - | - | - | - | - | - | - |
| CAM600 | 4e | - | - | - | - | - | - | - | - | - | - | - | - | - | - | - | - | - | - | - | - | - | - | - | - | - | - | - | - | - | - | - | M | - | - | - | - | - | - | - | - | - | - | - | - | - | - | - | - | - | - |
| GB809  | 4e | - | - | - | - | - | - | - | - | - | - | - | - | - | - | - | - | - | - | - | L | - | - | - | - | - | - | - | - | - | - | - | M | - | - | - | - | - | - | - | - | - | - | - | - | - | - | - | - | - | - |
| CAMG22 | 4f | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| GB549  | 4g | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| GB438  | 4h | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| CAR4/1205 | 4i | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |
| CAR4/901  | 4? | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - | - |

FIGURE 4B

| | | 51 | | 100 |
|---|---|---|---|---|
| | | KTSERSQPRGRRQPIPKARRPEGRTWAQPGYPWPLYGNEGCGWAGWLLSP | | |
| HCV-H | 1a | ------------------------------------------------- | | |
| HCV-1 | 1a | ------------------------------------------------- | | |
| HC-J1 | 1a | ---------------------V--------------------------- | | |
| HCVEC1 | 1a | ------------------------------------------------- | | |
| HCVHCT18 | 1a | ------------------------------------------------- | | |
| HCVHCT23 | 1a | ------------------------------------------------- | | |
| HCVHCT27 | 1a | ------------------------------------------------- | | |
| HCVTH | 1a | ------------------------------------------------- | | |
| HCV-J | 1b | ------------------------------------------M------ | | |
| HC-J4.83 | 1b | ---W---------------A-----------------------L----- | | |
| HC-J4.91 | 1b | -----------------Q-A-----------------------L----- | | |
| HCV-China | 1b | -------------------------------------------F----- | | |
| HCV-JTA | 1b | -------------------A-----------------------L----- | | |
| HCV-JTB | 1b | -------------------A-----------------------L----- | | |
| HCV-BK | 1b | -------------------A-----------------------L----- | | |
| HCV-JK1 | 1b | -----------------Q-A-----------------------L----- | | |
| HCV-T | 1b | -----------------Q-A-----------------------L---V- | | |
| BNL1 | 1d | -----------------X-S----------------------------- | | |
| BNL2 | 1d | ---------D-------QSD-X---H----------------------- | | |
| CAM1078 | 1e | ------E----------------------------------------- | | |
| FR2 | 1f | -----------------S-------------------A----------- | | |
| HC-J6 | 2a | -----------D--ST-KS-GK----------------------L----- | | |
| HC-J8 | 2b | -----------D--ST-KS-GK--------------------------- | | |

FIGURE 4D

```
         51                                                    100
CH610    ----------------------------D--T-T-KS-GR-------L--------
CH114    ----------------------------D---T-KS-GK-----------------
NE92     ----------------------------D-XAT-S-GR-----L------------
BNL3     ----------------------------D-XAT-S-GR-----L------------
FR4      ----------------------------D-AT-KS-GR-----L------------
HD10     --------------------------------------------------------
BR33     --------------------------------------------------------
BR36     --------------------------------------------------------
NZL1     --------------------------------------------------------
HCVTR    ------------KQ-HL----SR---S--------------K---L----------
GB809_1  --------------------------------------------------------
GB116    --------------------------------------------------------
GB215    --------------------------------------------------------
GB358    --------------------------------------------------------
GB809    --------------------------------------------------------
DK13     ------------QL---S--------------------------------------
CAM600   -------------T---S--------------------------------------
GB809    -------------S---S--------------------------------------
CAMG22   --------------------------------------------------------
GB549    --------------------------------------------------------
GB438    --------------------------------------------------------
CAR4/1205 -------------------------------------------------------
CAR4/901 --------------------------------------------------------
```

FIGURE 4E

```
          51                                                    100
BNL7      --------------------------------------------------
BE95      ------------------------S----S--------------------
BE100     ----------------------Q-T-S-G--------A----L-------
HK2       --------------------------------------------------
FR1       ------------------------Q--Q--H-------------------
VN4       -------------------V-Q-T--S-G---------------------
VN12      ----A--------------V-HQT--------------------------
VN8b      ----A--------------V-QNQ--------------------------
VN9a      -------------------V-HQT--------------------------
NE98      -------S-----------------R----T---S---------X-----
```

FIGURE 4F

| | | 101                                              150 |
|---|---|---|
| HCV-H | 1a | RGSRPSWGPTDPRRRSRNLGKVIDTLTCGFADLMGYIPLVGAPLGGAARA |
| HCV-1 | 1a | ------------------------------------------------- |
| HC-J1 | 1a | ------------------------------------------------- |
| HCVEC1 | 1a | ------------------------------------------------- |
| HCVHCT18 | 1a | ------------------------------------------------- |
| HCVHCT23 | 1a | ---------------------------------------R--------- |
| HCVHCT27 | 1a | ------------------------------------------------- |
| HCVTH | 1a | ------------------------------------------------- |
| HCV-J | 1b | ------------------------------------------------- |
| HC-J4.83 | 1b | ------------------------------------------------- |
| HC-J4.91 | 1b | ------------------------------------------------- |
| HCV-China | 1b | ------------------------------------------------- |
| HCV-JTA | 1b | ------------------------------------------------- |
| HCV-JTB | 1b | ------------------------------------------------- |
| HCV-BK | 1b | ------------------------------------------------- |
| HCV-JK1 | 1b | Y---R--------------------------------------V----- |
| HCV-T | 1b | ----N--------------------------------------------- |
| BNL1 | 1d | ----N--------------------------------------------- |
| BNL2 | 1d | ----N--------------------------------------------- |
| CAM1078 | 1e | ------------------------------------------------- |
| FR2 | 1f | -------N--------------------------------------S-T |
| HC-J6 | 2a | -------N----H---V-----------------------V---V---- |
| HC-J8 | 2b | ----T---H-------R----I------------------V---V---- |

FIGURE 4G

| | | 101 | | | | | | 150 |
|---|---|---|---|---|---|---|---|---|
| CH610 | 2c | ---------- | ---------- | ---------- | ----H----- | ---------- | ---------- | ---------- |
| CH114 | 2c | ---------- | ---------- | ---X------ | ---------- | ---------- | -V-------- | ----V--V-- |
| NE92 | 2d | ---------- | ---------- | ---------- | ----H----- | ---------- | -V-------- | --X-V----- |
| BNL3 | 2e | ---------- | ---------- | ---------- | -N---H---- | /SEQ ID NO:285 | -V-------- | ----V--V-- |
| FR4 | 2f | ---------- | ---------- | --XX------ | ---X------ | ---X------ | -V-------- | --X-V--X-- |
| HD10 | 3a | ---------- | ---------- | ---X------ | ---------- | ---------- | ---------- | -V--V----- |
| BR33 | 3a | ---------- | ---------- | ---------- | ---------- | ---------- | -V-------- | ----V--V-- |
| BR36 | 3a | ---------- | ---------- | ---------- | ---------- | ---------- | -V-------- | ----V--V-- |
| NZL1 | 3a | ---------- | ---N------ | ---------- | ---------- | ---------- | -V-------- | ----V--V-- |
| HCVTR | 3b | ---------- | ---N------ | ---------- | -----F---- | ---------- | -V-------- | ----V--V-- |
| GB809_4 | 4a | ---------- | ---------- | ---------- | ---------- | ---------- | -V-------- | ----V--V-- |
| GB116 | 4c | ---------- | ---------- | ---------- | ---------- | ---------- | -V-------- | ----V--V-- |
| GB215 | 4c | ---------- | ---------- | ---------- | ---------- | ---------- | -V-------- | ----V--V-- |
| GB358 | 4c | ---------- | ---------- | ---------- | ---------- | ---------- | -V-------- | ----V--V-- |
| GB809 | 4c | ---------- | ---N------ | ---------- | ---------- | ---------- | ---------- | ----V--V-- |
| DK13 | 4d | ---------- | ---N------ | ---------- | ---------- | ---------- | -V-------- | ----V--V-- |
| CAM600 | 4e | --X-X----- | -N---X---- | ---------- | ---------- | ---------- | ---------- | ----V--V-- |
| GB809 | 4e | ---------- | ---N------ | ---------- | ---------- | ---------- | ---------- | ----V--V-- |
| CAMG22 | 4f | ---------- | ---------- | ---------- | ---------- | ---------- | ---------- | ----V--V-- |
| GB549 | 4g | ---------- | ---------- | ---------- | ---------- | ---------- | ---------- | ----V--V-- |
| GB438 | 4h | ---------- | ---------- | ---------- | ---------- | ---------- | ---------- | ----V--V-- |
| CAR4/1205 | 4i | ---------- | ---------- | A--------- | ---------- | ---------- | ---------- | -V--V--X-- |
| CAR4/901 | 4? | ---------- | ---------- | ---------- | ---------- | ---------- | ---------- | -V--V----- |

FIGURE 4H

```
                101                                                  150
BNL7     4k     ------------N-------------------------------------
BE95     5a     ----N-----N---K-----------------------G-I--V-----
BE100    5a     ---------------------V----------------G-V--V-----
HK2      6a     ---H--N-------------------------V-----V--A-------
FR1      7a     ---N--N-------------XXL---------V--VL-G----V-A---
VN4      8a     ---N--N-----------------------V-------V---V-X----
VN12     8b     ---D-X-N---X-----------E--V-----------V---V-AE---
VN13     9a     X----N----N---X----------------------XX---IE----
NE98     10a    -----------------------------N-------------------
```

FIGURE 4I

```
              151                                            200
              LAHGVRVLEDGVNYATGNLPGCSFSIFLLALLSCLTVPASAYQVRNSTGL
HCV-1    1a   -------------------------------------------------
HCV-H    1a   --------------------------------------------S----
HC-J1    1a   -------------------------------------------------
HCVEC1   1a   --------------------------------------------S----
HCVHCT18 1a   --------------------------H----------------------
HCVHCT23 1a   -------------------------------------------------
HCVHCT27 1a   --------------------------------------------S-I--
HCVTH    1a   -------------------L-----------------------------
HCV-J    1b   -------------------------------------I---E---VS-I
HC-J4.83 1b   -------------------------------------I---E---VS-I
HC-J4.91 1b   -------------------------------------I---E---VS-I
HCV-China1b   -------------------------------------T---E---VS-I
HCV-JTA  1b   -------------------------------------I---AS-----
HCV-JTB  1b   -------------------------------------I---RS-----
HCV-BK   1b   -------------------------------------T---E-H-VS-I
HCV-JK1  1b   -----------------------------------V-T-E---VS-V
HCV-T    1b   -------------------------------------I---E-H-VS-I
BNL1     1d   ------------------------------------XT-HE--AS-V
BNL2     1d   ------------------------F-----------TT-HE--AS-V
FR2      1f   -X-------XG--XXXXX--X---XX-------T---E-HST-DG
HC-J6    2a   --------------F---------------I-T-V--AE-K-ISTG
HC-J8    2b   ----------------I-----------------V--V--VE---ISSS
CH610    2c   ----------------I----------S-----IS--V--VE-K-TSTS
```

```
                151                                                    200
S83      2c     ---------------------------------------------------VE-KDTGDS
CH114    2c     ------IX-----------------M-----------------XIS--V--XE---TST-
NE92     2d     ------I--------------------------------------I---V-GL--K-TSSS
BNL3     2e     --X---I--X---------------X-----------------------V--XVE-K-TSQA
FR4      2f     ------I------------------------------------------V---I--K-NSHF
BNL4     2g     ------I------------------------------------------V---V--K-TSTM
BNL5     2h     ------I------------------------------------------V---V--K-TSHS
BNL6     2i     ------I------------------------------------I-----V---V--A-RS-S
HD10     3a     ---A--I-F--------------------------------F--IH--ASLEW--TS-
BR33     3a     ---A--I-F--------------------------------F--IH--AGLEW--TS-
BR36     3a     ---A--I-F--------------------------------F--IH--ASLEW--TS-
NZL1     3a     ---A--I-F--------------------------------F--IH--ASLEW--TS-
HCV-TR   3b     ---A-G--I--------------------------------F---C---GLEYT-TS-
GB809_4  4a     ----AV--I------------------------------------------EHY--AS-I
Z4       4a     ---------------------------------------------------EHY--AS-I
Z1       4b     ---------------------------------------------------VHY--AS-V
GB116    4c     -E----AV--I--------------S-------------------T---VNY--AS-V
GB215    4c     -E----AV--I--------------Y-------------------T---IHY--AS-V
GB358    4c     ------AV--I----------------------------------T---VNY--AS-I
Z6       4c     ---------------------------------------------------VNY--AS-V
Z7       4c     ---------------------------------------------------VNYH-AS-V
DK13     4d     ------L----------------------------------------------NY---S-V
CAM600   4e     ------AV--I----------------------------------T---VNY--AS-I
```

```
           151                                                  200
GB809      ----AV------I---------------------------GVNY--AS-V
CAMG22     ----AV------I---------------------------VHYH-TS-I
CAMG27     ----AV------I---------------------------VHYH-TS-I
GB549      ----AV------I---------------------------QHY--IS-I
GB438      ----AV------I-------------V--R----------QHY--AS-I
CAR4/12054i ----A-------I---------S-----------------IHY--ASDG
CAR4/901   4? ---AV------I-------X--------------------QHY--VS-I
BNL7          --I-F-------------------------------INY--VS-I
BNL8          --I---------------------------------INY--TS-I
BNL9          --I---------------------------------INYH-TS-I
BNL10         --I------I--X---------------------------TNY--VS-I
BNL11         --I-----X---------------------------TNY--VS-I
BNL12         --I---------------I---------------------QHY--VS-I
GB724      4?
BE95       5a ------------I-----------------------VPY--AS-I
BE100      5a ------------I-----------------------VPY--AS-I
SA4        5a ------------------------------------VPY--AS-V
HK2        6a ---AI------I----------------------T-LTYG--S--
FR1        7a ---AI-----------------------------T-I--K-AS-I
VN4        8a -XXI--X--X--XX-X---------X--------T-AHYT-KS--
VN12       8b ---AI------I----------------------T-LNYA-KS--
NE98       10a -X---------I--F-----------F--LT-TAGLEY--AS--
```

```
        201                                               250
S83     -MP------S-------------WQLEG-V-------------E-TA-V------PVA-NL-ISQ
CH114   -M-------S-------------WQLEG-VX-I----------EWTNTTP-----PVS-X--I-Q
NE92    -M-------Q-------------WQLR---V--V---------EEK--I-----IPVS-NI-VSQ
BNL3    -MA------S--N----------WQLX---V--V---------ENSSGRFH---IPIS-NI-VSK
FR4     -MA------A-D-----------WQLR---V--V---------E-S--RTF---T-VS-N--VSR
BNL4    -MA------S--N-----IWQMQG-V--V--------------ELQ--K----IPV--N--VNQ
BNL5    -M-------S-------------WQLK---V--V---------E-HQ-Q----IPV--N--VSQ
BNL6    -M-------S-------------WQLEE-V--V----------EWKD-T----IPV--NI-VSQ
BNL6    -VL------S----------------D-V--------------QD--T-A--TPV----V-Y
HD10    -VL------S----------------D-V-----A--------QD--T-T--TPV----V-Y
BR33    -VL------S----------------D-V--------------QD--T-T--TPV----V-Y
BR36    -VL------S----------------D-V----I---------QD--T-T--TPV----VKY
NZL1    -VL------S-G--------------E-V----L---------TT--Q-S--TPV----V-Y
HCV-TR  ---I------------------V---TDHH--L----------A--V-----TVSST--V-T
GB809-4 ---I--------------------DHH---L------------MT--T----TPV----AVS
Z4      ---I--------T---------TEHH-M-L-------------TE--T----TPV----VAH
Z1      ---I--------------------DYH---L--L---------V--Q------PL----APY
GB116   ---I--------------------DHH---L--L---------V--Q------L-----APY
GB215   ---I--------------------TEHH--L--L---------V--Q------LS----APY
GB358   ---I--------------------EHQ---L--L---------V--Q------L-----APY
Z6      ---I------M-------------EHH---L--L------------Q------L-----VSY
Z7      ---I--------------------TDYH--L------------Q----------L-----APY
DK13    ---I--------------------TDYH--L------------K.T---SL-------AQH
CAM600  ---I--------A---------TENH---L-------------T--Q------L-----SPY
```

FIGURE 4N

```
              201                                              250
GB809         --I-----A-------TDNH---L-------------KT--Q----L----SPY
CAMG22        --L-------------VHH---L---------------T--Q----L--L-API
CAMG27        --I-----F-------EHH---L---------------T--Q--I-L--L-APH
GB549         ----------------DHH-M-L---------------T--T---PL-----APY
GB438         ----------------DHH-M-L---------------T--V---IPL-----VPY
CAR4/12054i   -YI-------------ENH---L----I---------KT--Q----L--L-APH
CAR4/901 4?   ----------------DHH-M-L----I----------T--V---SL-----APY
BNL7          -Y--------------DHH---L---------------T--Q----L-----APY
BNL8          ----------------DHH---L---------------T--Q----L-----APY
BNL9          ----------------DHH---L----------------V--Q-S--L--I-APY
BNL10         --I-------------DHH-AL-----------------V--Q----L-----APY
BNL11         --------F-------DHH---L----------------K--H----L-----APY
BNL12         ----------------SDHH--L---------------KT--T----L-----API
GB724         --I-------------TDHH--L---------------T--V---TPV-----AVS
4?            --------V-------DNL---A---------------MT--V---QI----LSAPS
BE95          ----------------D-L---A---------------KD-V---QI----LSAPS
BE100         ----------------DNL---A---------------QD-V-K--QI----LSAPN
SA4           ----------------DAM---L---L-----------VDDR-T--H-V---L-IPN
HK2           --L-------------DAM---L-----------------IKA--E----LPVS--L-VPN
FR1           --L-----S-N-----ETM---L-----------------KXX--Q----QAS--L-VPN
VN4           --L-------------ETL---L-----------------KT--LTK--LSAS--L-VQN
VN12          --L-------------NGM---L-----------------LTK--LSAS--L-VQN
NE98          -M----S-G-------G-I---L------------------S-T-----IPVSX---VKS
```

FIGURE 40

```
          251                                              300
HCV-1     1a  GKLPATQLRRHIDLLVGSATLCSALYVGDLCGSVFLVGQLFTFSPRRHWT
HCV-H     1a  ----T-------------------------------------------H-
HC-J1     1a  ----T---------------------I-----------------------
HCVEC1    1a  ---T----------------------------------------------
HCVHCT18  1a  ----T---------------------I-----------------------
HCVHCT23  1a  ---T----------------------------------------------
HCVHCT27  1a  N----------------I--------------------------------
HCVTH     1a  R--T-------------I--------------------------------
HCV-J     1b  SSI-T-TI---V--------A-A---M-----------------S---YE-
HC-J4.83  1b  ASV-T-TI---V--------A-AF--M---------------------E-
HC-J4.91  1b  ASV-T-TI---V--------T-AF--M-----I---------------E-
HCV-China1b 1b ATI-TATV---V--------A-AFS-M---------------------YE-
HCV-JTA   1b  TSI-T-TI---V--------A-AF--M---------------------YE-
HCV-JTB   1b  TSI-T-TI---V--------A-AF--M---------------------YE-
HCV-BK    1b  VTI-T-TI---V--------A-AF--M-----------------V---V-
HCV-JK1   1b  SSI-T-TI---V--------A-A---M---------------------YE-
HCV-T     1b  NSV-TATI---V--------A-AF--M---------------------YE-
BNL1      1d  ASV-TXAI---V--------XX-F--M--X----------A-------V-
BNL2      1d  ANV-TAAI---V--------T-AFR-M---------------------M-H-
FR2       1f  ANA-IDEV---V--------A-VF--M--I-------G--------LYH-
HC-J6     2a  PGALTQG--T---MV-M-----------------------TS-------
HC-J8     2b  RGALTRS-T-V-MI-MA--A-------------V--A-MILS-A-MV--Q--NF
CH610     2c  PGTLTKG--A-V-VI-M---------------V--ALMIAA-AVIA---Q---TF
```

FIGURE 4P

```
                251                                                      300
S83      2c     PGALTKG--A----II-M---V------------V--ALM-AA-VVVV--QH-TF
CH114    2c     PGALTKG--A---VI-M--------------------V--ALMIAA-AVVA--Q--XF
NE92     2d     PGALTKG--T---TIIA---F---I------------------A-M
BNL3     2e     PGALTRG--AR--AV-M--------------------V--A-MIAA-A-IVA-K--YF
FR4      2f     PGALTRG--A---TI-M--------------------------A-M
BNL4     2g     PGALTRG--T---TI-MV-------H-----------V---A-MIAA-VAVV--QY-TF
BNL5     2h     PGALTRG--T---TI-A----V---------------V---A-MIAA-VVIV--QH-NF
BNL6     2i     PGAXTKG--T---II-A---F----------------F--A-M--S-F-MI--QH-IF
HD10     3a     VGATTASI----V-M------A--M-----------M--A-----------A---R-----Q-
BR33     3a     VGATTASI--S-V--------A--M-----------M--A-----------A---R-----Q-
BR36     3a     VGATTASI--S-V--------A--M-----------M--A-----------A---R-----Q-
NZL1     3a     VGATTASI--S-V--------A--M-----------M--A-----------A---R-----Q-
HCV-TR   3b     LGVTTASI--T-V--M---ARQ--------------AF-A-----------A---R-----T-
GB809_4  4a     MDA-LESF----V--M----A---V---V-------------GA----M-----Q------
Z4       4a     PGA-LESF----V--M---A--M----------------GA---M--MI---R------
Z1       4b     PNA-LESM----V--M----A--M----F-I---------G---------D-R------
GB116    4c     VGA-LES---S-V--M----A--V----------H-----G---------M-S-Q------
GB215    4c     IGA-VESF----V-MM---A--V---------I-------G---------M-S-R------
GB358    4c     IGA-LES---S-V--M----A--A---------I------G---------M-S-R------
Z6       4c     IGA-LDS----V--M----A--V---------I-------GA--------M-S-Q------
Z7       4c     IGA-LESI----V--M----A--V---------I------G---------M-S-Q------
DK13     4d     LNA-LES-----V--M---G-------------I---V----G---------Q-------
CAM600   4e     AGA-LEP-----V--M----A--M---------I------GL--------M-----Q-
```

FIGURE 4Q

```
          251                                           300
GB809     4e   VGA-LEP----V--M--A--V-----------GL---M----Q---
CAMG22    4f   LGA-LESM---V--M--T-------------GI---A--M--R--L-
CAMG27    4f   IGA-LESM---V--M--T-------I-----GI----M--N-R--L-
GB549     4g   VGA-LESM---V--M--A--V----I-----G-----M----R---
GB438     4h   LGA-L-SV-Q-V--M--A-------I--H--G---A--MVS-Q---
CAR4/12054i 4? LRA-LSS---A-V--M--A--A---F-----G---A----IR--I-E-
CAR4/901  4?   LGA-L-S----V--M--A-------------G-----M----Q---
BNL7      4k   IGA-LES---S-V--M--A--V---I--X-XGL---M--S-R---
BNL8      4k   IGA-LES---S-V--M--A--V---I-----GL---M--S-R---
BNL9      4k   IGA-LES---S-V--M--A------I-----GA---M--S-R---
BNL10     4k   TAA-LES---S-V--M--A--V---I-----GL---M--SXQ---
BNL11     4k   IGA-LES---S-V-VM--A--V---I-X---GL---M--S-R---
BNL12     4l   LSA-LMSV---V--M--A---S---------GA---M----Q---
GB724     4?   VDA-LESF---V--M--A----V--------GA---M----Q---
BE95      5a   LGAVTAP---AV-Y-A-G-A-----------A-AL--M--YR--Q-A-
BE100     5a   FGAVTAP---AV-Y---G-A-----------A-AL--M--YR--Q-A-
SA4       5a   LGAVTAP---AV-Y-A-G-A-----------A-A---M--YR--Q-T-
HK2       6a   AST---GF----V---A-A-VV---S-I----L-A---M----Q---
FR1       7a   SSV-IHGF----V----A-AF---M-I----II----R-KY-QV
VN4       8a   AST-V-GF-K-V-IM--A-AF---M------GL------LR--M-QV
VN12      8b   ASVSIRGV-E-V------A-AF---M-----GL------R--MYEI
NE98      10a  PCAATAS--T-V-MM-XA-------------AL-X--G-SWRH-Q---
```

FIGURE 4R

```
        301                                            350
        TQGCNCSIYPGHITGHRMAWDMMMNWSPTTALVMAQLLRIPQAILDMIAG
HCV-1      1a  --D---------------N--------A----M-----
HCV-H      1a  --D-----------------------V-----------
HC-J1      1a  ------------------------A-------------
HCVEC1     1a  --------------------------------------
HCVHCT18   1a  --D-----------------------------------
HCVHCT23   1a  --D-----------------------------------
HCVHCT27   1a  --D-----------------------------------
HCVTH      1a  --------------------------------------
HCV-J      1b  V-D-------VS----------------VS----VV--V-
HC-J4.83   1b  V-D-------LS----------------VS----VV--V-
HC-J4.91   1b  V-D-------VS----------------VS----VV--V-
HCV-China1b 1b I------V--------------------VS----VM--VV
HCV-JTA    1b  V-D-------VS----------------VS----VV--V-
HCV-JTB    1b  V-D-------VS----------------VS----VV--V-
HCV-BK     1b  L-D-------VS----------------VS----VV--V-
HCV-JK1    1b  V-D----L--VS----------------VS----VV--VV
HCV-T      1b  V-D-------V-----------------VS----VV--VG-
BNL1       1d  --E-----------------------------------
BNL2       1d  --E-----------------------------------
FR2        1f  V-D----S------XXX---------------------
HC-J6      2a  V-D------T----------------ATMIL-YAM-V-EV-I-I-G-
HC-J8      2b  --E---Q---------------LS---LTMIL-YAA-V-ELV-EI-F-
CH610      2c  V-E---------X-----------------VV--VG-
```

FIGURE 4S

|       |     | 301         319 |
|-------|-----|-----------------|
| S83   | 2c  | V-E---------R----- |
| CH114 | 2c  | V-E------------–X |
| NE92  | 2d  | V-D-------------- |
| BNL3  | 2e  | V-E-------------- |
| FR4   | 2f  | V-E------------–X |
| BNL4  | 2g  | S-D-------------- |
| BNL5  | 2h  | V-D-------------- |
| BNL6  | 2i  | ----------------- |
| HD10  | 3a  | V-T----L---LS---- |
| BR33  | 3a  | V-T----L---LS---- |
| BR36  | 3a  | V-T----L---LS---- |
| NZL1  | 3a  | V-T----L---LS---- |
| HCV-TR| 3b  | V-T--------VS---- |
| GB809_4| 4a | ---D----T-------- |
| Z4    | 4a  | ---E----T-------- |
| Z1    | 4b  | ---D-------VS---- |
| GB116 | 4c  | ---D--A--V------- |
| GB215 | 4c  | ---D--A--V----G-- |
| GB358 | 4c  | ---D--A--V------- |
| Z6    | 4c  | ---D--A--V------- |
| Z7    | 4c  | ---D----T-------- |
| DK13  | 4d  | ---D-------------- |
| CAM600| 4e  | ---D----T-------- |

FIGURE 4T

|  | | 301 | 319 |
|---|---|---|---|
| GB809 | 4e | --D--- | ---- |
| G22 | 4f | --E--- | ---- |
| G27 | 4f | --E--- | ---- |
| GB549 | 4g | --D--- | ---- |
| GB438 | 4h | --D--- | ---- |
| CAR4/12054i |  | --D--- | XXXX |
| BNL7 | 4k | --D--- | ---- |
| BNL8 | 4k | A-D--- | ---- |
| BNL9 | 4k | --D--- | ---- |
| BNL10 | 4k | --D--- | ---- |
| BNL11 | 4k | --E--- | ---- |
| BNL12 | 4l | V-D--- | ---- |
| CAR4/901 | 4? | --D--- | ---- |
| GB724 | 4? | --D--- | ---- |
| BE95 | 5a | V-N--- | ---- |
| BE100 | 5a | V-D--- | ---- |
| SA4 | 5a | V-D--- | ---- |
| HK2 | 6a | V-D--- | ---Q-- |
| FR1 | 7a | --D--- | ---- |
| VN4 | 8a | V-E--- | ---- |
| VN12 | 8b | A-D--- | ---- |
| NE98 | 10a | V-D--- | ---- |

FIGURE 4U

```
           351                                                 400
           AHWGVLAGIAYFSMVGNWAKVLVLLLFAGVDA|ETHVTGGSAGHTVSGF
HCV-1    1a --------------------------------|----------------
HCV-H    1a -------------K------------------|------N-R-TA-L
HC-J1    1a --------------------------------|--I-S--Q-ARAM--L
HCVEC1   1a
HCVHCT18 1a
HCVHCT23 1a
HCVHCT27 1a
HCVTH    1a -------L--Y---------------I-M---G|H-----RVASSTQSL
HCV-J    1b -------L--Y---------------I-A---G|--YTS-A-S--T-TL
HC-J4.83 1b -------L--Y---------------I-A---G|A-YTS-V--R-T---
HC-J4.91 1b -------L--YA--------------I-M---G|D-YAS-AQ-RSTL--
HCV-China1b -------L--Y---------------I-M---G|V-YT----QARHTQSV
HCV-JTA  1b -------L--Y---------------I-M---G|V-YT----QARHTQ-V
HCV-JTB  1b -------L--Y-----A---------I-M---G|D-----AQAK-TNRL
HCV-BK   1b -------L--Y---------------I-M---G|T-Y-SV-H-SQ-TRRV
HCV-JK1  1b -------L--Y---------------I-M---G|S-I-S--TVAR-THSL
HCV-T    1b -------L--Y---------------I-M---G|
BNL1     1d -----MF-L------Q-A-----V-I---A----|Q--TV---TA-NARTL
BNL2     1d -----VF-L------Q-A-----V-----V----|.T-YSS-QE--R--A--
FR2      1f
HC-J6    2a G--------------Q-A---IAI----------|
HC-J8    2b
```

```
              401                                            450
              VSLLAPGAKQNVQLINTNGSWHLNSTALNCNDSLNTGWLAGLFYHHKFNSS
HCV-1     1a  -G--T----I---------------I------------E-----Q-----
HCV-H     1a  ---FT----I---------------I------------E---I-Q-----
HC-J1     1a  ---FT----I------------------------------------------
HCVEC1    1a  ----------------------------------------------------
HCVHCT18  1a  ----------------------------------------------------
HCVHCT23  1a  ----------------------------------------------------
HCVHCT27  1a  ----------------------------------------------------
HCVTH     1a  --W-SQ-PS-KI--V-------I-R---------Q--FI-A---A-R--A-
HCV-J     1b  A--FS---S-RI--V-------I-R---------H--F--A---T-R---
HC-J4.83  1b  T--FSS--S-KI--V-------I-R---------H--F--A---T-----
HC-J4.91  1b  T--FT---S-KI----------I-R------------F--A---T-R--A-
HCV-China1b   T--FFTQ-PA-RI---------I-R---------E--FF-A---A-----
HCV-JTA   1b  A--FFT--PA-KI---------I-R---------E--FF-A---A-----
HCV-JTB   1b  A--FFT--PA-KI---------I-R------------FF-A---T-S---
HCV-BK    1b  --MF-S--PS-KI---------I-R---------Q--F--A---T-S---
HCV-JK1   1b  A--FFS--SA-KI--V------I-R---------E-I--FF-A---VK--
HCV-T     1b  A--FTQ--S-KI----------I-R---------Q--F--S---A-R--A-
BNL1      1d  ----------------------------------------------------
BNL2      1d  ----------------------------------------------------
FR2       1f  ----------------------------------------------------
HC-J6     2a  TGMFSL--R-KI----------I-R---------H--F--S---T-S---
HC-J8     2b  AG-FTT----LY----------I-R---------Q--F--S---T-----
```

| | 571 | | |
|---|---|---|---|
| | IGGAGNNT | | LHCPTDCFRKHPDATYSRCGSGP |
| HCV-1 | -------- | | -L------Y-E----------- |
| HCV-H | --V----- | | ---------------------- |
| HC-J1 | --G----- | | ---------E------------ |
| HCV-J | --V----- | | -V-------E---TK------- |
| HC-J4.83 | --V--H-- | | -T-------E---TK------- |
| HC-J4.91 | --V--R-- | | -I-------E---TK------- |
| HCV-CHINA | --V----- | | -T-------E---T-------- |
| HCV-JTA | --V--L-- | | -T-------E---TK------- |
| HCV-JTB | --V--L-- | | -T-------E---TK------- |
| HCV-BK | --V----- | | -T-------E---TK------- |
| HCV-JK1 | -------- | | -T-------E---TK------- |
| HCV-T | --G----- | | -V-------E---TK------- |
| HC-G9 | --S----- | | -L-------------------- |
| HC-J6 | -RADF-ASMD-L | | ---------T---IK------- |
| HC-J8 | -RKDY-S-ID-L | | ----------------LK--A-- |

FIGURE 5A

```
       604
       WITPRCLVDYPYRLWHYPCTINYTIFKIRMYVGGVEH
HCV-1    R-----M-----------------------V-----
HCV-H    ------------------------------V-----
HC-J1    ------------------------------------
HCV-J    --L---M--------------------V-F-V--V-
HC-J4.83 --L------------------------F-FS---V-
HC-J4.91 --L------------------------L-FS---V-
HCV-CHINA --L-----------------------V-FA----V-
HCV-JTA  --L---I--------------------V-F----V-
HCV-JTB  --L---I--------------------V-F----V-
HCV-BK   --L---M--------------------V-F----V-
HCV-JK1  --L---M--------------------F-F----V-
HCV-T    --L---M--------------------V-F----V-
HC-G9    --L-----------------------V-------F-
HC-J6    --L---I-------------------V---------
HC-J8    --L-----------------------V-F-----A-
```

FIGURE 5B

```
              1188        1200
HCV-1         GVAKAVDFIPVEN
HCV-H         -------------
HC-J1         -----------S-
HC3-J         -----------S-
BE8309        --------V--S-
HC-J4.83      -----------S-
HC-J4.91      -----------S-
HCV-CHINA     -----------T-
HCV-JTA       -----------S-
HCV-JTB       -----------S-
HCV-BK        --------V--S-
HCV-JK1       -----------S-
HCV-T         --------V--S-
HC-J6         ----SI-----T-
HC-J8         ----SI-----S-
```

```
              1201                                              1250
HCV-1         LETTMRSPVFTDNSSPPVVPQSFQVAHLHAPTGSGKSTKVPAAYAAQGYK
HCV-H         -----------------A-------------------------K---
HC-J1         -----------------A------------------------------
HCV-J         M----------------A---T--------------------------
BE8309        M----------------A---T--------------------------
HC-J4.83      M----------------A---T--------------------------
HC-J4.91      M----------------A---T--------------------------
HCV-CHINA     M----------------A---T--------------------------
HCV-JTA       M----------------A---T--------------------------
HCV-JTB       M----------------A---T---------------------X---
HCV-BK        M----------------A------------------------------
HCV-JK1       M----------------A---T--------------------------
HCV-T         M----------------A---A--------------------------
HC-J6         -DIVT---T-S---T--A---TY--GY--------------V-------
HC-J8         -DVAT-T-S-S---T--A----Y--GY--------------S----
```

```
              1251                                              1300
HCV-1         VLVLNPSVAATLGFGAYMSKAHGIDPNIRTGVRTITTGSPITYSTYGKFL
HCV-H         -----------------------V--------------------------
HC-J1         --------------------------------------------------
HCV-J         ------------------E---------------G-------C---
BE8309        -----------------------V----------------A---------
HC-J4.83      ---------------P------------------G---------
HC-J4.91      ---------------------------------------------GS---
HCV-CHINA     -----------------------V----------------A---------
HCV-JTA       ---------------------T------------------A---------
HCV-JTB       ---------------------T------------------G---------
HCV-BK        ----------------------------------------A-V-------
HCV-JK1       -----------------------V----S-----------A---------
HCV-T         -----------------------V----------------A---------
HC-J6         -----------------L------N---------V---A-----------
HC-J8         ------------------------N----------V---DS--------I
```

FIGURE 6A

```
              1301                                              1350
HCV-1      ADGGCSGGAYDIIICDECHSTDATSILGIGTVLDQAETAGARLVVLATAT
HCV-H      --A--------------------S-------------------------
HC-J1      -----------------------V-------------------------
HCV-J      ---------------------S-T-------------------------
BE8309     --------------------I-S--------------------------
HC-J4.83   ---------------------S-T-------------------------
HC-J4.91   ---------------------S-T-------------------------
HCV-CHINA  ---------------------S-T-------------------------
HCV-JTA    ---------------------S-T-------------------------
HCV-JTB    ---------------------S-T-------------------------
HCV-BK     ---------------------S-T-------------------------
HCV-JK1    ----------------------S---------------------A---
HCV-T      --------------M------S-T-------------------------
HC-J6      -----A-------------AV-S-T---------------V--T-----
HC-J8      -----AA------------V---T----------------V--------

1351                                              1400
HCV-1      PPGSVTVPHPNIEEVALSTTGEIPFYGKAIPLEVIKGGRHLIFCHSKKKC
HCV-H      -------S-----------------------------------------
HC-J1      ----I----A-------------------A-------------------
HCV-J      ----I------------N------------I-A----------------
BE8309     ------------------S-------------I----------------
HC-J4.83   ----------------IG--NN----------I-A--------------
HC-J4.91   ----------------IG--NN----------I-A--------------
HCV-CHINA  -----------------N--------------I-A-R------------
HCV-JTA    -----------------N---------------A---------------
HCV-JTB    -----------------N--------------I----------------
HCV-BK     -----------------N--------------I-A-R------------
HCV-JK1    ----------------PN--------------T----------------
HCV-T      ----------I---N-----------------I-T--------------
HC-J6      ------T----------GQE-------R----SY---------------
HC-J8      ---T--T--S-------GHE-----------AF----------------

1401                                              1450
HCV-1      DELAAKLVALGINAVAYYRGLDVSVIPTSGDVVVVATDALMTGYTGDFDS
HCV-H      ---------------------------------S-------F-------
HC-J1      ----------V--------------------------------------
HCV-J      -------TG--L-----------------------------F-------
BE8309     -------SGF-------------------------------F-------
HC-J4.83   -------TG--L----------------PI---A-------F-------
HC-J4.91   -------TG--L----------------PI-----------F-------
HCV-CHINA  -------SS--L-----------------S-----------F-------
HCV-JTA    -------SG-------------------------I--------------
HCV-JTB    -------SG----------------------------------------
HCV-BK     -------SG-------------------------I--------------
HCV-JK1    -------S---V-------------------------------------
HCV-T      -------S----H--------------A--N----------F-------
HC-J6      -----A-RGM-L----------------Q------------F-------
HC-J8      -----A-RGM-V----------------Q--------------------
```

FIGURE 6B

```
              1451            1465
HCV-1       VIDCNTCVTQTVDFS
HCV-H       ---------------
HC-J1       ---------------
HCV-J       ---------------
BE8309      ---------------
HC-J4.83    ---------------
HC-J4.91    ---------------
HCV-CHINA   ---------------
HCV-JTA     ---------------
HCV-JTB     ---------------
HCV-BK      ---------------
HCV-JK1     ---------------
HCV-T       ---------------
HC-J6       -----VA---V----
HC-J8       -----VA-S-I----
```

FIGURE 6C

IMMUNODOMINANT HUMAN T-CELL EPITOPES OF HEPATITIS C VIRUS

The present application is a divisional of application Ser. No. 08/635,886, filed Apr. 25, 1996, pending, which is a 371 U.S. national phase of PCT/EP94/03555, filed Oct. 28, 1994, which claims benefit of EP 93402718.6, filed Nov. 4, 1993.

TECHNICAL FIELD OF THE INVENTION

The present invention relates to the production of novel synthetic immunogens related to the hepatitis C virus core, E1, E2 and NS3 regions and to the use thereof in the production of vaccines, therapeutic agents and the like. More specifically, the present invention relates to polypeptide compositions containing HCV core, E1, E2 and NS3 T cell determinants.

BACKGROUND OF THE INVENTION

In the few years since its discovery, Hepatitis C virus (HCV) has been shown to be a major cause of acute and chronic liver disease. HCV is a single-stranded RNA virus with a genome of approximately 9400 nucleotides that consists of a 5' untranslated region (5'UR) of 341 nucleotides which precedes a single large open reading frame encoding a precursor polyprotein of about 3010 amino acids (Kato et al., 1990). The genetic organization of the viral genome is related to that of flavi-and pestiviruses, with the putative structural proteins located in the N-terminal region and a variety of non structural proteins located at the C-terminal end of the polyprotein. The structural proteins are the core protein (C, amino acids 1–191) followed by the putative envelope proteins E1 (amino acids 192–383) and E2/NS1 (amino acids 384–746). The terms E2 and NS1 are often used interchangeably. Another form of E2 is composed of amino acids 384 to 809 and a third form is associated with NS2. The non structural proteins are NS2, NS3, NS4 and NS5, of which at least NS4 and NS5 have been shown to be further processed into NS4A, NS4B, NS5A, and NS5B.

Structural analysis of HCV genomes revealed the existence of different genotypes that have been classified into types and subtypes (Stuyver et al., 1993). The sequence diversities are distributed along the whole genome including the 5' untranslated region. The highest sequence variability has been observed in the NS2 and 3' untranslated regions, and in the putative envelope regions encoding the E1 and E2 proteins. The core, NS3, and certain regions of the NS4 proteins displayed markedly less diversity (Okamoto et al., 1992).

HCV Humoral Response

Soon after the discovery of HCV, immunoassays for the detection of circulating antibodies against HCV proteins became widely available. These tools have led to an explosive increase of the knowledge in the field of the human humoral immune response to HCV in different conditions. Once it was demonstrated that HCV was the major cause of posttransfusional non-A, non-B hepatitis, the search for antibodies to HCV was added to the safety screening panel of blood products. This procedure not only increased the safety of blood transfusions but also enhanced the knowledge of the epidemiology of the virus. The fact that HCV is responsible for a large proportion of chronic hepatic infections in which blood transfusion or parenteral inoculation are excluded remains a major challenge for further epidemiological studies. The widespread use of the assays for the detection of antibodies to HCV has also led to the recognition of the regions with humoral antigenicity of the virus. The relationship between the kinetics and magnitude of the humoral immune response to the different proteins of HCV and the course and outcome of the disease remains to be established.

HCV T Cell Epitopes

The immune response to viral antigens is almost entirely T cell dependent. T cells are required both for antibody production and for some cytotoxic reactions. HCV-encoded proteins are immunogenic not only at the B cell level, but also at the T cell level.

Studies describing the cellular immune response to HCV are scarce. Lin et al. (1993) describe candidate T cell epitopes within absolutely conserved regions of HCV gene obtained by means of a computer search revealing a large number of potential T cell epitopes. It has also been reported that peripheral blood cell monocytes (PBMC) from HCV-infected individuals proliferate in response to HCV recombinant proteins and that peripheral responses to core protein correlate with a benign course of infection (Botarelli et al., 1993). In the liver of patients with chronic HCV infection HCV-specific, HLA class I- restricted cytotoxic T lymphocytes (CTL) have been identified and cloned that recognize epitopes in E1 and NS2 proteins. These investigators have mainly focused on obtaining T cell clones from individual patients, and on the localization of the immunoreactive domain for the single CTL clones. Such studies led to the discovery of the epitope ASRCWVAM (aa 235–242) (SEQ ID NO:167) (in the aminoterminal part of the E1 protein, and of the epitope LMALTLSPYYKRY (aa 826–838) (SEQ ID NO:168) from the NS2 region (Koziel et al., 1992). In patients with chronic HCV hepatitis intrahepatic $CD4^+$ T cells which specifically recognized the NS4 protein of HCV were observed. The clonotype of these T lymphocytes was not detectable in the PBMC from these subjects (Minutello et al., 1993). These studies demonstrate that in patients with HCV hepatitis, HCV-specific T lymphocytes can be isolated from the infected liver and the peripheral blood. Their role in the pathogenesis of the liver damage in HCV hepatitis and their relevance for the clearance or persistence of the virus remains to be established.

Although neutralization of certain viral infections is possible by humoral immunity only, most microbiological agents can only be cleared from the host with the aid of cellular immunity. Even when the neutralizing capacity of circulating antibodies is established in certain infections, T helper cell activity is generally required to allow B cells to produce the required levels of circulating antibodies, for achievement of neutralization and clearance of the infectious agent. However, certain infectious agents can only be neutralized by means of cellular immunity.

In the case of hepatitis C virus, it can be anticipated that T cell immunity may be required for clearance of the virus, since most patients enter into a chronic course of the disease, and since most patients infected with HCV have developed humoral immunity to most of the HCV antigens which can be employed for diagnosis of HCV infection, as described in patent applications no. EP-A-0 318 216, EP-A-0 388 232, EP-A-0 442 394, EP-A-0 484 787, EP-A-0 489 968. However, most of the antibody-positive patients have not been able to clear the virus from the circulation since they remain HCV-PCR positive and, consequently, the detected antibodies have not been protective neither sufficient to neutralize the virus. Possibly, antibodies to other epitopes which are currently not included in HCV diagnostic assays may be capable of neutralizing HCV infection. Such epitopes may be located on the viral membrane proteins E1 and E2, but protection against a wide range of different HCV species may be hampered by the hypervariability of HCV envelope regions.

The aim of the present invention is to provide T cell stimulating polypeptides and peptides derived from the HCV structural and NS3 regions.

Another aim of the present invention is to provide T cell stimulating polypeptides and peptides as defined above for use in the preparation of an HCV immunogenic composition.

Another aim of the present invention is to provide T cell stimulating peptides or polypeptides derived from the core region, the E1 region, the E2 region, or the NS3 region of HCV.

Another aim of the present invention is to provide T cell stimulating peptides or polypeptides from HCV as specified above which contain either T helper cell (CD4$^+$) epitopes and/or CTL (CD8$^+$) epitopes.

Another aim of the present invention is to provide recombinant polypeptides containing the same.

Another aim of the present invention is to provide therapeutic as well as prophylactic compositions comprising the same.

Another aim of the present invention is to provide prophylactic or therapeutic compositions comprising said polypeptides.

Another aim of the present invention is to provide methods for preventing or treating HCV infection based on the same.

DETAILED DESCRIPTION OF THE INVENTION

More particularly, the present invention describes a polypeptide of about 8 to about 100 amino acids comprising or consisting of at least 8 contiguous amino acids selected from the core and/or E1 and/or E2 and/or NS3 regions of the HCV polyprotein, with said contiguous amino acids containing a T-cell stimulating epitope, and provided that said polypeptide is different from any: known T cell epitope containing HCV peptide or polypeptide described from any of the above-mentioned regions. The latter known HCV polypeptides and peptides are described for screening for B cell epitopes. Such polypeptides and peptides are for instance mentioned in EP-A-0 318 216, EP-A-0 388 232, EP-A-0 442 394, EP-A-0 484 787, EP-A-0 489 968, WO 92/22571, Lesniewski et al., 1993; Weiner et al., 1993; etc. The content of these applications is hereby incorporated by reference.

Even more particularly, the present invention relates to the use of polypeptides as described above for the preparation of an HCV immunogenic composition.

The expression "HCV immunogenic composition" refers to the prevention or treatment of HCV infection.

Preferentially said polypeptide is different from RALAHGVRVLEDG, RMAWDMM, PTDCFRKHP, YPYRLWH, GKSTKVP, PSVAAT, IGTVLDQAE, AVAYYR, ASRCWVAM and TGDFDSVID (SEQ ID NOs: 169–178, respectively).

The term "HCV polyprotein" refers to any HCV polyprotein disclosed in the art and is reviewed in Okamoto et al. 1992, such as the type 1a HCV polyprotein of the HC-J1 isolate, such as the HCV polyprotein of the type 2a HC-J6 isolate (Okamoto et al., 1991), the type 2b HC-J8 isolate (Okamoto et al., 1992). According to this definition, any variation already observed within any of the described regions of HCV is to be considered as part of a the definition of HCV polyprotein. For example, numerous types and subtypes are disclosed in Bukh et al., 1993, Bukh et al., 1994, Stuyver et al., 1993a, Stuyver et al., 1993b, Stuyver et al., 1994a, Stuyver et al., 1994c. Moreover, conservative substitutions may be introduced in these HCV polyproteins according to the present invention. The term "conservative substitution" as used herein denotes that one amino acid residue has been replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that antibodies raised to such a polypeptide also immunoreact with the corresponding polypeptide having the unsubstituted amino acid.

The term "antibody" refers to a molecule that is a member of a family of glycosylated proteins called immunoglobulins, which can specifically combine with an antigen.

The word "antigen" has been used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility.

The term "corresponds" in its various grammatical forms as used in relation to peptide sequences means the peptide described plus or minus up to three amino acid residues at either or both of the amino- and carboxy-termini and containing only conservative substitutions in particular amino acid residues along the polypeptide sequence.

"Epitope" refers to that portion of a molecule that is specifically bound by a T cell antigen receptor or an antibody combining site.

The term "immunoreact" in its various forms means binding between an antigen as a ligand and a molecule containing an antibody combining site such as a Fab portion of a whole antibody.

The expression "T-cell stimulating epitope" or T cell epitope according to the present invention refers to an epitope capable of stimulating T-cells. A T-cell stimulating epitope may be selected according to the present invention by monitoring the lymphoproliferative response (as detailed in the Examples section) towards polypeptides containing in their amino acid sequence at least 8 contiguous amino acids derived from the core, and/or the E1, and/or the E2, and/or the NS3 region of any HCV polyprotein. Said lymphoproliferative response may be measured by either a T-helper assay comprising in vitro stimulation of PMBC from patients with hepatitis C infection with varying concentrations of peptides to be tested for T-cell stimulating activity and counting the amount of radiolabelled thymidine uptake. Said lymphoproliferative response may also be measured by means of a CTL assay measuring the lytic activity of cytotoxic cells using $^{51}$Cr release. Proliferation is considered positive when the stimulation index (mean cpm of antigen-stimulated cultures/mean cpm of controle cultures) is more than 1, preferably more than 2, most preferably more than 3. In order to select a T-cell stimulating epitope containing peptide, the results of these lymphoproliferative assays are compared and immunodominant T-cell epitope containing polypeptides or peptides are selected. The results of the lymphoproliferative assays against certain peptides may also be compared between clinical non-responders and responders to Interferon-α treatment. The lymphoproliferative response towards a series of synthetic, overlapping peptides representing the HCV core, E1 and E2/NS1 sequences and a recombinant NS3 protein was monitored in 32 patients with chronic HCV hepatitis as disclosed in the Examples section of the present invention.

Consequently, the present invention represents a selection of immunodominant T cell epitopes from a series of antigens covering the core, E1, E2 and NS3 regions. From the examples section, it is clear that not only peptide pools 2 and 3 and peptides NS1–5*and NS1–7*but also, pools 4, 5, 6 and 9 and NS3, reacted frequently with hepatitis C patients (Table 4) while infrequent reactivity could only be observed in normal controls with the same polypeptides (Table 5). It is obvious from the data presented in Table 4 that large areas of the HCV structural region, such as pool 1 (amino acids 5–72) and pools 7 and 8 (amino acids 427–578) show little reactivity with T cells of infected patients, even with patients with a response to IFN-α treatment. Most strikingly, however, it was found that while the dominant B cell response to hepatitis C in general is located to the core aminoterminus (see also Table 3), the dominant T cell response is directed towards the core carboxyterminal region (see Table 4). In the literature, ample evidence can be found that the core carboxyterminal half contains little or no B cell-reactive epitopes. Based on the present invention, it may be desirable to yet include for instance parts of the core carboxyterminal region (spanning amino acids 73–176) into prophylactic or therapeutic vaccine compositions.

The words "polypeptide" and "peptide" are used interchangeably throughout the specification and designate a linear series of amino acids connected one to the other by peptide bonds between the alpha-amino and carboxy groups of adjacent amino acids. Polypeptides can be a variety of lengths, either in their natural (uncharged) forms or in forms which are salts, and either free of modifications such as glycosylation, side chain oxidation, or phosphorylation or containing these modifications. It is well understod in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acids side chains, such as glycosyl units, lipids, or inorganic ions such as phosphates, as well as modifications relating to chemical conversions of the chains, such as oxidation of sulfhydryl groups. Thus, "polypeptide" or its equivalent terms is intended to include the appropriate amino acid sequence referenced, subject to those of the foregoing modifications which do not destroy its functionality.

The polypeptides of the invention, and particularly the shorter peptides amongst them, can be prepared by classical chemical synthesis. The synthesis can be carried out in homogeneous solution or in solid phase.

For instance, the synthesis technique in homogeneous solution which can be used is the one described by Houben-weyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The polypeptides according to this invention can also be prepared by means of recombinant DNA techniques as documented below.

The polypeptides or peptides according to the present invention may, as specified above, vary in lenght. The peptides according to the invention contain at least 3, preferably at least 4, 5, 6, 7, most preferably however al least 8 contiguous HCV amino acids. Preferred lengths of peptides are 6, 7, 8, 9, 10, or more (for instance 15, 20, 25, 30, etc.) amino acid residues. The polypeptides of the present invention may be up till 150 to 200 amino acids long, but are preferably less than 100 amino acids.

Further contemplated according to the present invention is a polypeptide as defined above, comprising or consisting of at least 8 contiguous amino acids selected from the region comprised between amino acids 73 to 176 in the core region of HCV, between amino acids 192 to 234 and 243 to 392 of the E1 region of HCV, between amino acids 397 and 428 and amino acids 571 to 638 of the E2 region of HCV, or between amino acids 1188 to 1463 of the NS3 region of HCV, and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Even more particularly, the present invention relates to the use of polypeptides as described above for the preparation of an HCV immunogenic composition.

The expression "comprised between amino acids X to Y" includes the amino acid X and the amino acid Y.

The numbering of the HCV polyprotein used in the present invention refers to the numbering as used for the HCV-J isolate according to Kato et al., 1990. All other HCV isolates known in the art may be aligned to this sequence to obtain the referred HCV polyprotein numbering for each individual HCV isolate. For instance, it is known that type 2 isolates can contain 4 extra codons/amino acids in their E2 sequence, while type 3 sequences have an insertion of 2 amino acids compared to type 1 sequences. The Examples section of the present invention describes T cell epitopes in, amongst other regions of the HCV structural region: the carboxyterminal region of the core protein (aa 73–176), amino acids 192 to 383 of the E1 region, amino acids 397 and 428 and amino acids 571 to 638 of the E2 region, amino acids 1188 to 1463 of the NS3 region. Groups of peptides covering parts of the structural proteins core and E2, and covering the complete E1 protein, as well as a recombinant NS3 protein have been studied. Peptides were tested as group 1 (aa 5–80), group 2 (aa 73–140), group 3 (aa 133–200), group 4 (aa 193–260), group 5 (aa 253–332), group 6 (325–392), group 7 (aa 427–494), group 8 (aa 487–578), and group 9 (aa 571–638) as shown in Table 1. Recombinant NS3 encompassed amino acids 1188 to 1463 of the isolate IG8309, belonging to the 1b subtype group of HCV.

The T cell response to the group 3 peptides, as well as to the individual peptides NS1–7* and NS1–5*shows a statistically relevant correlation with a decrease in alanine aminotransferase (ALT) and viral RNA levels, which are generally accepted to indicate a more benign course of the disease. A correlation between response to a recombinant HCV core protein and a more benign course of the disease has been described by Botarelli et al. 1993. However, no epitopes have been mapped nor has the sequence and exact position of the recombinant core protein been described in Botarelli et al., 1993. In the present invention, a similar T cell response has been observed to the group 2 peptides (aa 73–140) both in patients responding to IFN-α and in patients non-responding to the same. On the contrary, T cell reactivity to the group 3 peptides (aa 133–200) was observed in responders to interferon-α and differed from the T cell reactivity observed to this region in non-responders to IFN-α treatment. Furthermore, after investigating the reactivity of individual peptides from groups 2 and 3, this specific response correlating with a more benign course of HCV infection, could be further mapped to specific individual peptides termed CORE 23, CORE 25, and CORE 27. Peptide CORE 19, belonging to the group 2 peptides, was also recognized by some of the responders to IFN-α treatment (see FIG. 1).

The present invention thus also contemplates a polypeptide as defined above comprising or consisting of at least 8 to about 104 contiguous amino acids selected from the region comprised between amino acids 73 to 176, more particularly comprising or consisting of 8 to about 68 contiguous amino acids selected from the region comprised between amino acids 109 to 176 in the core region of HCV characterized by the following sequences:

$NH_2$-$GX_1X_2WX_3X_4PGX_5PWPLYX_6NX_7GX_8GX_9$ $AGWLLSPRGSRPX_{10}WGX_{11}$-$X_{12}DPRX_{13}X_{14}$ $SRNX_{15}GX_{16}VIDTX_{17}TCGX_{18}ADLX_{19}X_{20}YIPX_{21}$ $X_{22}G$-$X_{23}PX_{24}GGX_{25}X_{26}X_{27}X_{28}LX_{29}HGVRX_{30}X_{31}$ $X_{32}DGX_{33}NX_{34}X_{35}TGN$-$X_{26}PGCSFSI$-COOH (SEQ ID NO 58, spanning positions 73 to 176)

wherein $X_1$ represents R or K, $X_2$ represents A, S or T, $X_3$ represents A or G, $X_4$ represents Q, K or R, $X_5$ represents Y or H, $X_6$ represents G or A, $X_7$ represents E or K, $X8$ represents C, M or L, $X_9$ represents W or L, $X_{10}$ represents S, N, T, D or H, $X_{11}$ represents P or Q, $X_{12}$ represents N or T, $X_{13}$ represents R or H, $X_{14}$ represents R or K, $X_{15}$ represents L or V or F, $X_{16}$ represents K or R, $X_{17}$ represents L or I, $X_{18}$ represents F or L, $X_{19}$ represents M or I, $X_{20}$ represents G or E, $X_{21}$ represents L or V or I, $X_{22}$ represents V or L, $X_{23}$ represents A or G, $X_{24}$ represents L, V, or I, $X_{25}$ represents A or V, $X_{26}$ represents A or S, $X_{27}$ represents R or A, $X_{28}$ represents A or T or E, $X_{29}$ represents A or E, $X_{30}$ represents V or A or L, $X_{31}$ represents L or V or I, $X_{32}$ represents E or G, $X_{33}$ represents V or I, and $X_{34}$ represents F or Y, $X_{35}$ represents A or P, $X_{36}$ represents L or I, and, $NH_2$-$X_{11}X_{12}DPRX_{13}X_{14}SRNX_{15}GX_{16}VIDTX_{17}$ $TCGX_{18}ADLX_{19}X_{20}YIPX_{21}X_{22}G$-$X_{23}PX_{24}$ $GGX_{25}X_{26}X_{27}X_{28}LX_{29}HGVRX_{30}X_{31}X_{32}DGX_{33}$ $NX_{34}X_{35}TGN$-$X_{36}PGCSFSI$-COOH (SEQ ID NO 48, spanning positions 109 to 176)

wherein said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes, $X_{11}$ to $X_{36}$ having the meanings above-mentioned.

It is to be underlined that in the present text, $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, $X_{24}$, $X_{25}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$ have always the same meaning as the one which is defined for SEQ ID NO 58.

Preferentially said polypeptide is different from RALAH-GVRVLEDG (SEQ ID NO:179) spanning positions 149 to 161 of the core region of HCV.

More particularly, the present invention relates to a polypeptide as defined above comprising or consisting of at least 8 to about 76 contiguous amino acids selected from the regions comprised between amino acids 73 to 148, or comprising or consisting of 8 to about 15 contiguous amino acids selected from the region comprised between amino acids 162 to 176, or comprising or consisting of 8 to about 16 contiguous amino acids selected from the region comprised between amino acids 129 to 144 in the core region of HCV characterized by the following sequences:

$NH_2$-$GX_1X_2WX_3X_4PGX_5PWPLYX_6NX_7GX_8GX_9$ $AGWLLSPRGSRPX_{10}WGX_{11}$-$X_{12}DPRX_{13}$ $X_{14}SRNX_{15}GX_{16}VIDTX_{17}TCGX_{18}ADLX_{19}X_{20}$ $YIPX_{21}X_{22}G$-$X_{23}PX_{24}GGX_{25}X_{26}$-COOH (SEQ ID NO 59, spanning positions 73 to 148), $NH_2$-$X_{33}NX_{34}X_{35}TGNX_{36}PGCSFSI$-COOH (SEQ ID NO 60, spanning positions 162 to 176), and, $NH_2GX_{18}ADLX_{19}X_{20}YIPX_{21}X_{22}GX_{23}PX_{24}$ (SEQ ID NO 61, spanning positions 129 to 149). Particularly preferred is peptide ALMGYIPLV (SEQ ID NO 163).

Even more particularly, the present invention relates to the use of polypeptides as described above for the preparation of an HCV immunogenic composition.

The present invention thus also contemplates a polypeptide as defined above comprising or consisting of at least 8 to about 44 contiguous amino acids selected from the region comprised between amino acid positions 133 to 176 of the core region of HCV:

$NH_2$-$LX_{19}X_{20}YIPX_{21}X_{22}GX_{23}PX_{24}GGX_{25}X_{26}X_{27}X_{28}$ $LX_{29}HGVRX_{30}X_{31}X_{32}DGX_{33}NX_{34}X_{35}TGN$- $X_{36}PGCSFSI$-COOH (SEQ ID NO 50), and more particularly selected from peptide LMGYIPLVGA-PLGGAARALAHGVRVLEDGVNYAT GNLPGCS-FSI (SEQ ID NO 67), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Even more particularly, the present invention relates to the use of polypeptides as described above for the preparation of an HCV immunogenic composition.

The present invention thus also contemplates a polypeptide as defined above comprising or consisting of at least 8 to about contiguous amino acids selected from the region comprised between amino acid positions 157 to 176 of the core region of HCV:

$NH_2$-$X_{30}X_{31}X_{32}DGX_{33}NX_{34}X_{35}TGNX_{36}PGCSFSI$- COOH (SEQ ID NO 51), and more particularly selected from VLEDGVNYATGN-LPGCSFSI (SEQ ID NO 13=peptide CORE 27) or VLE-DIVNYATGNLPGCSFSI (SEQ ID NO 73), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes. Preferentially said peptides are further chosen from the following list of peptides:

$NH_2$-$GX_{33}NX_{34}X_{35}TGNX_{36}$-COOH (SEQ ID NO 74),
$NH_2$-$X_{33}NX_{34}X_{35}TGNX_{36}$-COOH (SEQ ID NO 75),
$NH_2$-$NX_{36}PGCSFSI$-COOH (SEQ ID NO 76) and
$NH_2$-$X_{36}PGCSFSI$-COOH (SEQ ID NO 77). Particularly preferred peptides include: GVNYATGNL (SEQ ID NO 78), GVNYATGNL (SEQ ID NO 79), NLPGCS-FSI (SEQ ID NO 80) and LPGCSFSI (SEQ ID NO 81).

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 145 to 164 of the core region of HCV:

$NH_2$-$GGX_{25}X_{26}X_{27}X_{28}LX_{29}HGVRX_{30}X_{31}X_{32}DGX_{33}NX_{34}$-COOH (SEQ ID NO 52), and more particularly selected from GGAARALAHGVRVLEDGVNY (SEQ ID NO 12=peptide CORE 25) or GGVAARALAHGVRVLEDGVNY (SEQ ID NO 118), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes. Preferentially said peptides according to the invention are chosen from the following list of peptides:

$NH_2$-$X_{28}LX_{29}HGVRX_{30}X_{31}$-COOH (SEQ ID NO 82),
$NH_2$-$LX_{29}HGVRX_{30}X_{31}$-COOH (SEQ ID NO 83),
$NH_2$-$GVRX_{30}X_{31}X_{32}DGX_{33}$-COOH (SEQ ID NO 84),
$NH_2$-$VRX_{30}X_{31}X_{32}DGX_{33}$-COOH (SEQ ID NO 85),
$NH_2$-$RX_{30}X_{31}X_{32}DGX_{33}NX_{34}$-COOH (SEQ ID NO 86), and
$NH_2$-$X_{30}X_{31}X_{32}DGX_{33}NX_{34}$-COOH (SEQ ID NO 87).

Particularly preferred peptides include: ALAHGVRVL (SEQ ID NO 88), LAHGVRVL (SEQ ID NO 89), VRVLEDGV (SEQ ID NO 90), RVLEDGV (SEQ ID NO 91), VLEDGVNY (SEQ ID NO 92), and LEDGVNY (SEQ ID NO 93).

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 133 to 152 of the core region of HCV:

$NH_2$-$LX_{19}X_{20}YIPX_{21}X_{22}GX_{23}PX_{24}GGX_{25}X_{26}X_{27}X_{28}LX_{29}$-COOH (SEQ ID NO 53), and more particularly selected from LMGYIPLVGAPLGGAARALA (SEQ ID NO 11=peptide CORE 23), and provided that said polypeptide is different from any known T cell epitope containing HCV peptide or polypeptide described from any of the above-mentioned regions. The latter known HCV polypeptides and peptides are described for screening for B cell epitopes. Preferentially said peptides according to the invention are chosen from the following list of peptides:

$NH_2$-$LX_{19}X_{20}YIPX_{21}X_{22}GX_{23}PX_{24}GGX_{25}$-COOH (SEQ ID NO 62),
$NH_2$-$X_{19}X_{20}YIPX_{21}X_{22}GX_{23}PX_{24}GGX_{25}$-COOH (SEQ ID NO 63),
$NH_2$-$YIPX_{21}X_{22}GX_{23}PX_{24}$-COOH (SEQ ID NO 64),
$NH_2$-$IPX_{21}X_{22}GX_{23}PX_{24}$-COOH (SEQ ID NO 65),
$NH_2$-$X_{21}X_{22}GX_{23}PX_{24}GGX_{25}$-COOH (SEQ ID NO 66), and
$NH_2$-$X_{22}GX_{23}PX_{24}GGX_{25}$-COOH (SEQ ID NO 68).

Prefered peptides chosen from this list include: LMGYIPLV (SEQ ID NO 69), MGYIPLV (SEQ ID NO 70), YIPLVGAPL (SEQ ID NO 71), IPLVGAPL (SEQ ID NO 72), LVGAPLGGA (SEQ ID NO 94), and VGAPLGGA (SEQ ID NO 95).

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 109 to 128 of the core region of HCV:

$NH_2$-$X_{11}X_{12}DPRX_{13}X_{14}SRNX_{15}GX_{16}VIDTX_{17}TC$-COOH (SEQ ID NO 54), and more particularly selected from PTDPRRRSRNLGKVIDTLTC (SEQ ID NO 9=peptide CORE 19), and provided that said polypeptide is different from any known T cell epitope containing HCV peptide or polypeptide described from any of the above-mentioned regions. The latter known HCV polypeptides and peptides are described for screening for B cell epitopes. Preferentially said peptides according to the present invention are chosen from the following peptides:

$NH_2$-$NX_{15}GX_{16}VIDTX_{17}$-COOH (SEQ ID NO 96) or
$NH_2$-$X_{15}GX_{16}VIDTX_{17}$-COOH (SEQ ID NO 97). Preferential peptides are for instance NLGKVIDTL (SEQ ID NO 98) and LGKVIDTL (SEQ ID NO 117).

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 73 to 92 of the core region of HCV: $NH_2$-$GX_1X_2WX_3X_4PGX_5PWPLYX_6NX_7GX_8G$-COOH (SEQ ID NO 99), and more particularly selected from GRTWAQPGYPWPLYGNEGCG (SEQ ID NO 6=peptide CORE 13), and provided that said polypeptide is different from any known T cell epitope containing HCV peptide or polypeptide described from any of the above-mentioned regions. The latter known HCV polypeptides and peptides are described for screening for B cell epitopes. Preferred peptides according to the present invention include for instance peptides further selected from:

$NH_2$-$X_2WX_3X_4PGX_5PW$-COOH (SEQ ID NO 100) and
$NH_2$-$WX_3X_4PGX_5PW$-COOH (SEQ ID NO 101), such as the peptides: TWAQPGYPW (SEQ ID NO 102) and WAQPGYPW (SEQ ID NO 103).

Even more particularly, the present invention relates to the use of polypeptides as described above for the preparation of an HCV immunogenic composition.

The present invention thus also contemplates a polypeptide as defined above comprising or consisting of at least 8 contiguous amino acids selected from the region comprised between amino acids 192 to 234 and 243 to 392 of HCV, more particularly selected from the region comprised between amino acids 192 to 234 and 243 to 383 in the E1 region of HCV characterized by the following sequences:

$NH_2$-YQVRNSTGLYHVTNDCPNSSIVYEAHDAILHTPGCVPCVREGN (SEQ ID NO 164, spanning positions 192 to 234), and, TPTVATTRDGKLPATQLRRHIDLLVGS-ATLCSALYVGDLCGSVQLFTFSPRRHWT-TQGCNCS IYPGHITGHRMAWDMMMN- WSPTAALVMAQLLRIPQAILDMIAGAHWGVLA
GIAYFSMVGNWAKVLVVLLLFAGVDAETIVS
GGQA-COOH (SEQ ID NO 104, spanning positions
243 to 392), or any variant to this sequence derived
from another type of HCV as depicted in FIG. 4,
wherein said contiguous amino acids containing a
T-cell stimulating epitope, and provided that said
polypeptide is different from any known T cell epitope
containing HCV peptide or polypeptide described from
any of the above-mentioned regions. The latter known
HCV polypeptides and peptides are described for
screening for B cell epitopes.

With said peptide being preferentially different from
RMAWDMM (SEQ ID NO:180) spanning positions 317 to
323 and ASPCWVAM (SEQ ID NO:177) spanning positions
235–242.

Even more particularly, the present invention relates to the
use of polypeptides as described above for the preparation of
an HCV immunogenic composition.

The present invention thus also contemplates a polypeptide as defined above comprising or consisting of at least 8
to about 68 contiguous amino acids selected from the region
comprised between amino acids 193 to 234 and 243 to 260
in the E1 region of HCV characterized by the following
sequence:

QVRNSTGLYHVTNDCPNSSIVYEAHDAI-
LHTPGCVPCVREGN (SEQ ID NO 165, spanning
positions 193 to 234), and, TPT VATTRDGKLPATQLR (SEQ ID NO 105, spanning
positions 243 to 260), or any variant to this sequence
derived from another type of HCV as depicted in FIG.
4, wherein said contiguous amino acids containing a
T-cell stimulating epitope, and provided that said
polypeptide is different from any known T cell epitope
containing HCV peptide or polypeptide described from
any of the above-mentioned regions. The latter known
HCV polypeptides and peptides are described for
screening for B cell epitopes.

Particularly preferred peptides according to the invention
include:

QVRNSTGLYHVTNDCPNSSI (SEQ ID NO 16),
NDCPNSSIVYEAHDAILHTP (SEQ ID NO 17),
HDAILHTPGCVPCVREGNVS (SEQ ID NO 18),
CVREGNVSRCWVAMTPTVAT (SEQ ID NO 19), and,
AMTPTVATRDGKLPPATQLRR (SEQ ID NO 20).

Even more particularly, the present invention relates to the
use of polypeptides as described above for the preparation of
an HCV immunogenic composition.

The present invention thus also contemplates a polypeptide as defined above comprising or consisting of at least 8
to about 80 contiguous amino acids selected from the region
comprised between amino acids 253 to 332 in the E1 region
of HCV characterized by the following sequence:

NH$_2$-
LPATQLRRHIDLLVGSATLCSALYVGDL-
CGSVQLFTFSPRRHWTTQGCNCSIYP
GHITGHRMAWDMMMNWSPTAAL-COOH (SEQ
ID NO 106), or any variant to this sequence derived
from another type of HCV as depicted in FIG. 4,
wherein said contiguous amino acids containing a
T-cell stimulating epitope, and provided that said
polypeptide is different from any known T cell epitope
containing HCV peptide or polypeptide described from
any of the above-mentioned regions. The latter known
HCV polypeptides and peptides are described for
screening for B cell epitopes.

Particularly preferred peptides according to the invention
include:

LPATQLRRHIDLLVGSATLC (SEQ ID NO 21),
LVGSATLCSALYVGDLCGSV (SEQ ID NO 22),
QLFTFSPRRHWTTQGCNCSI (SEQ ID NO 23),
TQGCNCSIYPGHITGHRMAW (SEQ ID NO 24), and,
ITGHRMAWDMMMNWSPTAAL (SEQ ID NO 25).

Even more particularly, the present invention relates to the
use of polypeptides as described above for the preparation of
an HCV immunogenic composition.

The present invention thus also contemplates a polypeptide as defined above comprising or consisting of at least 8
to about 68 contiguous amino acids selected from the region
comprised between amino acids 325 to 392 in the E1 region
of HCV characterized by the following sequence:

NH$_2$- MNWSPTAALVMAQLLRIPQAILDMIA-
GAHWGVLAGIAYFSMVGNW
AKVLVVLLLFAGVDAETIVSGGQA-COOH (SEQ
ID NO 107), or any variant to this sequence derived
from another type of HCV as depicted in FIG. 4,
wherein said contiguous amino acids containing a
T-cell stimulating epitope, and provided that said
polypeptide is different from any known T cell epitope
containing HCV peptide or polypeptide described from
any of the above-mentioned regions.

The latter known HCV polypeptides and peptides are
described for screening for B cell epitopes.

Particularly preferred peptides according to the present
invention include:

NWSPTAALVMAQLLRIPQAI (SEQ ID NO 26),
LLRIPQAILDMIAGAHWGVL (SEQ ID NO 27),
AGAHWGVLAGIAYFSMVGNW (SEQ ID NO 28), and,
VVLLLFAGVDAETIVSGGQA (SEQ ID NO 29).

Even more particularly, the present invention relates to the
use of polypeptides as described above for the preparation of
an HCV immunogenic composition.

The present invention also contemplates a polypeptide as
defined above comprising or consisting of at least 8 to about
32 contiguous amino acids selected from the region between
amino acids 397 to 428, or comprising or consisting of at
least 8 to about 68 contiguous amino acids selected from the
region between amino acids 571 to 638 in the E2 region of
HCV characterized by the following sequences:

NH$_2$-X$_{37}$X$_{38}$X$_{39}$X$_{40}$X$_{41}$X$_{42}$X$_{43}$X$_{44}$X$_{45}$GX$_{46}$X$_{47}$QX$_{48}$
X$_{49}$X$_{50}$LX$_{51}$NX$_{54}$NGSWHX$_{52}$NX$_{53}$TALN-COOH
(SEQ ID NO 49, spanning positions 397 to 428, see
FIG. 4), and, NH$_2$-IX$_{55}$X$_{56}$
X$_{57}$X$_{58}$NX$_{59}$X$_{60}$Z$_1$Z$_2$LX$_{61}$CPTDCFRKX$_{62}$PX$_{63}$
X$_{64}$TYX$_{65}$X$_{66}$CGX$_{67}$GPX$_{68}$X$_{69}$-TPRCX$_{70}$X$_{71}$
DYPYRLWHYPCTX$_{72}$NX$_{73}$X$_{74}$X$_{75}$FKX$_{76}$RMX$_{77}$
VGGVEH-COOH (SEQ ID NO 108, spanning positions 571 to 638, see FIG. 5).

wherein X$_{37}$ represents S, A, Q, L, N, Y, R, Y or H, X$_{38}$
represents G, S, T, A or R, X$_{39}$ represents F, I, L, or V;
X$_{40}$ represents V, A, or T; X$_{41}$ represents S, D or G; X$_{42}$
represents L, I, W, F, or M; X$_{43}$ represents L, I or F, X$_{44}$
represents A, T, D or S; X$_{45}$ represents P, Q, S, R, L, I
or T; X$_{46}$ represents A, P, or S; X$_{47}$ represents K, S, Q,
A, or R; X$_{48}$ represents N, K, D, or R; X$_{49}$ represents
V, I, or L; X$_{50}$ represents Q, S or Y; X$_{51}$ represents I or
V; X$_{52}$ represents L or I; X$_{53}$ represents S or R; and X$_{54}$
represents T or S; X$_{55}$ represents G or R; X$_{56}$ represents
G, A, or K, X$_{57}$ represents A, V, G, S, or D; X$_{58}$
represents G, F, or Y; X$_{59}$ represents N, H, R, L, A, or
S; X$_{60}$ represents T or S; Z$_1$ represents represents M or
I; Z$_2$ represents D; X$_{61}$ represents H, L, V, T, or I; X$_{62}$
represents H or Y; X$_{63}$ represents D or E; X$_{64}$ represents A or T; $X_{65}$ represents S, T, I, or L; $X_{66}$ represents R or K; $X_{67}$ represents S or A, $X_{68}$ represents W or L; $X_{69}$ represents I or L; $X_{70}$ represents L, M or I, $X_{71}$ represents V or I; $X_{72}$ represents I, V, F, or L; $X_{73}$ represents Y or F; $X_{74}$ represents T, S or A; $X_{75}$ represents I or V; $X_{76}$ represents I, V or A, $X_{77}$ represents Y or F, and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 397 to 416 of the E2 region of HCV: $NH_2\text{-}X_{37}X_{38}X_{39}X_{40}X_{41}X_{42}X_{43}X_{44}X_{45}GX_{46}X_{47}QX_{48}X_{49}X_{50}LX_{51}NX_{54}\text{-}COOH$ (SEQ ID NO 55), and more particularly selected from SGLVSLFTPGAKQNIQLINT (SEQ ID NO 46 or peptide NS1–7*), and provided that said polypeptide is different from any known T cell epitope containing HCV peptide or polypeptide described from any of the above-mentioned regions. The latter known HCV polypeptides and peptides are described for screening for B cell epitopes.

Even more particularly, the present invention relates to the use of polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 409 to 428 of the E2 region of HCV: $NH_2\text{-}QX_{48}X_{49}X_{50}LX_{51}NX_{54}NGSWHX_{52}NX_{53}TALN\text{-}COOH$ (SEQ ID NO 56)

and more particularly selected from QNIQLINTNG-SWHINSTALN (SEQ ID NO 47 or peptide NS1–5*), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes. Preferentially, the peptides according to the present invention are selected from the following list of peptides:

$NH_2\text{-}X_{50}LX_{51}NX_{54}NGSW\text{-}COOH$ (SEQ ID NO 109), $NH_2\text{-}LX_{51}NX_{54}NGSW\text{-}COOH$ (SEQ ID NO 110), $NH_2\text{-}SWHX_{52}NX_{53}TAL\text{-}COOH$ (SEQ ID NO 111), and $NH_2\text{-}SWHX_{52}NX_{53}TAL\text{-}COOH$ (SEQ ID NO 112).

Prefered peptides include for instance: QLINTNGSW (SEQ ID NO 113), LINTNGSW (SEQ ID NO 114), SWHINSTAL (SEQ ID NO 115) and WHINSTAL (SEQ ID NO 116).

Even more particularly, the present invention relates the use of to polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 571 to 638 of the E2 region of HCV:

$NH_2\text{-}IX_{55}X_{56}X_{57}X_{58}X_{59}X_{60}Z_1Z_2LX_{61}CPTDCFRKX_{62}PX_{63}X_{64}TYX_{65}X_{66}CGX_{67}GPX_{68}X_{69}\text{-}$
$TPRCX_{70}X_{71}DYPYRLWHYPCTX_{72}NX_{73}X_{74}X_{75}FKX_{76}RMX_{77}VGGVEH\text{-}COOH$ (SEQ ID NO 108), and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Preferred peptides according to the invention are chosen from the following list of peptides:

$X_{60}Z_1Z_2LX_{61}CPTDCF$ (SEQ ID NO 119), $FRKX_{62}PX_{63}X_{64}TY$ (SEQ ID NO 120), $X_{68}X_{69}\text{-}TPRCX_{70}X_{71}$ (SEQ ID NO 121), $X_{70}X_{71}DYPYRL$ (SEQ ID NO 122), $X_{71}DYPYRLW$ (SEQ ID NO 123),

YPYRLWHY (SEQ ID NO 124), $LWHYPCTX_{72}$ (SEQ ID NO 125), $X_{72}NX_{73}X_{74}X_{75}FKX_{76}$ (SEQ ID NO 126), $X_{73}X_{74}X_{75}FKX_{76}RM$ (SEQ ID NO 127), $X_{75}FKX_{76}RMX_{77}V$ (SEQ ID NO 128), $X_{76}RMX_{77}VGGV$ (SEQ ID NO 129), $IX_{55}X_{56}X_{57}X_{58}NX_{59}X_{60}Z_1Z_2LX_{61}CPTDCFRKX_{62}P$ (SEQ ID NO 130), $TDCFRKX_{62}PX_{63}X_{64}TYX_{65}X_{66}CGX_{67}GPX_{68}$ (SEQ ID NO 131), $X_{65}X_{66}CGX_{67}GPX_{68}X_{69}TPRCX_{70}X_{71}DYPYR$ (SEQ ID NO 132), $CX_{70}X_{71}DYPYRLWHYPCTX_{72}NX_{73}X_{74}X_{75}$ (SEQ ID NO 133), $PCTX_{72}NX_{73}X_{74}X_{75}FKX_{76}RMX_{77}VGGVEH$ (SEQ ID NO 134).

More preferentially, the peptides according to the present invention are selected from the following list of peptides:

IGGAGNNTLHCPTDCFRKHP (SEQ ID NO 41),

TDCFRKHPDATYSRCGSGPW (SEQ ID NO 42),

SRCGSGPWITPRCLVDYPYR (SEQ ID NO 43),

CLVDYPYRLWHYPCTINYTI (SEQ ID NO 44), and,

PCTINYTIFKIRMYVGGVEH (SEQ ID NO 45).

With said peptides being preferentially different from PDCFRKHP spanning positions 582 to 590 and YPYRLWH spanning positions 611 to 617.

Even more particularly, the present invention relates the use of to polypeptides as described above for the preparation of an HCV immunogenic composition.

The present invention thus also contemplates a polypeptide as defined above comprising or consisting of at least 8 to about 20 contiguous amino acids selected from the region comprised between amino acid positions 1188 to 1463 of the NS3 region of HCV characterized by the following sequence:

$NH_2$-GVAKAVDFVPVESMETTMRSPV FTDNSSP-PAVPQTFQVAHLHAPTGSGKSTKV-PAAYAAQGYKVLVLNPSVAATLGFGAYM-SKAHGVDPNIRTGVRTITTGAPITYST YGKFLADGGCSGGAYDIIICDECH-SIDSTSILGIGTVLDQAETAGARLVVLATAT PPGS-VTVPHPNIEEVALSSTGEIPFYGKAIP-IEVIKGGRHLIFCHSKKKCDELAAKLSGFGI NAVAYYRGLDVSVIPTSGDVVVVATDALMTGF TGDFDSVIDCNTCVTQTVDFS-COOH (SEQ ID NO 57), or any variant of said sequence as can be deduced from FIG. 6, and with said contiguous amino acids containing a T-cell stimulating epitope, and provided that said polypeptide is different from any known T cell epitope containing HCV peptide or polypeptide described from any of the above-mentioned regions. The latter known HCV polypeptides and peptides are described for screening for B cell epitopes.

Preferentially said peptides are chosen from the following list of peptides:

VAKAVDFV (SEQ ID NO 135), VAKAVDFI (SEQ ID NO 136), VESMETTM (SEQ ID NO 137), AVPQTFQV (SEQ ID NO 138), YAAQGYKV (SEQ ID NO 139), VLVLNPSVA (SEQ ID NO 140), YMSKAHGV (SEQ ID NO 141), IRTGVRTI (SEQ ID NO 142), YSTYGKFL (SEQ ID NO 143), ILGIGTVL (SEQ ID NO 144), VTVPHPNI (SEQ ID NO 145), IPFYGKAI (SEQ ID NO 146), FYGKAIPI (SEQ ID NO 147), VIKGGRHL (SEQ ID NO 148), IKGGRHLI (SEQ ID NO 149), FCHSKKKC (SEQ ID NO 150), CDELAAKL (SEQ ID NO 151), LAAKLSGFG (SEQ ID NO 152), SGFGINAV (SEQ ID NO 153), FGINAVAY (SEQ ID NO 154), YRGLDVSV (SEQ ID NO 155), VIPTSGDV (SEQ ID NO 156), IPTSGDVV (SEQ ID NO 157), VVVATDAL (SEQ ID NO 158), VVATDALM (SEQ ID NO 159), MTGFTGDF (SEQ ID NO 160), FTGDFDSV (SEQ ID NO 161), KLVALGINAV (SEQ ID NO 166), VIDCNTCV (SEQ ID NO 162), or any variant of said sequence as can be deduced from FIG. 6.

With said peptides being preferentially different from GKSTKVP, PSVAAT, IGTVLDQAE, AVAYYR, ASRCWVAM and TGDFDSVID (SEQ ID NOs: 173–178, respectively).

The present invention relates more particularly to any of the above-mentioned polypeptides wherein said T cell stimulating epitope is a T cell helper epitope.

According to another embodiment, the present invention relates to any of the above-mentioned polypeptides wherein T cell stimulating epitope is a CTL epitope.

The present invention also relates to the incorporation of any of the above-mentioned polypeptides into a prophylactic vaccine composition.

According to another embodiment, the present invention relates to the incorporation of any of the above-mentioned polypeptides into a therapeutic vaccine composition.

Moreover, the present invention also contemplates a polypeptide comprising or consisting of multiple repeats of any of the polypeptides as defined above, combinations of any of the polypeptides as defined above, or mimotopes of the peptides as defined above.

The term "mimotopes" refers to peptides which mimic the polypeptides as defined above immunologically. Since sequence variability has been observed fro HCV, it may be desirable to vary one or more amino acids so as to better mimic the epitopes of different strains. It should be understood that such mimotopes need not be identical to any particular HCV sequence as long as the subject compounds are capable of providing for immunological stimulation after which the T cells are reactive with at least one strain of HCV. The polypeptides as described above, may therefore be subject to insertions, deletions and conservative as well as non-conservative amino acid subtitutions where such changes might provide for certain advantages in their use. The peptides will preferably be as short as possible while still maintaining all of their sensitivity of the larger sequence. In certain cases, it may be desirable to join two or more peptides into a single structure. The formation of such a composite may involve covalent or non-covalent linkages.

The present invention also contemplates a polypeptide as defined above, with said polypeptide being a recombinant polypeptide expressed by means of an expression vector comprising a nucleic acid insert encoding a polypeptide as defined above.

In order to carry out the expression of the T-cell containing polypeptides of the invention in bacteria such as $E.\ coli$ or in eukaryotic cells such as in $S.\ cerevisiae$, or in cultured vertebrate or invertebrate hosts such as insect cells, Chinese Hamster Ovary (CHO), COS1, BHK, and MDCK cells, the following steps are carried out:

transformation of an appropriate cellular host with a recombinant vector, or by means of adenoviruses, influenza viruses, BCG, and any other live carrier systems, in which a nucleotide sequence coding for one of the polypeptides of the invention has been inserted under the control of the appropriate regulatory elements, particularly a promoter recognized by the polymerases of the cellular host or of the live carrier system and in the case of a prokaryotic host, an appropriate ribosome binding site (RBS), enabling the expression in said cellular host of said nucleotide sequence, culture of said transformed cellular host under conditions enabling the expression of said insert. Recombinant virus or live carrier vectors may also be directly used as live vaccines in humans.

According to a preferred embodiment, the present invention contemplates a polypeptide as defined above which is operably linked to a pathogen related immunogen such as the HCV core protein, the HCV envelope proteins E1 and E2, or the HCV NS3, NS4 or NS5 immunogens, or a HCV peptide containing a B cell epitope.

The phrase "operatively linked" as used herein means that the linkage does not interfere with the ability of either of the linked groups to function as described; e.g., to function as a T or B cell determinant. Thus, operatively linking not only includes covalent linkages, but also includes linkages capable of inducing T cell function.

The phrase "pathogen related" as used herein designates a polypeptide that is capable of inducing the T cell function that immunoreacts with a pathogen in native form.

The defined polypeptides can be employed as such or in combination with HCV B cell epitopes, HBsAg or HBcAg particles, HIV immunogens, HTLV immunogens. HCV peptides containing preferred B cell epitopes are detailed in for instance EP-A-0 489 968 and WO 93/18054.

Methods for operatively linking individual polypeptides through an amino acid residue side chain to form an immunogenic conjugate, i.e., a branched-chain polypeptide polymer, are well known in the art. Those methods include linking through one or more types of functional groups on various side chains and result in the respective polypeptide backbones being covalently linked (coupled) but separated by at least one side chain.

Useful side chain functional groups include epsilon-amino groups, beta- or gamma-carboxyl groups, thiol (—SH) groups and aromatic rings (e.g. tyrosine and histidine). Methods for linking polypeptides using each of the above functional groups are described in Erlanger (1980), Aurameas et al. (1978) and U.S. Pat. No. 4,493,795 to Nestor et al. In addition, a site-directed coupling reaction, as described in Rodwell et al. (1985), can be carried out so that the biological activity of the polypeptides is not substantially diminished.

Furthermore, as is well known in the art, the HBcAg protein and polypeptide immunogen can be used in their native form or their functional group content may be modified by succinylation of lysine residues or reaction with cysteine-thiolactone. A sulfhydryl group may also be incorporated into either polypeptide by reaction of amino functions with 2-iminothiolane or the N-hydroxysuccinimide ester of 3-(3-dithiopyridyl) propionate. The polypeptides can also be modified to incorporate spacer arms, such as hexamethylene diamine or other bifunctional molecules of similar size, to facilitate linking.

Any polypeptide immunogen against which antibody production is desired can be linked to the polypeptide of the present invention protein to form an immunogenic conjugate of this invention. In preferred embodiments the polypeptide immunogen is a pathogen related immunogen and the conjugate has the capacity to induce the production of antibodies that immunoreact with the pathogen when injected in an effective amount into an animal. Exemplary immunogens of particular importance are derived from bacteria such as *B. pertussis, S. typosa, S. Paratyphoid* A and B, *C. diptheriae, C. tetani, C. botulinum, C. oerfrincens, B. anthracis, P. pestis, P. multocida, V. cholerae, N. meningitides, N. gonorrhea, H. influenzae, T. palladium,* and the like; immunogens derived from viruses such as polio virus, adenovirus, parainfluenza virus, measles, mumps, respiratory syncytical virus, influenza virus, equine encephalomyeitis virus, hog chloera virus, Newcastle virus, fowl pox virus, rabies virus, feline and canine distemper viruses, foot and mouth disease virus, human and simian immunodeficiency viruses, and the like; rickettsiae immunogen such as epidemic and endemic typhus, and the spotted fever groups, and the like. Immunogens are well known to the prior art in numerous references such as U.S. Pat. No. 3,149,036, U.S. Pat. No. 3,983,228, and U.S. Pat. No. 4,069,313; in *Essential Immunology*, 3rd Ed., by Roit, published by Blackwell Scientific Publications; in *Fundamentals of Clinical Immunology*, by Alexander and Good, published by W. B. Saunders; and in *Immunology*, by Bellanti, published by W. B. Saunders. Particularly preferred pathogen related immunogens are those described in U.S. Pat. No. 4,625,015, U.S. Pat. No. 4,544,500, U.S. Pat. No. 4,545,931, U.S. Pat. No. 4,663,436, U.S. Pat. No. 4,631,191, U.S. Pat. No. 4,629,783 and in Patent Cooperation Treaty International Publication No. WO87/02775 and No. WO87/02892, all of whose disclosures are incorporated herein by reference.

The present invention relates particularly to any of the following peptides or any peptide comprised in the sequence of any of the following peptides, with said peptides containing a T cell epitope:

$NH_2$-$X_{30}X_{31}X_{32}DGX_{33}NX_{34}X_{35}TGNX_{36}PGCSFSI$-COOH (SEQ ID NO 51),

VLEDGVNYATGNLPGCSFSI (SEQ ID NO 13=peptide CORE 27),

VLEDIVNYATGNLPGCSFSI (SEQ ID NO 73), $NH_2$-$GX_{33}NX_{34}X_{35}TGNX_{36}$-COOH (SEQ ID NO 74), $NH_2$-$X_{33}NX_{34}X_{35}TGNX_{36}$-COOH (SEQ ID NO 75), $NH_2$-$NX_{36}PGCSFSI$-COOH (SEQ ID NO 76), $NH_2$-$X_{36}PGCSFSI$-COOH (SEQ ID NO 77),

GVNYATGNL (SEQ ID NO 78), GVNYATGNL (SEQ ID NO 79),

NLPGCSFSI (SEQ ID NO 80), LPGCSFSI (SEQ ID NO 81), $NH_2$-$GGX_{25}X_{26}X_{27}X_{28}LX_{29}HGVRX_{30}X_{31}X_{32}DGX_{33}NX_{34}$-COOH (SEQ ID NO 52),

GGAARALAHGVRVLEDGVNY (SEQ ID NO 12=peptide CORE 25),

GGVAARALAHGVRVLEDGVNY (SEQ ID NO 118), $NH_2$-$X_{28}LX_{29}HGVRX_{30}X_{31}$-COOH (SEQ ID NO 82), $NH_2$-$LX_{29}HGVRX_{30}X_{31}$-COOH (SEQ ID NO 83), $NH_2$-$GVRX_{30}X_{31}X_{32}DGX_{33}$-COOH (SEQ ID NO 84), $NH_2$-$VRX_{30}X_{31}X_{32}DGX_{33}$-COOH (SEQ ID NO 85), $NH_2$-$RX_{30}X_{31}X_{32}DGX_{33}NX_{34}$-COOH (SEQ ID NO 86), $NH_2$-$X_{30}X_{31}X_{32}DGX_{33}NX_{34}$-COOH (SEQ ID NO 87),

ALAHGVRVL (SEQ ID NO 88), LAHGVRVL (SEQ ID NO 89),

VRVLEDGV (SEQ ID NO 90), RVLEDGV (SEQ ID NO 91), VLEDGVNY (SEQ ID NO 92), LEDGVNY (SEQ ID NO 93), $NH_2$-$LX_{19}X_{20}YIPX_{21}X_{22}GX_{23}PX_{24}GGX_{25}X_{26}X_{27}X_{28}LX_{29}$-COOH (SEQ ID NO 53),

LMGYIPLVGAPLGGAARALA (SEQ ID NO 11=peptide CORE 23), $NH_2$-$LX_{19}X_{20}YIPX_{21}X_{22}GX_{23}PX_{24}GGX_{25}$-COOH (SEQ ID NO 62), $NH_2$-$X_{19}X_{20}YIPX_{21}X_{22}GX_{23}PX_{24}GGX_{25}$-COOH (SEQ ID NO 63), $NH_2$-$YIPX_{21}X_{22}GX_{23}PX_{24}$-COOH (SEQ ID NO 64), $NH_2$-$IPX_{21}X_{22}GX_{23}PX_{24}$-COOH (SEQ ID NO 65), $NH_2$-$X_{21}X_{22}GX_{23}PX_{24}GGX_{25}$-COOH (SEQ ID NO 66), $NH_2$-$X_{22}GX_{23}PX_{24}GGX_{25}$-COOH (SEQ ID NO 68),

LMGYIPLV (SEQ ID NO 69), MGYIPLV (SEQ ID NO 70),

YIPLVGAPL (SEQ ID NO 71), IPLVGAPL (SEQ ID NO 72),

LVGAPLGGA (SEQ ID NO 94), VGAPLGGA (SEQ ID NO 95), $NH_2$-$X_{11}X_{12}DPRX_{13}X_{14}SRNX_{15}GX_{16}VIDTX_{17}TC$-COOH (SEQ ID NO 54),

PTDPRRRSRNLGKVIDTLTC (SEQ ID NO 9=peptide CORE 19), $NH_2$-$NX_{15}GX_{16}VIDTX_{17}$-COOH (SEQ ID NO 96), $NH_2$-$X_{15}GX_{16}VIDTX_{17}$-COOH (SEQ ID NO 97),

NLGKVIDTL (SEQ ID NO 98), LGKVIDTL (SEQ ID NO 117), $NH_2$-$GX_1X_2WX_3X_4PGX_5PWPLYX_6NX_7GX_8G$-COOH (SEQ ID NO 99),

GRTWAQPGYPWPLYGNEGCG (SEQ ID NO 6=peptide CORE 13), $NH_2$-$X_2WX_3X_4PGX_5PW$-COOH (SEQ ID NO 100), $NH_2$-$WX_3X_4PGX_5PW$-COOH (SEQ ID NO 101),

TWAQPGYPW (SEQ ID NO 102), WAQPGYPW (SEQ ID NO 103),

QVRNSTGLYHVTNDCPNSSI (SEQ ID NO 16),

NDCPNSSIVYEAHDAILHTP (SEQ ID NO 17),

HDAILHTPGCVPCVREGNVS (SEQ ID NO 18),

CVREGNVSRCWVAMTPTVAT (SEQ ID NO 19),

AMTPTVATRDGKLPPATQLRR (SEQ ID NO 20),

LPATQLRRHIDLLVGSATLC (SEQ ID NO 21),

LVGSATLCSALYVGDLCGSV (SEQ ID NO 22),

QLFTFSPRRHWTTQGCNCSI (SEQ ID NO 23),

TQGCNCSIYPGHITGHRMAW (SEQ ID NO 24),

ITGHRMAWDMMMNWSPTAAL (SEQ ID NO 25),

NWSPTAALVMAQLLRIPQAI (SEQ ID NO 26),

LLRIPQAILDMIAGAHWGVL (SEQ ID NO 27),

AGAHWGVLAGIAYFSMVGNW (SEQ ID NO 28),

VVLLLFAGVDAETIVSGGQA (SEQ ID NO 29), $NH_2$-$X_{37}X_{38}X_{39}X_{40}X_{41}X_{42}X_{43}X_{44}X_{45}GX_{46}GX_{47}QX_{48}X_{49}X_{50}LX_{51}NX_{54}$-COOH (SEQ ID NO 55),

SGLVSLFTPGAKQNIQLINT (SEQ ID NO 46),
NH$_2$-QX$_{48}$X$_{49}$X$_{50}$LX$_{51}$NX$_{54}$NGSWHX$_{52}$NX$_{53}$TALN-COOH (SEQ ID NO 56),
NH$_2$-X$_{50}$LX$_{51}$NX$_{54}$NGSW-COOH (SEQ ID NO 109),
NH$_2$-LX$_{51}$NX$_{54}$NGSW-COOH (SEQ ID NO 110),
NH$_2$-SWHX$_{52}$NX$_{53}$TAL-COOH (SEQ ID NO 111),
NH$_2$-SWHX$_{52}$NX$_{53}$TAL-COOH (SEQ ID NO 112),
QLINTNGSW (SEQ ID NO 113),
LINTNGSW (SEQ ID NO 114), SWHINSTAL (SEQ ID NO 115), WHINSTAL (SEQ ID NO 116),
GGAGNNTLHCPTDCFRKHP (SEQ ID NO 41),
TDCFRKHPDATYSRCGSGPW (SEQ ID NO 42),
SRCGSGPWITPRCLVDYPYR (SEQ ID NO 43),
CLVDYPYRLWHYPCTINYTI (SEQ ID NO 44),
PCTINYTIFKIRMYVGGVEH (SEQ ID NO 45),
X$_{60}$Z$_1$Z$_2$LX$_{61}$CPTDCF (SEQ ID NO 119),
FRKX$_{62}$PX$_{63}$X$_{64}$TY (SEQ ID NO 120),
X$_{68}$X$_{69}$-TPRCX$_{70}$X$_{71}$ (SEQ ID N 121),
X$_{70}$X$_{71}$DYPYRL (SEQ ID NO 122),
X$_{71}$DYPYRLW (SEQ ID NO 123),
YPYRLWHY (SEQ ID NO 124),
LWHYPCTX$_{72}$ (SEQ ID NO 125),
X$_{72}$NX$_{73}$X$_{74}$X$_{75}$FKX$_{76}$ (SEQ ID NO 126),
X$_{73}$X$_{74}$X$_{75}$FKX$_{76}$RM (SEQ ID NO 127),
X$_{75}$FKX$_{76}$RMX$_{77}$V (SEQ ID NO 128),
X$_{76}$RMX$_{77}$VGGV (SEQ ID NO 129),
IX$_{55}$X$_{56}$X$_{57}$X$_{58}$NX$_{59}$X$_{60}$Z$_1$Z$_2$LX$_{61}$CPTDCFRKX$_{62}$P (SEQ ID NO 130),
TDCFRKX$_{62}$PX$_{63}$X$_{64}$TYX$_{65}$X$_{66}$CGX$_{67}$GPX$_{68}$ (SEQ ID NO 131),
X$_{65}$X$_{66}$CGX$_{67}$GPX$_{68}$X$_{69}$TPRCX$_{70}$X$_{71}$DYPYR (SEQ ID NO 132),
CX$_{70}$X$_{71}$DYPYRLWHYPCTX$_{72}$NX$_{73}$X$_{74}$X$_{75}$ (SEQ ID NO 133),
PCTX$_{72}$NX$_{73}$X$_{74}$X$_{75}$FKX$_{76}$RMX$_{77}$VGGVEH (SEQ ID NO 134).
VAKAVDFV (SEQ ID NO 135), VAKAVDFI (SEQ ID NO 136), VESMETTM (SEQ ID NO 137), AVPQTFQV (SEQ ID NO 138), YAAQGYKV (SEQ ID NO 139), VLVLNPSVA (SEQ ID NO 140), YMSKAHGV (SEQ ID NO 141), IRTGVRTI (SEQ ID NO 142), YSTYGKFL (SEQ ID NO 143), ILGIGTVL (SEQ ID NO 144), VTVPHPNI (SEQ ID NO 145), IPFYGKAI (SEQ ID NO 146), FYGKAIPI (SEQ ID NO 147), VIKGGRHL (SEQ ID NO 148), IKGGRHLI (SEQ ID NO 149), FCHSKKKC (SEQ ID NO 150), CDELAAKL (SEQ ID NO 151), LAAKLSGFG (SEQ ID NO 152), SGFGINAV (SEQ ID NO 153), FGINAVAY (SEQ ID NO 154), YRGLDVSV (SEQ ID NO 155), VIPTSGDV (SEQ ID NO 156), IPTSGDVV (SEQ ID NO 157), VVVATDAL (SEQ ID NO 158), VVATDALM (SEQ ID NO 159), MTGFTGDF (SEQ ID NO 160), FTGDFDSV (SEQ ID NO 161), VIDCNTCV (SEQ ID NO 162).

Moreover, the present invention contemplates an immunogenic composition consisting of or comprising at least one of the polypeptides as defined above mixed with a pharmaceutical acceptable excipient.

Before administration to patients, formulants may be added to the polypeptides or peptides of the invention. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. Sucrose is most preferred. "Sugar alcohol" is defined as a C4 to C8 hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v % Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP patent applications No. EP 0 270 799 and EP 0 268 110.

Additionally, polypeptides can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546. Preferred polymers are polyoxyethylated polyols and polyethylene glycol (PEG). PEG is soluble in water at room temperature and has the general formula: R(O—CH$_2$—CH$_2$)$_n$O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated. However, it will be understood that the type and amount of the reactive groups may be varied to achieve a covalently conjugated PEG/polypeptide of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, and a discussion of POG/IL-2 conjugates is found in U.S. Pat. No. 4,766,106.

Another drug delivery system for increasing circulatory half-life is the liposome. Methods of preparing liposome delivery systems are discussed in Gabizon et al., 1982; and Szoka, 1980. Other drug delivery systems are known in the art and are described in, e.g. Poznansky, 1984.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the polypeptides and compositions of this invention are used to treat human patients to prevent or treat any of the above-defined disease states. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks' solution. Nonaqueous vehicles such as fixed oils and ethyl oleate may also be used. A preferred vehicle is 5% dexErose in saline. The vehicle may contain minor amounts of additives such as substances that enhance isotonicity and chemical stability, including buffers and preservatives.

The dosage and mode of administration will depend on the individual.

More particularly, the present invention contemplates a composition as defined above for use in a method of immunizing against HCV, comprising administrating a sufficient amount of at least one of the polypeptides as defined above, possibly accompanied by pharmaceutically acceptable adjuvants, to produce an immune response.

More particularly, said immunogenic composition is a vaccine composition. Even more particularly, said vaccine composition is a prophylactic vaccine composition. Alternatively, said vaccine composition may also be a therapeutic vaccine composition.

The prophylactic vaccine composition refers to a vaccine composition aimed for preventing HCV infection and to be administered to normal persons who are not yet infected with HCV.

The therapeutic vaccine composition refers to a vaccine composition aimed for treatment of HCV infection and to be administered to patients being infected with HCV.

The polypeptides described in the present invention can be modified with lipid (lipopeptides, e.g. $PAM_3Cys$), and formulated with alum, monophosphoryl lipid A, pluronics, SAF1, Ribi, trehalose-6,6-dimycolate or other immunostimulating compounds known to those skilled in the art, as to enhance their immunogenicity.

Also, the present invention contemplates according to a preferred embodiment, a composition as defined above, with said composition comprising in addition to any of the T cell-stimulating polypeptides as defined above, a peptide or polypeptide containing at least one B-cell epitope of HCV, and/or a structural HCV polypetide, and/or a non-structural HCV polypeptide.

According to a yet other preferred embodiment, the present invention contemplates a composition as defined above for use in a method of treatment of HCV, comprising administrating a sufficient amount of at least one of the polypeptides as defined above, possibly accompanied by pharmaceutically acceptable adjuvants, to allow treatment of HCV infection. In this case the polypeptides of the present invention can be employed in the form of therapeutic vaccine, aiming at the induction of a sufficient level of T cell function for clearance of Hepatitis C virus infection.

According to yet another preferred embodiment, the present invention contemplates a composition as defined above, with said composition comprising in addition to any of the polypeptides as defined above, a peptide or polypeptide containing at least one B-cell epitope of HCV, and/or a structural HCV polypeptide, and/or a non-structural HCV polypeptide.

According to yet another embodiment, the present invention contemplates a composition wherein said polypeptides as defined above are mixed with HBsAg or HBcAg paricles, HBV immunogens, HIV immunogens and/or HTLV immunogens.

FIGURE LEGENDS

FIG. 1: Evolution of the lymphoproliferative responses and transaminase activities in HCV patient No. 632. AST depicts aspartate aminotransferase, ALT depicts alanine aminotransferase; SI: simulation index; P1 to P6 refers to the groups of peptides 1 to 6 as disclosed in Table 1.

FIG. 2: Frequencies of lymphoproliferation responses to peptide pools 1–9, single peptides NS1–7*, NS1–5* and recombinant NS3 protein in healthy controls, interferon (IFN) responders and IFN non-responders.

FIG. 3: represents the part of the sequence of the isolate IG8309 which has been tested, with said part extending from with Gly at position 41 to Ser at position 318 (SEQ ID NO 57).

Figure 4M:
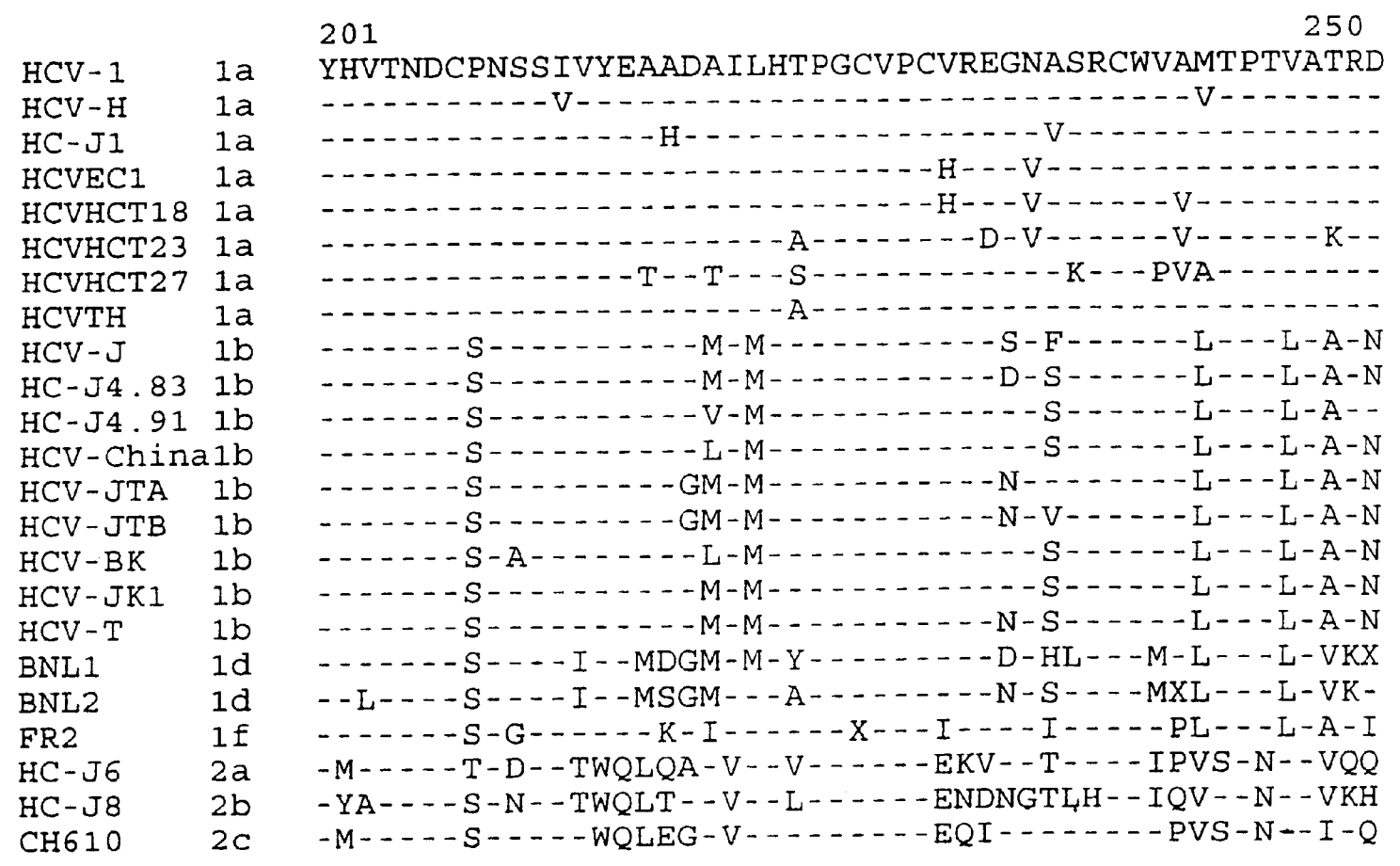

FIG. 4A represents an alignment of the HCV structural regions.

FIG. 4B represents an alignment of the HCV structural regions.

FIG. 4D represents an alignment of the HCV structural regions.

FIG. 4E represents an alignment of the HCV structural regions.

FIG. 4F represents an alignment of the HCV structural regions.

FIG. 4G represents an alignment of the HCV structural regions.

FIG. 4H represents an alignment of the HCV structural regions.

FIG. 4I represents an alignment of the HCV structural regions.

FIG. 4J represents an alignment of the HCV structural regions.

FIG. 4K represents an alignment of the HCV structural regions.

FIG. 4L represents an alignment of the HCV structural regions.

FIG. 4M represents an alignment of the HCV structural regions.

FIG. 4N represents an alignment of the HCV structural regions.

FIG. 4O represents an alignment of the HCV structural regions.

FIG. 4P represents an alignment of the HCV structural regions.

FIG. 4Q represents an alignment of the HCV structural regions.

FIG. 4R represents an alignment of the HCV structural regions.

FIG. 4S represents an alignment of the HCV structural regions.

FIG. 4T represents an alignment of the HCV structural regions.

FIG. 4U represents an alignment of the HCV structural regions.

FIG. 4V represents an alignment of the HCV structural regions.

FIG. 4W represents an alignment of the HCV structural regions.

Figure 1:
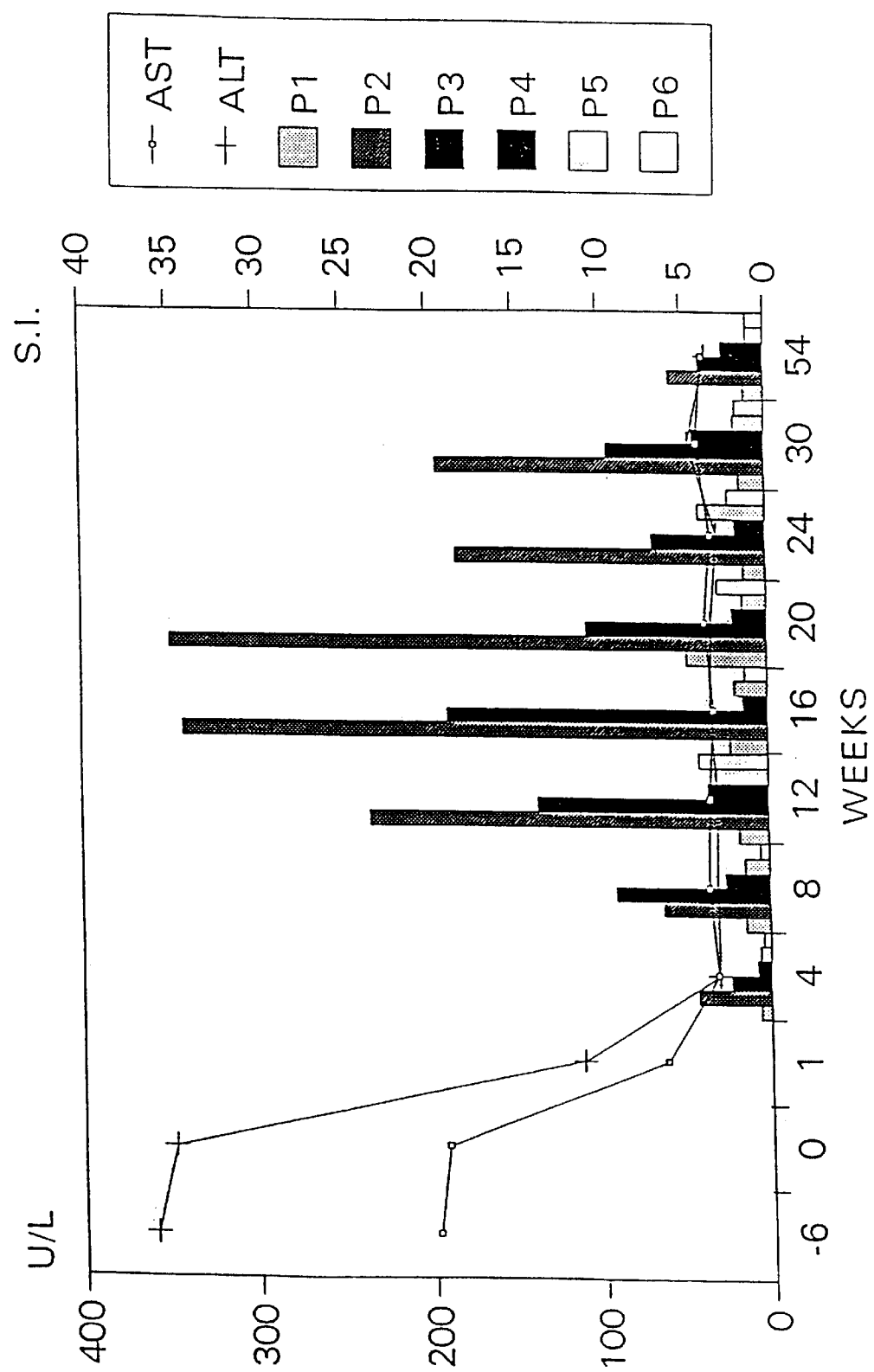

FIG. 5A. Alignment of E2 regions spanning amino acid positions 571 to 638.

FIG. 5B. Alignment of E2 regions spanning amino acid positions 571 to 638.

FIG. 6A. Alignment of NS3 sequences spanning amino acid positions 1188 to 1465.

FIG. 6B. Alignment of NS3 sequences spanning amino acid positions 1188 to 1465.

FIG. 6C. Alignment of NS3 sequences spanning amino acid positions 1188 to 1465.

EXAMPLES

Example 1

Patients Studied

The patients studied consisted of 19 males and 13 females, aged between 27 and 71 (mean age: 49.9 years). The diagnosis of chronic HCV hepatitis was based on a) a documented elevation of alanine aminotransferase of 2 times the upper limit of normal for at least six months; b) the presence of HCV-specific serum antibodies detected by two second generation enzyme immunoassay tests (UBI test and Innotest HCV AbII, Innogenetics, Antwerp Belgium) and c) absence of clinical, histological or serological signs of other viral, toxic, metabolic, hereditary or auto-immune hepatitis. The patients were randomized to receive either the standard treatment consisting of 3 million units Interferon α-2b (INTRON A) given thrice weekly for 24 weeks or an experimental treatment consisting of an induction phase of 6 million units Interferon α-2b thrice weekly for eight weeks, followed by a maintenance phase of titrated doses of interferon of 6 to 1 million units thrice weekly until biochemical and virological remission (alanine aminotransferase activity normal, plasma hepatitis C virus-RNA undetectable) was achieved. Patients were considered clinical responders when a normalization of alanine aminotransferase activity was observed on at least two successive control visits during treatment with al least one month interval.

As controls for the specificity of the lymphoproliferative responses, 18 healthy individuals aged 25–58 years (mean 38.6), 10 males and 8 females were selected. These subjects were negative for HCV antibodies and HCV-RNA. One subject had a history of past hepatitis B virus infection and 7 had antibodies to HBsAg as a result of vaccination.

A liver biopsy was-performed in all patients prior to the initiation of Interferon-α therapy. The histological status was defined according to conventional histological classification (Knodell et al., 1981).

Based on the definition of clinical responders given above, 18 subjects could be considered clinical responders to Interferon-α. The most relevant clinical, pathological and virological data of both groups are summarized in Table 2. Although the responder group contained more women and the non-responder group more men than theoretically expected, the observed imbalances were not significant ($X^2$-test). The duration of the disease in each subject was estimated based on anamnestic data (surgery with multiple transfusions, intravenous drug abuse, professional exposure through needle stick accident, etc.) or patient file data displaying chronically fluctuating and elevated transaminase levels. The disease duration varied from one to 32 years. The mean disease duration was 9.2±9.2 years in responders and 6.8±5.4 years in non-responders. Although the responder group contained more subjects treated with the experimental protocol and the non-responder group more subjects treated with the standard protocol, the imbalance was not significant $X^2$-test). Twenty six out of 32 patients (81%) were infected with HCV of genotype 1b. The genotypes 3a, 4a and 5a were found in 4, 1 and 1 subject, respectively. Anamnestic data allowed us to retrieve the source of infection. Blood transfusions are the possible source of the HCV infection in 14 subjects, IV drug abuse in 3 patients and needle stick accidents in 3 others. No source of infection could be traced back in 12 subjects. Most patients (20 out of 32) showed pathological lesions compatible with chronic active hepatitis in a mild, moderate or severe form. Seven patients displayed signs of chronic persistent hepatitis. In two subjects the biopsy showed only aspecific lesions and in two others signs of liver cirrhosis were observed.

Example 2

Analysis of the Humoral Immune Response

INNO-LIA HCV AbII (Innogenetics, Belgium) was employed to detect antibodies to peptide epitopes from the core, NS4a+b and NS5a region. From each patient a serum sample obtained before the start of the interferon therapy was examined and sometimes, additional follow-up samples were also tested. All 32 patients studied had circulating antibodies towards HCV demonstrated by two commercially available enzyme immunoassays. Using a peptide-based immunoblot assay (INNO-LIA HCV AbII) we were able to partially define the specificities of these antibodies. Sera from 31 patients were examined at least once with this assay and in 20 subjects the assay was applied on two sera taken with an interval of 4 (Patient 635) to 124 weeks (Patient 606). Table 3 shows the results of this survey. Apart from the reactivity pattern with the antigens employed (4 individually spotted core peptides, a mixture of NS4 peptides defining a fifth line and a selection of NS5 peptides creating a sixth line), Table 3 also shows the HCV genotype and the moment at which the serum was taken with respect to the start of the interferon therapy. The data clearly indicate that the antibody recognition pattern of an individual patient hardly changes over time. The only differences observed in the 20 paired samples were single step alterations in the intensity of the reactions. As well in responders as in non-responders to interferon we observed the same hierarchy in the serological reaction patterns. When indeterminate or weak reactions are not taken into consideration, the following hierarchy appears: Core2>NS4>NS5>Core1>Core4>Core3.

Example 3

Detection of ECV RNA and HCV Genotyping

Reverse transcription and PCR was performed as described previously (Stuyver et al, 1993). PCR products were further processed for genotyping by means of the Inno-LiPA genotyping assay (Stuyver et al., 1993). The results of the genotyping assays are included in Table 3.

Example 4

Analysis of the Cellular Immune Response

4.1. Synthesis of HCV Antigens

Nine groups of peptides (pools) corresponding to Core, E1 and E2/NS1 sequences, two single peptides not included in these pools corresponding to E2/NS1, and a recombinant protein representing the central part of NS3-HCV genotype 1b, were used for in vitro stimulation of PBMC. Each group pooled 4–6 different 20-mer peptides which overlapped 8 amino acids. Groups 1, 2 and 3 included mainly core peptides with amino acid positions 5–80, 73–140 and 133–200, respectively (Table 1). Groups 4, 5 and 6 predominantly encompassed E1 peptides with amino acid positions 193–260, 253–332 and 325–392, respectively. Groups 7, 8 and 9 comprised E2/NS1 peptides with amino acid positions 427–494, 487–578 and 571–638, respectively. The two additional single peptides (NS1-7*, and NS1-5*) covered amino acids from 397 to 428 of the E2 sequence (Table 1). A fusion protein containing the NS3 sequence was expressed in *E. coli* and covered HCV amino acids 1188 to 1463 of the Belgian isolate IG8309.

Peptides were dissolved in the buffers shown in Table 1 and added to the cultures at a final concentration of 10 μg/ml. At this peptide concentration, the concentration of dissolving buffers in the cell cultures was not toxic or inhibitory. Preliminary experiments were performed to ascertain this. NS3 protein was used at a final concentration of 1.5 μg/ml. Tetanus toxoid (WHO, Copenhagen, Denmark), used as a positive control antigen, was added to the culture media at a final concentration of 10 μg/ml.

All the peptides were synthesized on either PepSyn K resin (Millipore) functionalized with the acid labile linker 4-(a-Fmoc-amino-2',4'-dimethoxybenzyl) phenoxyacetic acid, or TentaGel S-RAM resin (Rapp Polymere) functionalized with the same linker which yields peptide amides upon cleavage. t-Butyl-based side chain protection and Fmoc-a-amino protected amino acid derivatives were used. The guanidino group of arginine was 2,2,5,7,8-pentamethylchroman-6-sulfonyl-protected. The imidazole group of histidine was protected with either t-Boc or trityl and the sulfhydryl group of cysteine was protected with a trityl group. Couplings were carried out using preformed O-pentafluorophenyl esters except in the case of arginine where TBTU (O-(1H-benzotriazol-1-yl)-N,N,N',N',-tetramethyluronium tetrafluoroborate, Novabiochem) was used as the activating agent in the presence of 2 equivalents of the base N-methylmorpholine and 1 equivalent of 1-hydroxybenzotriazole. Occasionally, glutamine, asparagine, and tryptophan were also coupled using TBTU activation. In these cases, the trityl-protected derivatives of glutamine and asparagine (Millipore), and the t-Boc-protected derivative of tryptophan (Novabiochem) were used. All syntheses were carried out on a Milligen 9050 PepSynthesizer (Millipore) using continuous flow procedures. Following cleavage of the peptides with trifluoroacetic acid in the presence of appropriate scavengers and precipitation with diethylether, all peptides were analyzed by $C_{18}$-reverse phase chromatography.

HCV amino acid sequences corresponding to the viral nucleocapsid (core) and E1 proteins were based on the HC-J1 sequence described by Okamoto et al. (1990) Japan. J. Exp. Med. (1990) 60:167–177). HCV sequences starting at amino acid residue $Gly_{451}$ were taken from the sequences reported by Choo et al. (1991) Proc. Natl. Acad. Sci. USA (1991) 88:2451–2455. Most peptide sequences were chosen such that the peptides would overlap each other by 8 amino acid residues.

4.2. T Cell Proliferation Assays

The medium used for all cell cultures consisted of RPMI 1640 supplemented with 25 mM HEPES, 2 mM L-glutamine, 50 U/ml penicillin and 50 μg/ml streptomycin (all from Gibco Europe, Gent, Belgium), $5 \times 10^{-5}$ M 2-mercaptoethanol (Sigma, St. Louis, Mo.) and 10% heat-inactivated pooled human AB serum. This AB serum was obtained from healthy blood donors with blood group $AB^+$ and was only used when antibodies to HCV and HCV-RNA were absent. This "complemented" RPMI 1640 medium will hereafter be designated "complete medium".

PBMC were isolated from heparinized venous blood by isopycnic density centrifugation on Ficoll Hypaque (Lymphoprep, Nyegaard, Denmark) and suspended in complete medium. $4 \times 10^5$ PBMC in 200 μl of complete medium were cultured in 96 well round-bottomed microplates (Falcon Plastics) in the absence (unstimulated controls) or presence of varying concentrations of antigens for 5 days at 37° C. in an atmosphere of 5% $CO_2$ in air. 0.5 μCi ($^3$H)-thymidine was then added to each well and 16 to 20 h later the cultures were harvested onto glass fiber filters using a multichannel cell harvester (PHD, Cambridge, Mass.) to measure the incorporation of ($^3$H)-thymidine by liquid scintillation counting in an LKB-Wallac 8100 counter (LKB, Bromma, Sweden). Results are expressed as stimulation index (SI; mean cpm of antigen-stimulated cultures/mean cpm of control cultures). Proliferation was considered positive when stimulation index was >3. In some figures the results are expressed as cpm (mean cpm of antigen-stimulated cultures—mean cpm of control cultures). Standard deviations of the mean cpm of triplicate cultures were consistently below 10%.

The occurrence of in vivo primed HCV-specific memory T lymphocytes was examined using a lymphoproliferation assay. PBMC from 32 patients with chronic HCV were stimulated in vitro with pools of 4 to 6 partially overlapping, synthetic peptides representing the core, E1 and E2/NS1 regions of HCV type 1a, with 2 overlapping, single peptides from the amino-terminus of HCV type 1a and with a recombinant fusion protein containing the NS3 sequence of HCV type 1b. In all but 2 patients (#610 and #636) at least 2 and up to 11 (#633) assays were performed. In patient #632 for example lymphoproliferation was examined on 8 different occasions between week 4 and 54 following the start (week 0) of the Interferon therapy. FIG. 1 shows the results of these assays in correlation with the biochemical (ALT/AST) response to therapy. Four weeks after the start of Intron-A (Schering Plough) a normalization of the transaminase levels was observed. PBMC's from the patient consistently and vigorously proliferate upon stimulation with peptide pools 2 and 3. The responses to the other antigen preparations were less vigorous and less reproducible, suggesting that the number of memory cells recognizing these epitopes is lower. Antigens that did not induce a proliferative response with a stimulation index (SI) 3 at any time are not represented in the graph.

Figure 2:
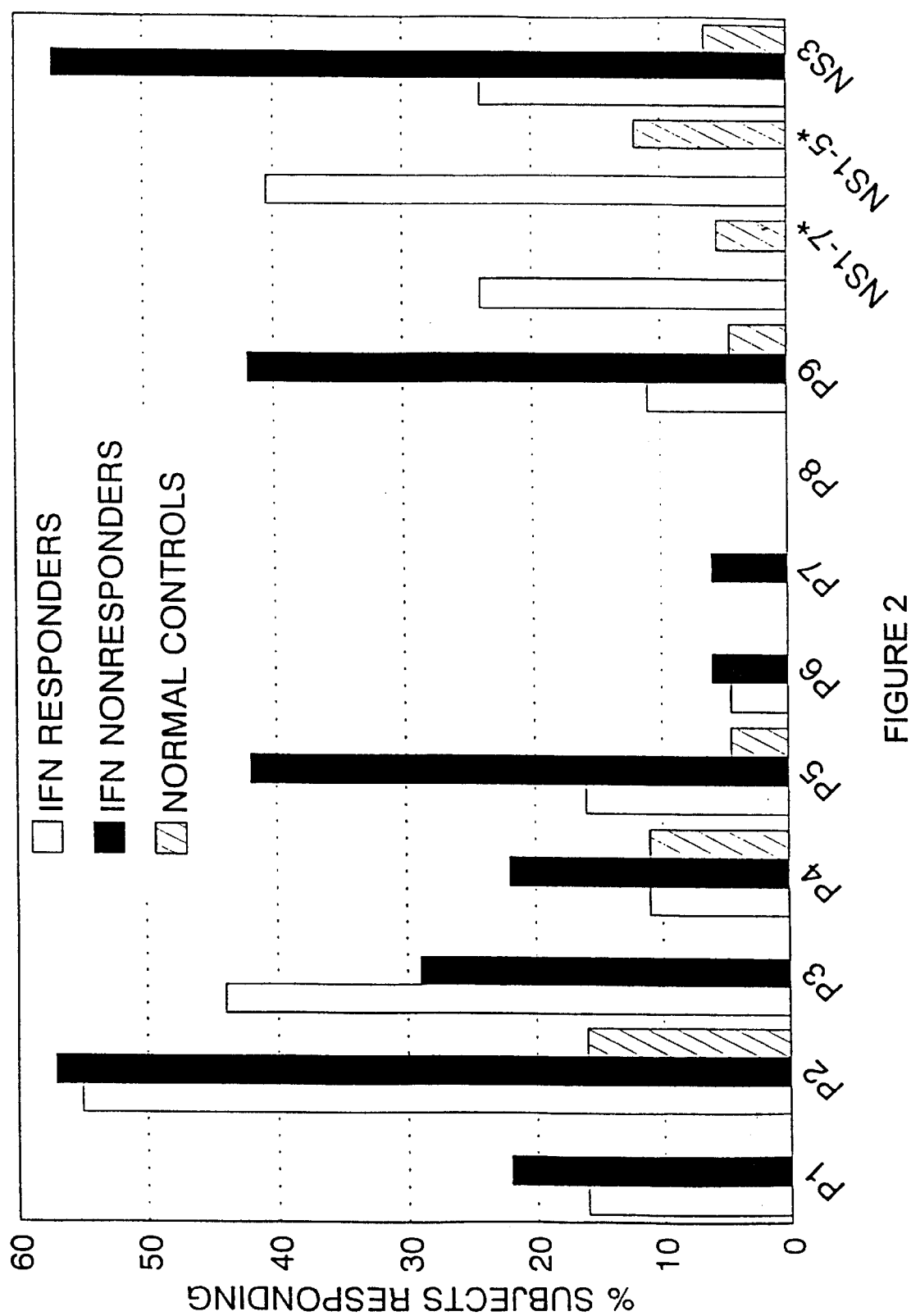
Figure 4C:
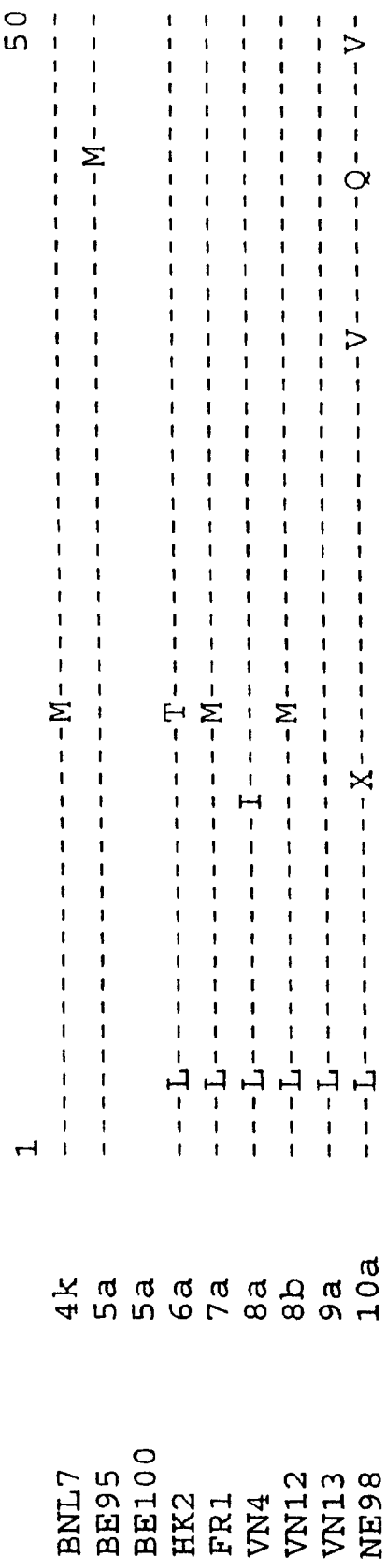
FIG. 4C represents an alignment of the HCV structural regions.

To analyze and summarize the results of 135 assays performed in the 32 HCV patients, we have chosen to consider the response of an individual patient to a particular antigen preparation (peptide pools 1 to 9, NS1–5*, NS1–7* or NS3 protein) as significant when it induces SI's 3 in at least half of the assays performed. The results shown in Table 4 have been obtained using this scoring method. The Table shows the antigen recognition pattern of chronic HCV patients towards the 12 antigen preparations standardly used. Apart from the individual patient number and the number of assays performed with PBMC's from each subject, Table 4 also shows the time frame wherein these assays were executed. The start of the Interferon therapy serves as the reference point, week 0. None of the patients responded to all the antigens. PBMC's from 13 of 18 (72%) clinical responders and 12 of 14 (85%) non-responders proliferated in response to at least one antigen preparation. All but one antigen preparation, peptide pool 8, induced a proliferative response in at least one subject. The most frequent responses were to peptide pools 2 and 3. Whereas both interferon-responders and non-responders proliferated equally well to peptide pool 2 (56% and 57%, respectively), non-responders reacted less well to peptide pool 3 (29% or 4 of 14) than responders (44% or 8 of 18). Similar imbalances were observed for the reactions to peptide pools 5 and 9, that were more frequently recognized by non-responders (43% and 43%, respectively) than by responders (17% and 11%, respectively). Clinical non-responders to interferon therapy also reacted more frequently (57% or 8 of 14) upon stimulation with the NS3 protein than responders (24% or 4 of 17). However, none of these differences in proliferative response rates to peptide pools 3, 5 and 9 or to NS3 protein reached statistical significance (p<0.05 in $^2$-test). A striking and significant difference (p=0.01 in $^2$-test) was observed for the response rate of responders and non-responders to peptides NS1–5* and NS1–7*. Indeed, 8 of 17 responders recognized one or both peptides while none of the non-responders did so. A summary of the results of all these proliferation assays is provided in FIG. 2, in which the response rates of the HCV patients as well as 18 healthy control subjects towards the 12 antigen preparations. Indeed, to establish the relevance of the proliferative responses observed in HCV patients, PBMC's from 18 healthy control subjects were stimulated with the same antigen preparations. Overall, 27 assays were performed: a single assay in 10 subjects, two in 7 volunteers and 3 in one individual. In 12 control subjects none of the antigens induced a proliferative response. In 6 subjects one or more antigens induced a proliferative response with an SI 3 in a unique assay or in at least half of the assays performed. Table 5 shows the antigens that induced the proliferation in these subjects. Although FIG. 2 suggests that proliferative responses occur more frequently in HCV patients than in healthy controls, these differences do not always reach statistical significance (p<0.05). Peptide pools 2 and 3 and the NS3 protein clearly (p<0.05) induce more frequent proliferative responses in the whole group of HCV patients than in healthy controls. Most of these differences are also significant when interferon responders and non-responders are each compared to the healthy control group. Only for the proliferative response to NS3 of interferon responders this is no longer valid. Although the frequency of proliferative response to peptide pool 5 in healthy controls and HCV patients were not significantly different, they turned out to be so (p<0.03) when only the non-responders were compared to the control subjects. All other differences did not reach the p<0.05 level.

Example 5

Fine Specificity of the Recognition of the HCV Core Region by PBMC from Clinical Responders: T Cell Epitope Localization in the Core Carboxyterminal Region Since peptide pools 2 and 3 elicited proliferative responses in a large fraction of HCV patients, we have examined which peptides from these pools were inducing these responses. The stimulatory capacity of single peptides on PBMC's from healthy control subjects was tested as well. Twenty-three proliferation assays were performed with PBMC's from 17 control subjects. Peptides core C17, core C21 and core C31 were recognized by 2, 1 and 1 subject or 12%, 6% and 6% of subjects, respectively. PBMC's were prepared from 11 HCV patients that responded to interferon therapy. Eight subjects had displayed a proliferative response to either one or both peptide pools 2 and 3, whereas 3 patients had not. Nineteen assays were performed. The scoring system for positive reactions was as described in example 4. Table 6 summarizes the results of these 19 assays and demonstrates the consistency of the assay results. Indeed, PBMC's from the patients that had not reacted to the peptide pools did not proliferate upon stimulation with any of the individual peptides. The PBMC's from the patients that had displayed a proliferative response before, also reacted upon stimulation with one or several peptides from these pools. At least one and up to five of these peptides were recognized by these patients. The most immunogenic region of the HCV core sequence seems to be located between amino acids 109 and 176. Peptides C27 (AA 157–176), recognized by 6 of the 8 proliferative responders, turns out to be the most immunodominant one, followed by C25 which is recognized by 5 patients, and C23 and C19 which are recognized by 3 subjects.

Example 6

The fine specificity of the lymphoproliferative responses was tested again with new samples, the majority of which was obtained from other patients than those analyzed in example 5. Five patients (two αIFN responders and three αIFN non-responders) and 16 normal controls were examined. Table 7 shows the results of the assays performed in chronic hepatitis C patients. The highest LPR observed in both αIFN responders tested was towards aa positions: 73–92 (C13); 109–128 (C19); 121–140 (C21); 145–164 (C25); 157–176 (C27). Only aa residues 121–140 (C21) and 133–152 (C23) elicited a high PLR in two αIFN non-responders. Therefore, the use of peptides C13, C19, C25 and/or C27 in prophylactic or therapeutic vaccine compositions may be particularly advantageous.

REFERENCES

Maertens, G., Ducatteeuw, A., Stuyver, L., Vandeponseele, P., Venneman, A., Wyseur, A., Bosman, F., Heijtink, R. & de Martynoff, G. (1994) Low prevalence of anti-E1 antibodies reactive to recombinant type 1b E1 envelope protein in type 2, 3, and 4 sera, but high prevalence in subtypes 1a and 1b. In: Viral Hepatitis and Liver Disease, Proceedings of the International Symposium on Viral Hepatitis and Liver Disease (Eds. Nishioka, K., Suzuki, H., Mishiro, S., and Oda, T.), pp 314–316, Springer-Verlag Tokyo.

Simmonds, P., Rose, K. A., Graham, S., Chan, S.-W., McOmish, F., Dow, B. C., Follett, E. A. C., Yap, P. L., & Marsden, H. (1993b) Mapping of serotype-specific, immunodominant epitopes in the NS4 region of hepatitis C virus (HCV): Use of type-specific peptides to serologically discriminate infections with HCV type 1, 2, and 3. *J. Clin. Microbiol.* 31, 1493–1503.

Simmonds, P., Holmes, E. C., Cha, T.-A., Chan, S.-W., McOmish, F., Irvine, B., Beall, E., Yap, P. L., Kolberg, J., & Urdea, M. S. (1993c) *J. Gen. Virol.* 74, 2391–2399.

Stuyver, L., Van Arnhem, W., Wyseur, A. & Maertens, G. (1994) Cloning and phylogenetic analysis of the Core, E2, and NS3/4 regions of hepatitis C virus type 5a. Biochem. Biophys. Res. Comm. 202, 1308–1314.

Simmonds, P., Alberti, A., Alter, H., Bonino, F., Bradley, D. W., Brechot, C., Brouwer, J., Chan, S.-W., Chayama K., Chen, D.-S., Choo, Q.-L., Colombo, M., Cuypers, T., Date, T., Dusheiko, G., Esteban, J. I., Fay, O., Hadziyannis, S., Han, J., Hatzakis, A., Holmes, E. C., Hotta, H., Houghton, M., Irvine, B., Kohara, M., Kolberg, J. A., Kuo, G., Lau, J. Y. N., Lelie, P. N., Maertens, G., McOmish, F., Miyamura, T., Mizokami, M., Nomoto, A., Prince A. M., Reesink, H. W., Rice, C., Roggendorf, M., Schalm, S., Shikata, T., Shimotohno, K., Stuyver, L., Trepo, C., Weiner, A., Yap, P. L. & Urdea, M. S. (1994) A proposed system for the nomenclature of hepatitis C virus genotypes. Hepatology 19, 1321–1324. Stuyver, L., Van Arnhem, W., Wyseur, A., DeLeys, R. & Maertens, G. (1993a) Analysis of the putative E1 envelope and NS4a epitope regions of HCV type 3. Biochem. Biophys. Res. Comm. 192, 635–641.

Stuyver, L., Rossau, R., Wyseur, A., Duhamel, M., Vanderborght, B., Van Heuverswyn, H. & Maertens, G. (1993b) Typing of hepatitis C virus isolates and characterization of new subtypes using a line probe assay. J. Gen Virol. 74, 1093–1102.

Stuyver, L., Wyseur, A., Van Arnhem, W., Rossau, R., Delaporte, E., Dazza, M.-C., Van Doorn, L.-J., Kleter, B. & Maertens, G. (1994a) The use of a line probe assay as a tool to detect new types or subtypes of hepatitis C virus. In: Viral Hepatitis and Liver Disease, Proceedings of the International Symposium on Viral Hepatitis and Liver Disease (Eds. Nishioka, K., Suzuki, H., Mishiro, S., and Oda, T.), pp 317–319, Springer-Verlag Tokyo.

Stuyver, L., Van Arnhem, W., Wyseur, A. & Maertens, G. (1994b) Cloning and Phylogenetic analysis of the Core, E2, and NS3/4 regions of the hepatitis C virus type 5a. Biochem. Biophys. Res. Comm. 202, 1308–1314.

Stuyver, L., Van Arnhem, W., Wyseur, A., Hernandez, F., Delaporte, E., & Maertens, G. (1994c) Classification of hepatitis C viruses based on phylogenetics analysis of the E1 and NS5B regions and identification of 5 new subtypes. Proc. Natl. Acad. Sci. USA 91, in press.

Knauf M, Bell D P, Hirtzer P, Luo Z, Young J, Katre N (1988) Relationship of effective molecular size to systemic clearance in rate of recombinant interleukin-2 chemically modified with water-soluble polymers. J Biol Chem.263: 15064–15070.

Poznansky M, Juliano R (1984) Biological approaches to the controlled delivery of drugs: a critical review. Pharmacol Rev.36: 277–336.

Szoka F Jr, Papahadjopoulos D (1980) Comparative properties and methods of preparation of lipid vesicles (liposomes). Annu-Rev-Biophys-Bioeng 9: 467–508.

Aurameas et al., Scand J Immunol, Vol. 8, Suppl. 7, 7–23 (1978).

Botarelli P, Brunetto M, Minutello M, Calvo P, Unutmaz D, Weiner A, Choo Q, Shuster J, Kuo G, Bonino F, Houghton M, Abrignani S (1993) T-lymphocyte response to hepatitis C virus in different clinical courses of infection. Gastroenterology 104: 580–587.

Bukh J, Purcell R, Miller R (1992). Sequence analysis of the 5' noncoding region of hepatitis C virus. Proc Natl Acad Sci USA 89:4942–4946.

Cha T, Beal E, Irvine B, Kolberg J, Chien D, Kuo G, Urdea M (1992) At least five related, but distinct, hepatitis C viral genotypes exist. Proc Natl Acad Sci USA 89:7144–7148.

Chan S, Simmonds P, McOmish F, Yap P, Mitchell R, Dow B, Follett E (1991) Serological responses to infection with three different types of hepatitis C virus. Lancet 338:1991.

Chan S, McOmish F, Holmes E, Dow B, Peutherer J, Follett E, Yap P, Simmonds P (1992) Analysis of a new hepatitis C virus type and its phylogenetic relationship to existing variants. J Gen Virol 73:1131–1141.

Choo Q, Richman K, Han J, Berger K, Lee C, Dong C, Gallegos C, Coit D, Medina-Selby A, Barr P, Weiner A, Bradley D, Kuo G, Houghton M (1991) Genetic organization and diversity of the hepatitis C virus. Proc Natl Acad Sci USA 88:2451–2455.

Davies G, Balard L, Schiffer E (1989) Treatment of chronic hepatitis with recombinant interferon alpha: a multicenter radomnized, controlled trial. N Engl Med 321: 1501–1506.

Erlanger, Method of Enzymology, 70: 85 (1980).

Gabizon A, Dagan A, Goren D, Barenholz Y, Fuks Z (1982) Liposomes as in vivo carriers of adriamycin: reduced cardiac uptake and preserved antitumor activity in mice. Cancer Res 42: 4734–4739.

Hoofnagle J, Lullen K, Jones D (1986) Treatment of chronic non-A, non-B hepatitis with recombinant human alpha interferon., N Engl J Med 315: 1575–1578.

Kato N, Hijikata M, Ootsuyama Y, Nakagawa M, Ohkoshi S, Sugimura T, Shimotohno K (1990) Molecular cloning of the human hepatitis C virus genome from Japanese patients with non-A, non-B hepatitis. Proc Natl Acad Sci USA 87: 9524–9528.

Koziel M, Dudley D, Wong J, Dienstag J, Houghton M, Ralston R, Walker B (1992). Intrahepatic cytotoxic T lymphocytes specific for hepatitis C virus in persons with chronic hepatitis. J Immunology 149: 3339–3344.

Minutello M, Pileri P. Unutmaz D, Censini S, Kuo G, Houghton M, Brunetto M, Bonino F. Abrignani S (1993). Compartimentalization of T lymphocytes to the site of disease: intrahepatic CD4+ T cells specific for the protein NS4 of Hepatitis C Virus in patients with Chronic hepatitis C. J Exp Med 178: 17–25.

Mori S, Kato N, Yagyu A, Tanaka T, Ikeda Y, Petchclai B, Chiewsilp P, Kurimura T, Shimotohno K (1992) A new type or hepatitis C virus in patients in Thailand. Biochem Biophys Res Comm 183: 334–342.

Okamoto H, Okada S, Sugiyama Y, Yotsumoto S, Tanaka T, Yoshizawa H, Tsuda F, Miyakawa Y, Mayumi M (1990). The 5' terminal sequence of the hepatitis C virus genome. Jap J Exp Med 60: 167–177.

Okamoto H, Okada S, Sugiyama Y, Kurai K, Iizuka H, Machida A, Miyakawa Y, Mayumi M (1991) Nucleotide sequence of the genomic RNA of hepatitis C virus isolated from a human carrier: comparison with reported isolates for conserved and divergent regions. J Gen Virol 72: 2697–2704.

Okamoto H, Kurai K, Okada S, Yamamoto K, Lizuka H, Tanaka T, Fukuda S, Tsuda F, Mishiro S (1992) Fulllength sequences of a hepatitis C virus genome having poor homology to reported isolates: comparative study of four distinct genotypes. Virology 188: 331–341.

Rodwell et al., Biotech 3, 889–894 (1985).

Stuyver L, Rossau R, Wyseur A, Duhamel M, Vanderborght B, Van Heuverswyn H, Maertens G (1993) Typing of hepatitis C virus (HCV) isolates and characterization of new (sub)types using a Line Probe Assay. J Gen Virology, 74: 1093–1102.

*Essential Immunoloy*, 3rd Ed., by Roit, published by Blackwell Scientific Publications; *Fundamentals of Clinical Immunology*, by Alexander and Good, published by W. B. Saunders; *Immunology*, by Bellanti, published by W. B. Saunders.

TABLE 1

Synthetic peptides used as antigens in the lymphoproliferative assays.

| HCV REGION | POOL | PEPTIDE NAME | AMINO ACID (AA) SEQUENCE | AA POSITION | SEQ ID NO | SOLVENT |
|---|---|---|---|---|---|---|
| CORE | 1 | CORE 2 | PKPQRKTKRNTNRRP | 5–19 | 1 | A |
| | | CORE 3 | RNTNRRPQDVKFPGGGQIVG | 13–32 | 2 | A |
| | | CORE 5 | PGGGQIVGGVYLLPRRGPRL | 25–44 | 3 | B |
| | | CORE 9 | TRKTSERSQPRGRRQPIPKV | 49–68 | 4 | A |
| | | CORE 11 | RRQPIPKVRRPEGRTWAQPG | 61–80 | 5 | A |
| | 2 | CORE 13 | GRTWAQPGYPWPLYGNEGCG | 73–92 | 6 | B |
| | | CORE 15 | LYGNEGCGWAGWLLSPRGSR | 85–104 | 7 | C |
| | | CORE 17 | LLSPRGSRPSWGPTDPRRRS | 97–116 | 8 | A |
| | | CORE 19 | PTDPRRRSRNLGKVIDTLTC | 109–128 | 9 | A |
| | | CORE 21 | KVIDTLTCGFADLMGYIPLV | 121–140 | 10 | D |
| | 3 | CORE 23 | LMGYIPLVGGAPLGGAARALA | 133–152 | 11 | A |
| | | CORE 25 | GGAARALAHGVRVLEDGVNY | 145–164 | 12 | A |
| | | CORE 27 | VLEDGVNYATGNLPGCSFSI | 157–176 | 13 | E |
| | | CORE 29 | LPGCSFSIFLLALLSCLTVP | 169–188 | 14 | O |
| | | CORE 31 | LLSCLTVPASAYQVRNSTGL | 181–200 | 15 | C |
| E1 | 4 | E1-33 | QVRNSTGLYHVIDNCPNSSI | 193–212 | 16 | O |
| | | E1-35 | NDCPNSSIVYEAHDAILHTP | 205–224 | 17 | C |
| | | E1-37 | HDAILHTPGCVPCVREGNVS | 217–236 | 18 | A |
| | | E1-39 | CVREGNVSRCWVAMTPTVAT | 229–248 | 19 | H |
| | | E1-41 | AMTPTVATRDGKLPPATQLRR | 241–260 | 20 | A |
| | 5 | E1-43 | LPATQLRRHIDLLVGGSATLC | 253–272 | 21 | H |
| | | E1-45 | LVGSATLCSALYVGDLCGSV | 265–284 | 22 | E |
| | | E1-49 | QLFTFSPRRHWTTQGCNCSE | 289–308 | 23 | H |
| | | E1-51 | TQGGCNCSIYPGHTTGHRMAW | 301–320 | 24 | B |
| | | E1-53 | TTGHRMAWDMMMNWSPTAAL | 313–332 | 25 | H |
| | 6 | E1-55 | NWSPTAALVMAQLLRIPQAI | 325–344 | 26 | H |
| | | E1-57 | LLRIPQAILDMIAGAHWGVL | 337–356 | 27 | H |
| | | E1-59 | AGAHWGVLAGIAYFSMVGNW | 349–368 | 28 | I |
| | | E1-63 | VVLLLFAGVDETTVSGGQA | 373–392 | 29 | E |
| E2/NS1 | 7 | NS1-3* | LNCNESLNTGWWLAGLIYQHK | 427–446 | 30 | C |
| | | NS1-1* | AGLIYQHKFNSSGCPERLAS | 439–458 | 31 | B |
| | | NS1-1 | GCPERLASCRPLTDFDQGWG | 451–470 | 32 | B |
| | | NS1-3 | TDFDQGWGPISYANGSGFDQ | 463–482 | 33 | A |
| | | NS1-5 | ANGSGPDQRPYCWHYPPKPC | 475–494 | 34 | A |
| | 8 | NS1-7 | WHYPPKPCGIVPAKSVCGPV | 487–506 | 35 | B |
| | | NS1-9 | AKSVCGPVYCFTPSPVVVGT | 499–518 | 36 | O |
| | | NS1-11 | PSPVVVGTTDRSGAPTYSWG | 511–530 | 37 | C |
| | | NS1-13 | GAPTYSWGENDTDVFVLNNT | 523–542 | 38 | E |
| | | NS1-17 | GNWFGCTWNMSTGFTKVCGA | 547–566 | 39 | O |
| | | NS1-19 | GFTKVCGAPPVCIGGAGNNT | 559–578 | 40 | A |
| | 9 | NS1-21 | IGGAGNNTLHCPTDCFRKHP | 571–590 | 41 | A |
| | | NS1-23 | TDCFRKHPDATYSRCGSGPW | 583–602 | 42 | A |
| | | NS1-25 | SRCGSGPWTTPRCLVDYPYR | 595–614 | 43 | B |
| | | NS1-27 | CLVDYPYRLWHYPCTINYTI | 607–626 | 44 | C |
| | | NS1-29 | PCTINYTIFKIRMYVGGVEH | 619–638 | 45 | A |
| | | NS1-7* | SGLVSLFTPGAKQNIQLINT | 397–416 | 46 | C |
| | | NS1-5* | QNIQLINTNGSWHINSTALN | 409–428 | 47 | C |

Solvents used:
Solvent A: 0.1% trifluoroacetic acid; Solvent B: 0.1% trifluoroacetic acid, 25% acetonitrile; Solvent C: 0.1% trifluoroacetic acid, 30% acetonitrile; Solvent D: 0.1% trifluoroacetic acid, 50% acetonitrile; Solvent E: 0.005 ammonia buffer; Solvent O: 50% dimethyl sulfoxide; Solvent H: 0.1% trifluoroacetic acid, 40% acetonitrile.

TABLE 2

General data from HCV patients.

| Patient | Gender | Age | AP Diagnosis | Source | Duration (Years) | Genotype | IFN Scheme | ALT before therapy |
|---|---|---|---|---|---|---|---|---|
| CLINICAL RESPONDERS | | | | | | | | |
| 604 | F | 30 | CAH: mod | IVDA | 10 | 1b | 2 | 150 |
| 607 | M | 39 | CPH | Unknown | 2 | 1b | 1 | 182 |
| 608 | M | 61 | CAH: mild | Transfusion | 7 | 3a | 1 | 196 |
| 610 | F | 27 | Non spec | Unknown | 2 | 1b | 2 | 219 |
| 614 | M | 56 | CAH: mild | Transfusion | 10 | 1b | 2 | 425 |
| 615 | M | 71 | CAH: mod | Unknown | 2 | 1b | 1 | 201 |
| 616 | F | 52 | Non spec | Transfusion | 5 | 1b | 1 | 152 |
| 618 | F | 37 | CPH | Needle stick | 5 | 1b | 2 | 60 |
| 621 | M | 48 | CAH: mod | Unknown | 8 | 1b | 1 | 63 |
| 624 | M | 31 | CPH | Needle stick | 15 | 1b | 2 | 158 |

TABLE 2-continued

General data from HCV patients.

| Patient | Gender | Age | AP Diagnosis | Source | Duration (Years) | Genotype | IFN Scheme | ALT before therapy |
|---|---|---|---|---|---|---|---|---|
| 626 | F | 34 | CAH: sev | Transfusion | 6 | 3a | 2 | 168 |
| 630 | M | 30 | CPH | Needle stick | 5 | 1b | 2 | 9 |
| 632 | M | 57 | CPH | Unknown | 1 | 4a or 5a | 2 | 359 |
| 633 | F | 30 | CAH: mod | Transfusion | 2 | 1b | 2 | 292 |
| 634 | F | 67 | CAH: mod | Unknown | 32 | 1b | 2 | 481 |
| 635 | F | 47 | prob cirrh | Transfusion | 14 | 1b | 2 | 100 |
| 636 | F | 54 | CAH: mod | Unknown | 7 | 5a | 1 | 90 |
| 639 | F | 62 | CAH | Transfusion | 32 | 1b | 1 | 79 |
| CLINICAL NON-RESPONDERS | | | | | | | | |
| 601 | M | 32 | CAH: mod | Transfusion | 3 | 1b | 2 | 141 |
| 602 | M | 66 | CAH: mod | Transfusion | 3 | 1b | 1 | 349 |
| 603 | M | 45 | CAH: sev | Transfusion | 17 | 1b | 2 | 157 |
| 606 | F | 53 | CAH: mod | Unknown | 2 | 1b | 1 | 299 |
| 611 | M | 51 | CPH | Transfusion | 7 | 1b | 1 | 195 |
| 613 | F | 38 | CAH: mod | IVDA | 17 | 3a | 1 | 178 |
| 617 | M | 71 | CAH: sev | Transfusion | 3 | 1b | 1 | 447 |
| 620 | M | 67 | CAH: mod | Unknown | 2 | 1b | 1 | 138 |
| 622 | M | 40 | CAH: sev | Transfusion | 11 | 1b | 1 | 291 |
| 625 | M | 70 | CAH: mod | Unknown | 1 | 1b | 1 | 134 |
| 627 | M | 44 | CAH: mod | IVDA | 8 | 3a | 1 | 254 |
| 629 | F | 61 | Cirrh | Transfusion | 11 | 1b | 1 | 179 |
| 631 | M | 69 | CPH | Unknown | 5 | 1b | 2 | 358 |
| 637 | F | 59 | Cirrh | Unknown | 5 | 1b | 2 | 118 |

CAH = CHRONIC ACTIVE HEPATITIS.
CPH = CHRONIC PERSISTENT HEPATITIS.
CIRRH = CIRRHOSIS.
NON SPEC = NOT DONE OR NOT SPECIFIC ABNORMALITIES

TABLE 3

Antibody reactivities to 6 HCV antigens of the Line Immuno-Assay in 32 chronic HCV patients.

CLINICAL RESPONDERS

| Patient | Weeks | Genotype | NS4 | NS5 | C1 | C2 | C3 | C4 |
|---|---|---|---|---|---|---|---|---|
| 604 | −6 | 1b | 3 | 3 | 2 | 2 | — | — |
|  | 90 |  | 3 | 3 | 3 | 3 | — | 2 |
| 607 | −11 | 1b | 2 | 3 | 2 | — | — | — |
|  | 84 |  | 3 | 3 | 3 | — | — | — |
| 608 | −6 | 3a | — | 3 | — | — | — | — |
| 610 | −6 | 1b | 3 | — | 2 | 3 | — | — |
| 614 | 30 | 1b | 3 | 3 | 2 | 2 | — | — |
|  | 60 |  | 2 | 3 | 3 | 3 | — | — |
| 615 | −2 | 1b | 3 | — | — | 2 | — | — |
| 616 | −6 | 1b | 3 | — | 2 | 3 | 2 | 2 |
| 618 | −6 | 1b | — | — | — | 3 | — | — |
|  | 54 |  | — | — | — | 2 | — | — |
| 621 | −3 | 1b | 3 | 3 | 2 | — | — | — |
|  | 30 |  | 3 | 3 | 2 | — | — | — |
| 624 | −5 | 1b | 3 | 3 | 2 | 2 | — | — |
|  | 20 |  | 3 | 3 | 2 | 3 | 2 | 2 |
| 626 | 2 | 3a | — | 2 | 2 | 3 | — | — |
|  | 20 |  | 2 | 2 | 3 | 3 | — | 2 |
| 630 | −12 | 1b | 3 | — | 2 | 2 | — | — |
|  | 8 |  | 3 | — | 2 | 2 | — | — |
| 632 | −6 | 4a or 5a | — | 3 | 2 | 3 | 2 | 2 |
|  | 8 |  | — | 3 | 2 | 3 | 2 | 2 |
| 633 | −6 | 1b | 3 | 3 | — | 2 | — | 2 |

"—" denotes negative, indeterminate or weak reactions. 2, moderate reaction. 3, strong reaction.

TABLE 4

T-cell recognition of 12 HCV antigens in 32 chronic hepatitis C patients under alpha-interferon therapy.

| Patient | Genotype | N°. Assays | Time of assays | P1 | P2 | P3 | P4 | P5 | P6 | P7 | P8 | P9 | NSI-7* | NSI-5* | NS3 |
|---|---|---|---|---|---|---|---|---|---|---|---|---|---|---|---|
| CLINICAL RESPONDERS | | | | | | | | | | | | | | | |
| 604 | 1b | 2 | w90–108 |  | + | + | + | + | + |  | + | + | + | + | + |
| 607 | 1b | 2 | w84–120 |  | + |  |  | + |  |  |  | + | ND | ND | ND |
| 608 | 3a | 2 | w90–108 |  | + | + |  |  |  |  |  |  |  |  |  |
| 610 | 1b | 1 | w84 |  |  |  |  |  |  |  |  |  |  |  |  |
| 614 | 1b | 4 | w60–108 |  |  |  |  |  |  |  |  |  |  | + |  |
| 615 | 1b | 2 | w66–84 | + | + | + | + | + |  |  |  |  |  |  | + |

TABLE 4-continued

T-cell recognition of 12 HCV antigens in 32 chronic hepatitis C patients under alpha-interferon therapy.

| Patient | Genotype | N°. Assays | Time of assays | P1 | P2 | P3 | P4 | P5 | P6 | P7 | P8 | P9 | NSI-7* | NSI-5* | NS3 |
|---|---|---|---|---|---|---|---|---|---|---|---|---|---|---|---|
| 616 | 1b | 3 | w78–108 | | | | | | | | | | | + | |
| 618 | 1b | 4 | w54–84 | + | + | | | | | | | | | | + |
| 621 | 1b | 4 | w30–60 | | | + | | | | | | | + | + | |
| 624 | 1b | 9 | w20–90 | | | | | | | | | | | | |
| 626 | 3a | 9 | w16–60 | | + | + | | | | | | | + | | |
| 630 | 1b | 6 | w8–75 | | | | | | | | | | | | |
| 632 | 4a or 5a | 8 | w4–54 | | + | + | | | | | | | | | |
| 633 | 1b | 11 | w0–48 | | | | | | | | | | | | |
| 634 | 1b | 3 | w0–24 | | + | | | | | | | | + | + | |
| 635 | 1b | 7 | w-6–54 | | | | | | | | | | | | |
| 636 | 5a | 1 | w24 | | + | + | | | | | | | + | | |
| 639 | 1b | 4 | w-3–19 | + | + | + | | | | | | | + | + | |
| CLINICAL NON-RESPONDERS ||||||||||||||||
| 601 | 1b | 4 | w90–140 | | + | | | + | + | | + | | | + | |
| 602 | 1b | 2 | w96–108 | + | + | + | + | | | | + | | | + | |
| 603 | 1b | 2 | w78–93 | | + | + | + | + | | | | | | + | |
| 606 | 1b | 3 | w84–96 | | + | | | + | | | | | | + | |
| 611 | 1b | 2 | w66–84 | + | + | | | + | | | | | | | |
| 613 | 3a | 8 | w60–96 | | | | | | | | | | | + | |
| 617 | 1b | 5 | w60–108 | | | | | | | | | | | | |
| 620 | 1b | 3 | w42–66 | | | | | | | | + | | | + | |
| 622 | 1b | 3 | w30–54 | | | | | + | | | | | | + | |
| 625 | 1b | 4 | w20–66 | | + | + | | | | | + | | | | |
| 627 | 3a | 3 | w16–24 | | + | | | | | | + | | | | |
| 629 | 1b | 2 | w20–48 | + | + | | + | + | | + | + | | | + | |
| 631 | 1b | 5 | w4–w16 | | | | | | | | | | | | |
| 637 | 1b | 7 | w-6–16 | | | + | | | | | | | | | |

P1-3 corresponds to Core, P4-6 represents E1. P7-9 comprises E2/NS1. (+) denotes lymphoproliferative response. ND-Not done.

TABLE 5

Antigens recognized by 6 control subjects displaying significant * lymphoproliferation responses.

| SUBJECTS | N° ASSAYS | P1 | P2 | P3 | P4 | P5 | P6 | P7 | P8 | P9 | NS1–7* | NS1–5* | NS3 |
|---|---|---|---|---|---|---|---|---|---|---|---|---|---|
| CAE | 3 | | | | | | | | + | | | | |
| IDS | 1 | | + | | | | | | | | | | + |
| LCE | 1 | | | | | | | | | | | + | |
| MVH | 1 | | + | | + | + | | | + | | | + | |
| PDG | 2 | | | | + | | | | | | | | |
| RDB | 2 | | + | | | | | | | | | | |

*A response is considered significant when a S.I. equal or greater than 3 in a single peptide assay or in at least half of the assays performed.

TABLE 6

The lymphoproliferative responses to peptide pools are consistent with lymphoproliferative responses to single peptides fr.

| | | PEPTIDE POOLS | | | | | | SINGLE PEPTIDES | | | | | | |
| | Patient | N° assays | Pool 2 | Pool 3 | N° assays | C13 | C15 | P2 C17 | C19 | C21 | C23 | C25 | P3 C27 | C29 | C31 |
|---|---|---|---|---|---|---|---|---|---|---|---|---|---|---|---|
| LPR TO POOLS 2 AND/OR 3 | 604 | 2 | + | + | 1 | − | − | − | − | − | + | − | − | − | − |
| | 615 | 2 | + | + | 1 | − | − | − | − | − | + | − | + | − | − |
| | 618 | 4 | + | − | 1 | − | − | − | − | − | − | + | + | − | − |
| | 621 | 4 | − | + | 1 | − | − | − | − | − | − | + | + | − | − |
| | 626 | 9 | + | + | 5 | − | − | − | − | − | − | + | + | − | − |
| | 632 | 8 | + | + | 4 | − | − | − | + | + | + | + | + | − | − |
| | 634 | 2 | + | − | 1 | − | − | − | + | − | − | − | + | − | − |
| | 639 | 4 | + | + | 2 | − | − | − | + | − | − | + | − | − | + |
| NO LPR TO POOLS 2 AND 3 | 614 | 3 | − | − | 1 | − | − | − | − | − | − | − | − | − | − |
| | 616 | 3 | − | − | 1 | − | − | − | − | − | − | − | − | − | − |
| | 633 | 1 | − | − | 1 | − | − | − | − | − | − | − | − | − | − |

TABLE 7

Fine specificity of T-cell recognition of P2 and P3 Core individual peptides.

| Patient N° | Clinical response to αIFN[a] | Week[b] | Blank[c] | TT[d] | P2 peptides | | | | | P3 peptides | | | | |
|---|---|---|---|---|---|---|---|---|---|---|---|---|---|---|
| | | | | | C13[e] | C15 | C17 | C19 | C21 | C23 | C25 | C27 | C29 | C31 |
| 626 | R | 14 | 750 | 14.5 | 4.4 | — | — | — | 3.3 | — | 6 | 8.2 | — | — |
| 636 | R | 28 | 1032 | 3.6 | 6.3 | — | — | 7.1 | — | — | 9.7 | 5.8 | — | — |
| 620 | NR | 20 | 5047 | 4.1 | ND[f] | ND | ND | ND | ND | 4.1 | — | — | — | — |
| 627 | NR | 54 | 928 | 19.1 | — | — | — | — | 3.6 | — | — | — | — | — |
| 637 | NR | 45 | 2370 | 4.2 | — | — | — | — | — | — | — | — | — | — |

[a]R: responder; NR: Not responder.
[b]Time points of αIFN therapy on which LPA were performed.
[c]Values express cpm.
[d]TT: Tetanus toxoid. Values denote SI.
[e]C13–C21 and C23–C31 are the individual peptides of P2 and P3 Core peptide pools. Only SI equal or greater than 3 are shown.
[f]ND: Not done.

What is claimed is:

1. An isolated peptide consisting of SEQ ID NO: 57.

2. An isolated peptide consisting of the an amino acid sequence selected from the group consisting of SEQ ID NOs: 135–147 and 149–162.

3. An isolated peptide consisting of at least 8 to at most 20 contiguous amino acids of a sequence selected from the group consisting of SEQ ID NOs: 135–147, 149 and 152–162.

4. An HCV immunogenic composition comprising a peptide of claim 1 and a pharmaceutically acceptable excipient.

5. A method of inducing a specific T cell function comprising administering to a person a peptide according to claim 1, in an amount sufficient to induce T cell activity.

6. An HCV immunogenic composition comprising a peptide of claim 2 and a pharmaceutically acceptable excipient.

7. A method of inducing a specific T cell function comprising administering to a person an isolated peptide according to claim 2, in an amount sufficient to induce T cell activity.

8. An HCV immunogenic composition comprising a peptide of claim 3 and a pharmaceutically acceptable excipient.

9. A method of inducing a specific T cell function comprising administering to a person a peptide according to claim 3, in an amount sufficient to induce T cell activity.

10. A polypeptide sequence comprising a peptide according to any one of claims 1, 2 and 3 and at least one flanking amino acid sequence consisting of a non-HCV amino acid sequence.

11. An HCV immunogenic composition comprising a polypeptide of claim 10 and a pharmaceutically acceptable excipient.

12. A method of inducing a specific T cell function comprising administering to a person a polypeptide according to claim 10, in an amount sufficient to induce T cell activity.

13. A composition comprising at least one of polypeptide of claim 10, and a pharmaceutically acceptable excipient.

14. A method of treating a person infected with HCV comprising administering a composition of claim 13 to said person.

15. A polypeptide sequence comprising a peptide according to any one of claims 1, 2 and 3 and at least one flanking peptide sequence consisting of a peptide sequence which is not a natural contiguous HCV amino acid sequence.

16. An HCV immunogenic composition comprising a polypeptide of claim 15 and a pharmaceutically acceptable excipient.

17. A method of Inducing a specific T cell function comprising administering to a person a polypeptide according to claim 15, in an amount sufficient to induce T cell activity.

18. A composition comprising at least one of polypeptide of claim 15, and a pharmaceutically acceptable excipient.

19. The peptide according to any one of claims 1, 2 and 3, comprising a CTL cell epitope.

20. An HCV immunogenic composition comprising a peptide of claim 19 and a pharmaceutically acceptable excipient.

21. A method of inducing a specific T cell function comprising administering to a person a peptide according to claim 19, in an amount sufficient to induce T cell activity.

22. The peptide according to any one of claims 1, 2 and 3, comprising a T cell helper epitope.

23. An HCV immunogenic composition comprising a peptide of claim 22 and a pharmaceutically acceptable excipient.

24. A method of inducing a specific T cell function comprising administering to a person a peptide according to claim 22, in an amount sufficient to induce T cell activity.

25. A composition comprising at least one peptide of claims 1, 2 and 3, and a pharmaceutically acceptable excipient.

26. A method of inducing a specific T cell function comprising administering to a person a composition according to claim 25, in an amount sufficient to induce T cell activity.

27. A method of treating a person infected with HCV comprising administering a composition of claim 25 to said person.

28. A method of immunizing a person comprising administering to said person a composition according to claim 25, wherein said peptide contains a T-cell stimulating epitope.

29. A polypeptide sequence comprising a peptide according to any one of claims 1, 2 and 3 and at least one flanking amino acid consisting of a non-HCV amino acid.

30. A composition comprising at least one of polypeptide of claim 29, and a pharmaceutically acceptable excipient.

31. A method of inducing a specific T cell function comprising administering to a person a composition according to claim 30, in an amount sufficient to induce T cell activity.

32. A method of treating a person infected with HCV comprising administering a composition of claim 30 to said person.

33. A method of immunizing a person comprising administering to said person a composition according to claim 30, wherein said peptide contains a T-cell stimulating epitope.

34. A polypeptide sequence comprising a peptide according to any one of claims 1, 2 and 3 and at least one flanking amino acid consisting of an amino acid which is not a natural contiguous HCV amino acid.

35. A composition comprising at least one of polypeptide of claim 34, and a pharmaceutically acceptable excipient.

36. A method of inducing a specific T cell function comprising administering to a person a composition according to claim 35, in an amount sufficient to induce T cell activity.

37. A method of treating a person infected with HCV comprising administering a composition of claim 35 to said person.

38. A method of immunizing a person comprising administering to said person a composition according to claim 35, wherein said peptide contains a T-cell stimulating epitope.

39. A method of inducing a specific T cell function comprising administering to a person a polypeptide consisting of at least 8 to at most 278 contiguous amino acids of the amino acid sequence represented by SEQ ID NO 57, in an amount sufficient to induce T cell activity and said contiguous amino acids containing a T cell-stimulating epitope.

40. An isolated peptide consisting of at least 8 to at most 15 contiguous amino acids of SEQ ID NO:57, wherein an amino acid sequence selected from the group consisting of SEQ ID NOs: 150 and 151 is present in said peptide.

41. An isolated peptide consisting of at least 8 to at most 20 contiguous amino acids of SEQ ID NO:57, wherein SEQ ID NO: 155 is present in said peptide.

42. An isolated peptide consisting of at least 8 to at most 25 contiguous amino acids of SEQ ID NO:57, wherein at least one amino acid sequence selected from the group consisting of SEQ ID NOs: 149, 158, and 159 is present in said peptide.

43. An isolated peptide consisting of at least 8 to at most 30 contiguous amino acids of SEQ ID NO:57, wherein at least one amino acid sequence selected from the group consisting of SEQ ID NOs: 139, 142, 143, 144, 145, 146, 156, and 157, is present in said peptide.

44. An isolated peptide consisting of at least 8 to at most 80 contiguous amino acids of the peptide of SEQ ID NO:57, wherein at least one peptide selected from the group consisting of SEQ ID NOs: 140 and 162, is present in said peptide.

45. An isolated peptide consisting of at least 8 to at most 278 contiguous amino acids of SEQ ID NO:57, wherein said peptide includes at least one amino acid sequence selected from the group consisting of SEQ ID NOs: 135, 136, 137, 138, 141, 147, 152, 153, 154, 160 and 161.

46. An isolated peptide consisting of at least 9 to at most 25 contiguous amino acids of SEQ ID NO:57, wherein said peptide includes SEQ ID NO:148.

47. A polypeptide sequence comprising a peptide according to any one of claims 39–46 and at least one flanking amino acid sequence consisting of a non-HCV amino acid sequence.

48. A polypeptide sequence comprising a peptde according to any one of claims 39–46 and at least one flanking peptide sequence consisting of a peptide sequence which is not a natural contiguous HCV amino acid sequence.

49. A polypeptide sequence comprising a peptide according to any one of claims 39–46 and at least one flanking amino acid consisting of a non-HCV amino acid.

50. A composition comprising at least one of polypeptide of claim 49, and a pharmaceutically acceptable excipient.

51. A method of inducing a specific T cell function comprising administering to a person a composition according to claim 50, in an amount sufficient to induce T cell activity.

52. A method of treating a person infected with HCV comprising administering a composition of claim 50 to said person.

53. A method of immunizing a person comprising administering to said person a composition according to claim 30, wherein said peptide contains a T-cell stimulating epitope.

54. A method of inducing a specific T cell function comprising administering to a person a polypeptide according to claim 49, in an amount sufficient to induce T cell activity.

55. An HCV immunogenic composition comprising a polypeptide of claim 49, and a pharmaceutically acceptable carrier.

56. A polypeptide sequence comprising a peptide according to any one of claims 39–46 and at least one flanking amino acid consisting of an amino acid which is not a natural contiguous HCV amino acid.

57. A composition comprising at least one of polypeptide of claim 56, and a pharmaceutically acceptable excipient.

58. A method of inducing a specific T cell function comprising administering to a person a composition according to claim 57, in an amount sufficient to induce T cell activity.

59. A method of treating a person infected with HCV comprising administering a composition of claim 57 to said person.

60. A method of immunizing a person comprising administering to said person a composition according to claim 57, wherein said peptide contains a T-cell stimulating epitope.

61. A method of inducing a specific T cell function comprising administering to a person a polypeptide according to claim 56, in an amount sufficient to induce T cell activity.

62. An HCV immunogenic composition comprising a polypeptide of claim 56, and a pharmaceutically acceptable carrier.

63. A composition comprising at least one of pypeptide of claims 39–46, and a pharmaceutically acceptable excipient.

64. A method of immunizing a person comprising administering to said person a composition according to claim 63, wherein said peptide contains a T-cell stimulating epitope.

65. A method of inducing a specific T cell function comprising administering to a person at least one peptide according to claims 39–46, in an amount sufficient to induce T cell activity.

66. An HCV immunogenic composition comprising a polypeptide of any one of claims 39–46, and a pharmaceutically acceptable carrier.

* * * * *

UNITED STATES PATENT AND TRADEMARK OFFICE
CERTIFICATE OF CORRECTION

PATENT NO.    : 6,689,368 B1
DATED         : February 10, 2004
INVENTOR(S)   : Leroux-Roels et al.

It is certified that error appears in the above-identified patent and that said Letters Patent is hereby corrected as shown below:

Column 1,
Line 5, delete "pending" and insert therefor -- now U.S. Patent No. 6, 555,114 --.

Column 2,
Line 31, delete "(in" and insert therefor -- in --.

Column 3,
Line 43, delete "any." and insert therefor -- any --.

Column 4,
Line 3, delete "of a" and insert therefor -- of --.

Column 5,
Line 47, delete "understod" and insert therefor -- understood --.

Column 6,
Line 12, delete "lenght" and insert therefor -- length --.
Line 14, delete "al" and insert therefor -- at --.
Line 53, delete "and", first occurrence,-- and-insert therefor -- to --.

Column 7,
Line 3, delete "to a" and insert therefor -- to `a --.
Line 4, delete "protein" and insert therefor -- protein' --.
Line 33, in SEQ ID NO 58, delete "$X_{26}$PGCSFSI" and insert therefor -- $X_{36}$PGCSFSI --.
Line 38, delete "X8" and insert therefor -- $X_8$ --.

Column 8,
Line 47, delete "about" and insert therefor -- about 20 --.

Column 9,
Line 21, delete "Preferern-" and insert therefor -- Preferen- --.

Column 11,
Line 14, delete "ASPCWVAM" and insert therefor -- ASRCWVAM --.

Column 13,
Line 66, in SEQ ID NO 108, delete "$NH_2$-I$X_{55}X_{56}X_{57}X_{58}X_{59}X_{60}Z_1Z_2LX_{61}$CPTDCFR" and insert therefor -- $NH_2$-I$X_{55}X_{56}X_{57}X_{58}NX_{59}X_{60}Z_1Z_2LX_{61}$CPTDCFR --.

UNITED STATES PATENT AND TRADEMARK OFFICE
CERTIFICATE OF CORRECTION

PATENT NO. : 6,689,368 B1
DATED : February 10, 2004
INVENTOR(S) : Leroux-Roels et al.

It is certified that error appears in the above-identified patent and that said Letters Patent is hereby corrected as shown below:

Column 15,
Line 28, delete ", ASRCW-".
Line 29, delete "VAM".
Line 50, delete "fro" and insert therefor -- for --.

Column 17,
Line 15, delete "*oerfrincens*" and insert therefor -- *perfringens* --.
Line 20, delete "encephalomyeitis" and insert therefor -- encephalomyelitis --.
Line 21, delete "chloera" and insert therefor -- cholera --.

Column 20,
Line 25, delete "Most" and insert therefor -- Almost --.

Column 21,
Line 26, delete "dexErose" and insert therefor -- dextrose --.

Column 22,
Line 15, delete "paricles" and insert therefor -- particles --.

Column 24,
Line 64, delete "ECV" and insert therefor -- HCV --.

Column 29,
Line 15, delete "Stuyver, L., Van Arnhem, W., Wyseur, A.,"
Line 16, insert "Stuyver, L., Van Arnhem, W., Wyseur, A.,"

Columns 31/32, Table 1,
amino acid sequence of peptide E1-33, delete "QVRNSTGLYHVIDNCPNSSI" and insert therefor -- QVRNSTGLYHVTNDCPNSSI --.
amino acid sequence of peptide E1-43, delete "LPATQLRRHIDLLVGGSATLC" and insert therefor -- LPATQLRRHIDLLVGSATLC --.
amino acid sequence of peptide E1-49, delete "QLFTFSPRRHWTTQGCNCSE" and insert therefor -- QLFTFSPRRHWTTQGCNCSI --.
amino acid sequence of peptide E1-51, delete "TQGGCNCSIYPGHTTGHRMAW" and insert therefor -- TQGCNCSIYPGHITGHRMAW --.
amino acid sequence of peptide E1-53, delete "TTGHRMAWDMMMNWSPTAAL" and insert therefor -- ITGHRMAWDMMMNWSPTAAL --.
amino acid sequence of peptide E1-63, delete "VVLLLFAGVDETTVSGGQA" and insert therefor -- VVLLLFAGVDAETIVSGGQA --.

UNITED STATES PATENT AND TRADEMARK OFFICE
CERTIFICATE OF CORRECTION

PATENT NO. : 6,689,368 B1
DATED : February 10, 2004
INVENTOR(S) : Leroux-Roels et al.

It is certified that error appears in the above-identified patent and that said Letters Patent is hereby corrected as shown below:

Columns 31/32, Table 1 (cont'd),
amino acid sequence of peptide NS1-3, delete "TDFDQGWGPISYANGSGFDQ" and insert therefor -- TDFDQGWGPISYANGSGPDQ --.
amino acid sequence of peptide NS1-17, delete "GNWFGCTWNMSTGFTKVCGA" and insert therefor -- GNWFGCTWMNSTGFTKVCGA --.
amino acid sequence of peptide NS1-25, delete "SRCGSGPWTTPRCLVDYPYR" and insert therefor -- SRCGSGPWITPRCLVDYPYR --.

Columns 33/34,
Table 4, delete "NSI-7*" and insert therefor -- NS1-7*--.
Table 4, delete "NSI-5*" and insert therefor -- NS1-5*--.

Columns 35/36,
Table 4-continued, delete "NSI-7*" and insert therefor -- NS1-7* --.
Table 4-continued, delete "NSI-5*" and insert therefor -- NS1-5* --.
Table 6, title line, delete "peptides fr." and insert therefor -- peptides. --.
Table 6, 1st heading line, delete "SINGLE" and insert therefor -- SINGLE PEPTIDES --.
Table 6, 2nd heading line, delete "PEPTIDES".

Column 167,
Line 55, delete "the".

Column 169,
Lines 5, 20 and 54, delete "of".
Line 16, delete "Inducing" and insert therefor -- inducing --.

Column 170,
Line 3, delete "of".
Lines 52, 56 and 60 delete "39" and insert therefor -- 40 --.

Column 171,
Line 5, delete "30" and insert therefor -- 50 --.
Line 15, delete "39" and insert therefor -- 40 --.
Line 18, delete "of".

UNITED STATES PATENT AND TRADEMARK OFFICE
CERTIFICATE OF CORRECTION

PATENT NO. : 6,689,368 B1
DATED : February 10, 2004
INVENTOR(S) : Leroux-Roels et al.

It is certified that error appears in the above-identified patent and that said Letters Patent is hereby corrected as shown below:

Column 172,
Line 12, delete "of pypeptide" and insert therefor -- polypeptide --.
Lines 13, 19 and 22, delete "39" and insert therefor -- 40 --.

Signed and Sealed this

Seventh Day of September, 2004

JON W. DUDAS
*Director of the United States Patent and Trademark Office*

SEQUENCE LISTING (1) GENERAL INFORMATION:

(iii) NUMBER OF SEQUENCES: 181

(2) INFORMATION FOR SEQ ID NO: 1:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Pro Lys Pro Gln Arg Lys Thr Lys Arg Asn Thr Asn Arg Arg Pro
1           5                  10               15

(2) INFORMATION FOR SEQ ID NO: 2:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

Arg Asn Thr Asn Arg Arg Pro Gln Asp Val Lys Phe Pro Gly Gly Gly
1           5                  10               15

Gln Ile Val Gly
        20

(2) INFORMATION FOR SEQ ID NO: 3:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 3:

```
Pro Gly Gly Gly Gln Ile Val Gly Gly Val Tyr Leu Leu Pro Arg Arg
1               5                   10                  15

Gly Pro Arg Leu
            20
```

(2) INFORMATION FOR SEQ ID NO: 4:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Thr Arg Lys Thr Ser Glu Arg Ser Gln Pro Arg Gly Arg Arg Gln Pro
1               5                   10                  15

Ile Pro Lys Val
            20
```

(2) INFORMATION FOR SEQ ID NO: 5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Arg Arg Gln Pro Ile Pro Lys Val Arg Arg Pro Glu Gly Arg Thr Trp
1               5                   10                  15

Ala Gln Pro Gly
            20
```

(2) INFORMATION FOR SEQ ID NO: 6:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Gly Arg Thr Trp Ala Gln Pro Gly Tyr Pro Trp Pro Leu Tyr Gly Asn
1               5                   10                  15

Glu Gly Cys Gly
            20
```

(2) INFORMATION FOR SEQ ID NO: 7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Leu Tyr Gly Asn Glu Gly Cys Gly Trp Ala Gly Trp Leu Leu Ser Pro
1               5                   10                  15
```

Arg Gly Ser Arg
        20

(2) INFORMATION FOR SEQ ID NO: 8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Leu Leu Ser Pro Arg Gly Ser Arg Pro Ser Trp Gly Pro Thr Asp Pro
1               5                   10                  15

Arg Arg Arg Ser
        20

(2) INFORMATION FOR SEQ ID NO: 9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Pro Thr Asp Pro Arg Arg Arg Ser Arg Asn Leu Gly Lys Val Ile Asp
1               5                   10                  15

Thr Leu Thr Cys
        20

(2) INFORMATION FOR SEQ ID NO: 10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Lys Val Ile Asp Thr Leu Thr Cys Gly Phe Ala Asp Leu Met Gly Tyr
1               5                   10                  15

Ile Pro Leu Val
        20

(2) INFORMATION FOR SEQ ID NO: 11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Leu Met Gly Tyr Ile Pro Leu Val Gly Ala Pro Leu Gly Gly Ala Ala
1               5                   10                  15

Arg Ala Leu Ala
        20

(2) INFORMATION FOR SEQ ID NO: 12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Gly Gly Ala Ala Arg Ala Leu Ala His Gly Val Arg Val Leu Glu Asp
1               5                   10                  15
Gly Val Asn Tyr
            20
```

(2) INFORMATION FOR SEQ ID NO: 13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Val Leu Glu Asp Gly Val Asn Tyr Ala Thr Gly Asn Leu Pro Gly Cys
1               5                   10                  15
Ser Phe Ser Ile
            20
```

(2) INFORMATION FOR SEQ ID NO: 14:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Leu Pro Gly Cys Ser Phe Ser Ile Phe Leu Ala Leu Leu Ser Cys
1               5                   10                  15
Leu Thr Val Pro
            20
```

(2) INFORMATION FOR SEQ ID NO: 15:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Leu Leu Ser Cys Leu Thr Val Pro Ala Ser Ala Tyr Gln Val Arg Asn
1               5                   10                  15
Ser Thr Gly Leu
            20
```

(2) INFORMATION FOR SEQ ID NO: 16:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 16:

Gln Val Arg Asn Ser Thr Gly Leu Tyr His Val Thr Asn Asp Cys Pro
1               5                  10                  15

Asn Ser Ser Ile
            20

(2) INFORMATION FOR SEQ ID NO: 17:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 17:

Asn Asp Cys Pro Asn Ser Ser Ile Val Tyr Glu Ala His Asp Ala Ile
1               5                  10                  15

Leu His Thr Pro
            20

(2) INFORMATION FOR SEQ ID NO: 18:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 18:

His Asp Ala Ile Leu His Thr Pro Gly Cys Val Pro Cys Val Arg Glu
1               5                  10                  15

Gly Asn Val Ser
            20

(2) INFORMATION FOR SEQ ID NO: 19:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 19:

Cys Val Arg Glu Gly Asn Val Ser Arg Cys Trp Val Ala Met Thr Pro
1               5                  10                  15

Thr Val Ala Thr
            20

(2) INFORMATION FOR SEQ ID NO: 20:

(i) SEQUENCE CHARACTERISTICS:
              (A) LENGTH: 21 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 20:

Ala Met Thr Pro Thr Val Ala Thr Arg Asp Gly Lys Leu Pro Pro Ala
1               5                   10                  15

Thr Gln Leu Arg Arg
            20

(2) INFORMATION FOR SEQ ID NO: 21:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 21:

Leu Pro Ala Thr Gln Leu Arg Arg His Ile Asp Leu Leu Val Gly Ser
1               5                   10                  15

Ala Thr Leu Cys
            20

(2) INFORMATION FOR SEQ ID NO: 22:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 22:

Leu Val Gly Ser Ala Thr Leu Cys Ser Ala Leu Tyr Val Gly Asp Leu
1               5                   10                  15

Cys Gly Ser Val
            20

(2) INFORMATION FOR SEQ ID NO: 23:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 23:

Gln Leu Phe Thr Phe Ser Pro Arg Arg His Trp Thr Thr Gln Gly Cys
1               5                   10                  15

Asn Cys Ser Ile
            20

(2) INFORMATION FOR SEQ ID NO: 24:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 24:

Thr Gln Gly Cys Asn Cys Ser Ile Tyr Pro Gly His Ile Thr Gly His
1               5                   10                  15

Arg Met Ala Trp
            20

(2) INFORMATION FOR SEQ ID NO: 25:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Ile Thr Gly His Arg Met Ala Trp Asp Met Met Met Asn Trp Ser Pro
1               5                   10                  15

Thr Ala Ala Leu
            20

(2) INFORMATION FOR SEQ ID NO: 26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Asn Trp Ser Pro Thr Ala Ala Leu Val Met Ala Gln Leu Leu Arg Ile
1               5                   10                  15

Pro Gln Ala Ile
            20

(2) INFORMATION FOR SEQ ID NO: 27:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Leu Leu Arg Ile Pro Gln Ala Ile Leu Asp Met Ile Ala Gly Ala His
1               5                   10                  15

Trp Gly Val Leu
            20

(2) INFORMATION FOR SEQ ID NO: 28:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Ala Gly Ala His Trp Gly Val Leu Ala Gly Leu Ala Tyr Phe Ser Met
1               5                  10                  15

Val Gly Asn Met
            20

(2) INFORMATION FOR SEQ ID NO: 29:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Val Val Leu Leu Leu Phe Ala Gly Val Asp Ala Glu Thr Ile Val Ser
1               5                  10                  15

Gly Gly Gln Ala
            20

(2) INFORMATION FOR SEQ ID NO: 30:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Leu Asn Cys Asn Glu Ser Leu Asn Thr Gly Trp Leu Ala Gly Leu Ile
1               5                  10                  15

Tyr Gln His Lys
            20

(2) INFORMATION FOR SEQ ID NO: 31:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Ala Gly Leu Ile Tyr Gln His Lys Phe Asn Ser Ser Gly Cys Pro Glu
1               5                  10                  15

Arg Leu Ala Ser
            20

(2) INFORMATION FOR SEQ ID NO: 32:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Gly Cys Pro Glu Arg Leu Ala Ser Cys Arg Pro Leu Thr Asp Phe Asp

```
1               5                   10                  15
Gln Gly Trp Gly
            20
```

(2) INFORMATION FOR SEQ ID NO: 33:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

```
Thr Asp Phe Asp Gln Gly Trp Gly Pro Ile Ser Tyr Ala Asn Gly Ser
1               5                   10                  15
Gly Pro Asp Gln
            20
```

(2) INFORMATION FOR SEQ ID NO: 34:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

```
Ala Asn Gly Ser Gly Pro Asp Gln Arg Pro Tyr Cys Trp His Tyr Pro
1               5                   10                  15
Pro Lys Pro Cys
            20
```

(2) INFORMATION FOR SEQ ID NO: 35:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

```
Trp His Tyr Pro Pro Lys Pro Cys Gly Ile Val Pro Ala Lys Ser Val
1               5                   10                  15
Cys Gly Pro Val
            20
```

(2) INFORMATION FOR SEQ ID NO: 36:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

```
Ala Lys Ser Val Cys Gly Pro Val Tyr Cys Phe Thr Pro Ser Pro Val
1               5                   10                  15
Val Val Gly Thr
```

(2) INFORMATION FOR SEQ ID NO: 37:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Pro Ser Pro Val Val Val Gly Thr Thr Asp Arg Ser Gly Ala Pro Thr
1               5                   10                  15
Tyr Ser Trp Gly
            20
```

(2) INFORMATION FOR SEQ ID NO: 38:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

```
Gln Leu Phe Thr Phe Ser Pro Arg Arg His Trp Thr Thr Gln Gly Cys
1               5                   10                  15
Asn Cys Ser Ile
            20
```

(2) INFORMATION FOR SEQ ID NO: 39:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

```
Gly Asn Trp Phe Gly Cys Thr Trp Met Asn Ser Thr Gly Phe Thr Lys
1               5                   10                  15
Val Cys Gly Ala
            20
```

(2) INFORMATION FOR SEQ ID NO: 40:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

```
Gly Phe Thr Lys Val Cys Gly Ala Pro Pro Cys Val Ile Gly Gly Ala
1               5                   10                  15
Gly Asn Asn Thr
            20
```

(2) INFORMATION FOR SEQ ID NO: 41:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Ile Gly Gly Ala Gly Asn Asn Thr Leu His Cys Pro Thr Asp Cys Phe
1               5                   10                  15

Arg Lys His Pro
            20

(2) INFORMATION FOR SEQ ID NO: 42:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Thr Asp Cys Phe Arg Lys His Pro Asp Ala Thr Tyr Ser Arg Cys Gly
1               5                   10                  15

Ser Gly Pro Trp
            20

(2) INFORMATION FOR SEQ ID NO: 43:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 43:

Ser Arg Cys Gly Ser Gly Pro Trp Ile Thr Pro Arg Cys Leu Val Asp
1               5                   10                  15

Tyr Pro Tyr Arg
            20

(2) INFORMATION FOR SEQ ID NO: 44:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 44:

Cys Leu Val Asp Tyr Pro Tyr Arg Leu Trp His Tyr Pro Cys Thr Ile
1               5                   10                  15

Asn Tyr Thr Ile
            20

(2) INFORMATION FOR SEQ ID NO: 45:

(i) SEQUENCE CHARACTERISTICS:

(A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 45:

Pro Cys Thr Ile Asn Tyr Thr Ile Phe Lys Ile Arg Met Tyr Val Gly
1               5                   10                  15

Gly Val Glu His
            20

(2) INFORMATION FOR SEQ ID NO: 46:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 46:

Ser Gly Leu Val Ser Leu Phe Thr Pro Gly Ala Lys Gln Asn Ile Gln
1               5                   10                  15

Leu Ile Asn Thr
            20

(2) INFORMATION FOR SEQ ID NO: 47:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 47:

Gln Asn Ile Gln Leu Ile Asn Thr Asn Gly Ser Trp His Ile Asn Ser
1               5                   10                  15

Thr Ala Leu Asn
            20

(2) INFORMATION FOR SEQ ID NO: 48:

(i) SEQUENCE CHARACTERISTICS:
            (A) LENGTH: 68 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 1
            (D) OTHER INFORMATION: Xaa is Pro or Gln (ix) FEATURE:
            (A) NAME/KEY: misc-feature
            (B) LOCATION: 2
            (D) OTHER INFORMATION: Xaa is Asn or Thr (ix) FEATURE:
            (A) NAME/KEY: misc-feature
            (B) LOCATION: 6
            (D) OTHER INFORMATION: Xaa is Arg or His

```
(ix) FEATURE:
    (A) NAME/KEY: misc-feature
    (B) LOCATION: 7
    (D) OTHER INFORMATION: Xaa is Arg or Lys (ix) FEATURE:
    (A) NAME/KEY: misc-feature
    (B) LOCATION: 11
    (D) OTHER INFORMATION: Xaa is Leu or Val or Phe (ix) FEATURE:
    (A) NAME/KEY: misc-feature
    (B) LOCATION: 13
    (D) OTHER INFORMATION: Xaa is Lys or Arg (ix) FEATURE:
    (A) NAME/KEY: misc-feature
    (B) LOCATION: 18
    (D) OTHER INFORMATION: Xaa is Leu or Ile (ix) FEATURE:
    (A) NAME/KEY: misc-feature
    (B) LOCATION: 22
    (D) OTHER INFORMATION: Xaa is Phe or Leu (ix) FEATURE:
    (A) NAME/KEY: misc-feature
    (B) LOCATION: 26
    (D) OTHER INFORMATION: Xaa is Met or Ile (ix) FEATURE:
    (A) NAME/KEY: misc-feature
    (B) LOCATION: 27
    (D) OTHER INFORMATION: Xaa is Gly or Glu (ix) FEATURE:
    (A) NAME/KEY: misc-feature
    (B) LOCATION: 31
    (D) OTHER INFORMATION: Xaa is Leu or Val or Ile (ix) FEATURE:
    (A) NAME/KEY: misc-feature
    (B) LOCATION: 32
    (D) OTHER INFORMATION: Xaa is Val or Leu (ix) FEATURE:
    (A) NAME/KEY: misc-feature
    (B) LOCATION: 34
    (D) OTHER INFORMATION: Xaa is Ala or Gly (ix) FEATURE:
    (A) NAME/KEY: misc-feature
    (B) LOCATION: 36
    (D) OTHER INFORMATION: Xaa is Leu or Val or Ile (ix) FEATURE:
    (A) NAME/KEY: misc-feature
    (B) LOCATION: 39
    (D) OTHER INFORMATION: Xaa is Ala or Val (ix) FEATURE:
    (A) NAME/KEY: misc-feature
    (B) LOCATION: 40
    (D) OTHER INFORMATION: Xaa is Ala or Ser (ix) FEATURE:
    (A) NAME/KEY: misc-feature
    (B) LOCATION: 41
    (D) OTHER INFORMATION: Xaa is Arg or Ala (ix) FEATURE:
    (A) NAME/KEY: misc-feature
    (B) LOCATION: 42
    (D) OTHER INFORMATION: Xaa is Ala or Thr or Glu (ix) FEATURE:
    (A) NAME/KEY: misc-feature
    (B) LOCATION: 44
    (D) OTHER INFORMATION: Xaa is Ala or Glu
```

(ix) FEATURE:
    (A) NAME/KEY: misc-feature
    (B) LOCATION: 49
    (D) OTHER INFORMATION: Xaa is Val or Ala or Leu (ix) FEATURE:
    (A) NAME/KEY: misc-feature
    (B) LOCATION: 50
    (D) OTHER INFORMATION: Xaa is Leu or Val or Ile (ix) FEATURE:
    (A) NAME/KEY: misc-feature
    (B) LOCATION: 51
    (D) OTHER INFORMATION: Xaa is Glu or Gly (ix) FEATURE:
    (A) NAME/KEY: misc-feature
    (B) LOCATION: 54
    (D) OTHER INFORMATION: Xaa is Val or Ile (ix) FEATURE:
    (A) NAME/KEY: misc-feature
    (B) LOCATION: 56
    (D) OTHER INFORMATION: Xaa is Phe or Tyr (ix) FEATURE:
    (A) NAME/KEY: misc-feature
    (B) LOCATION: 57
    (D) OTHER INFORMATION: Xaa is Ala or Pro (ix) FEATURE:
    (A) NAME/KEY: misc-feature
    (B) LOCATION: 61
    (D) OTHER INFORMATION: Xaa is Leu or Ile (xi) SEQUENCE DESCRIPTION: SEQ ID NO: 48:

Xaa Xaa Asp Pro Arg Xaa Xaa Ser Arg Asn Xaa Gly Xaa Val Ile Asp
1               5                   10                  15

Thr Xaa Thr Cys Gly Xaa Ala Asp Leu Xaa Xaa Tyr Ile Pro Xaa Xaa
            20                  25                  30

Gly Xaa Pro Xaa Gly Gly Xaa Xaa Xaa Leu Xaa His Gly Val Arg
        35                  40                  45

Xaa Xaa Xaa Asp Gly Xaa Asn Xaa Xaa Thr Gly Asn Xaa Pro Gly Cys
    50                  55                  60

Ser Phe Ser Ile
65

(2) INFORMATION FOR SEQ ID NO: 49:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION:   Xaa is Ser or Ala or Gln or Leu or
            Asn or Tyr or Arg or His (ix) FEATURE:
        (A) NAME/KEY: misc-feature
        (B) LOCATION: 2
        (D) OTHER INFORMATION: Xaa is Gly or Ser or Thr or Ala or
            Arg (ix) FEATURE:
        (A) NAME/KEY: misc-feature
        (B) LOCATION: 3

(D) OTHER INFORMATION: Xaa is Phe or Ile or Leu or Val (ix) FEATURE:
        (A) NAME/KEY: misc-feature
        (B) LOCATION: 4
        (D) OTHER INFORMATION: Xaa is Val or Ala or Thr (ix) FEATURE:
        (A) NAME/KEY: misc-feature
        (B) LOCATION: 5
        (D) OTHER INFORMATION: Xaa is Ser or Asp or Gly (ix) FEATURE:
        (A) NAME/KEY: misc-feature
        (B) LOCATION: 6
        (D) OTHER INFORMATION: Xaa is Leu or Ile or Trp or Phe or Met (ix) FEATURE:
        (A) NAME/KEY: misc-feature
        (B) LOCATION: 7
        (D) OTHER INFORMATION: Xaa is Leu or Ile or Phe (ix) FEATURE:
        (A) NAME/KEY: misc-feature
        (B) LOCATION: 8
        (D) OTHER INFORMATION: Xaa is Ala or Thr or Asp or Ser (ix) FEATURE:
        (A) NAME/KEY: misc-feature
        (B) LOCATION: 9
        (D) OTHER INFORMATION:   Xaa is Pro or Gln or Ser or Arg or
        Leu or Ile or Thr (ix) FEATURE:
        (A) NAME/KEY: misc-feature
        (B) LOCATION: 11
        (D) OTHER INFORMATION: Xaa is Ala or Pro or Ser (ix) FEATURE:
        (A) NAME/KEY: misc-feature
        (B) LOCATION: 12
        (D) OTHER INFORMATION: Xaa is Lys or Ser or Gln or Ala or Arg (ix) FEATURE:
        (A) NAME/KEY: misc-feature
        (B) LOCATION: 14
        (D) OTHER INFORMATION: Xaa is Asn or Lys or Asp or Arg (ix) FEATURE:
        (A) NAME/KEY: misc-feature
        (B) LOCATION: 15
        (D) OTHER INFORMATION: Xaa is Val or Ile or Leu (ix) FEATURE:
        (A) NAME/KEY: misc-feature
        (B) LOCATION: 16
        (D) OTHER INFORMATION: Xaa is Gln or Ser or Tyr (ix) FEATURE:
        (A) NAME/KEY: misc-feature
        (B) LOCATION: 18
        (D) OTHER INFORMATION: Xaa is Ile or Val (ix) FEATURE:
        (A) NAME/KEY: misc-feature
        (B) LOCATION: 20
        (D) OTHER INFORMATION: Xaa is Thr or Ser (ix) FEATURE:
        (A) NAME/KEY: misc-feature
        (B) LOCATION: 26
        (D) OTHER INFORMATION: Xaa is Leu or Ile (ix) FEATURE:
        (A) NAME/KEY: misc-feature
        (B) LOCATION: 28
        (D) OTHER INFORMATION: Xaa is Ser or Arg (xi) SEQUENCE DESCRIPTION: SEQ ID NO: 49:

Xaa Xaa Xaa Xaa Xaa Xaa Xaa Xaa Xaa Gly Xaa Gln Xaa Xaa Xaa
1               5                   10              15

Leu Xaa Asn Xaa Asn Gly Ser Trp His Xaa Asn Xaa Thr Ala Leu Asn
            20              25              30

(2) INFORMATION FOR SEQ ID NO: 50:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 2
        (D) OTHER INFORMATION: Xaa is Met or Ile (ix) FEATURE:
        (A) NAME/KEY: misc-feature
        (B) LOCATION: 3
        (D) OTHER INFORMATION: Xaa is Gly or Glu (ix) FEATURE:
        (A) NAME/KEY: misc-feature
        (B) LOCATION: 7
        (D) OTHER INFORMATION: Xaa is Leu or Val or Ile (ix) FEATURE:
        (A) NAME/KEY: misc-feature
        (B) LOCATION: 8
        (D) OTHER INFORMATION: Xaa is Val or Leu (ix) FEATURE:
        (A) NAME/KEY: misc-feature
        (B) LOCATION: 10
        (D) OTHER INFORMATION: Xaa is Ala or Gly (ix) FEATURE:
        (A) NAME/KEY: misc-feature
        (B) LOCATION: 12
        (D) OTHER INFORMATION: Xaa is Leu or Val or Ile (ix) FEATURE:
        (A) NAME/KEY: misc-feature
        (B) LOCATION: 15
        (D) OTHER INFORMATION: Xaa is Ala or Val (ix) FEATURE:
        (A) NAME/KEY: misc-feature
        (B) LOCATION: 16
        (D) OTHER INFORMATION: Xaa is Ala or Ser (ix) FEATURE:
        (A) NAME/KEY: misc-feature
        (B) LOCATION: 17
        (D) OTHER INFORMATION: Xaa is Arg or Ala (ix) FEATURE:
        (A) NAME/KEY: misc-feature
        (B) LOCATION: 18
        (D) OTHER INFORMATION: Xaa is Ala or Thr or Glu (ix) FEATURE:
        (A) NAME/KEY: misc-feature
        (B) LOCATION: 20
        (D) OTHER INFORMATION: Xaa is Ala or Glu (ix) FEATURE:
        (A) NAME/KEY: misc-feature
        (B) LOCATION: 25
        (D) OTHER INFORMATION: Xaa is Val or Ala or Leu (ix) FEATURE:

```
        (A) NAME/KEY: misc-feature
        (B) LOCATION: 26
        (D) OTHER INFORMATION: Xaa is Leu or Val or Ile (ix) FEATURE:
        (A) NAME/KEY: misc-feature
        (B) LOCATION: 27
        (D) OTHER INFORMATION: Xaa is Glu or Gly (ix) FEATURE:
        (A) NAME/KEY: misc-feature
        (B) LOCATION: 30
        (D) OTHER INFORMATION: Xaa is Val or Ile (ix) FEATURE:
        (A) NAME/KEY: misc-feature
        (B) LOCATION: 32
        (D) OTHER INFORMATION: Xaa is Phe or Tyr (ix) FEATURE:
        (A) NAME/KEY: misc-feature
        (B) LOCATION: 33
        (D) OTHER INFORMATION: Xaa is Ala or Pro (ix) FEATURE:
        (A) NAME/KEY: misc-feature
        (B) LOCATION: 37
        (D) OTHER INFORMATION: Xaa is Leu or Ile (xi) SEQUENCE DESCRIPTION: SEQ ID NO: 50:

Leu Xaa Xaa Tyr Ile Pro Xaa Xaa Gly Xaa Pro Xaa Gly Gly Xaa Xaa
1               5                   10                  15

Xaa Xaa Leu Xaa His Gly Val Arg Xaa Xaa Xaa Asp Gly Xaa Asn Xaa
            20                  25                  30

Xaa Thr Gly Asn Xaa Pro Gly Cys Ser Phe Ser Ile
        35                  40

(2) INFORMATION FOR SEQ ID NO: 51:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Val or Ala or Leu (ix) FEATURE:
        (A) NAME/KEY: misc-feature
        (B) LOCATION: 2
        (D) OTHER INFORMATION: Xaa is Leu or Val or Ile (ix) FEATURE:
        (A) NAME/KEY: misc-feature
        (B) LOCATION: 3
        (D) OTHER INFORMATION: Xaa is Glu or Gly (ix) FEATURE:
        (A) NAME/KEY: misc-feature
        (B) LOCATION: 6
        (D) OTHER INFORMATION: Xaa is Val or Ile (ix) FEATURE:
        (A) NAME/KEY: misc-feature
        (B) LOCATION: 8
        (D) OTHER INFORMATION: Xaa is Phe or Tyr (ix) FEATURE:
        (A) NAME/KEY: misc-feature
        (B) LOCATION: 9
```

(D) OTHER INFORMATION: Xaa is Ala or Pro (ix) FEATURE:
    (A) NAME/KEY: misc-feature
    (B) LOCATION: 13
    (D) OTHER INFORMATION: Xaa is Leu or Ile (xi) SEQUENCE DESCRIPTION: SEQ ID NO: 51:

Xaa Xaa Xaa Asp Gly Xaa Asn Xaa Xaa Thr Gly Asn Xaa Pro Gly Cys
1          5                  10               15

Ser Phe Ser Ile
          20

(2) INFORMATION FOR SEQ ID NO: 52:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 3
        (D) OTHER INFORMATION: Xaa is Ala or Val (ix) FEATURE:
        (A) NAME/KEY: misc-feature
        (B) LOCATION: 4
        (D) OTHER INFORMATION: Xaa is Ala or Ser (ix) FEATURE:
        (A) NAME/KEY: misc-feature
        (B) LOCATION: 5
        (D) OTHER INFORMATION: Xaa is Arg or Ala (ix) FEATURE:
        (A) NAME/KEY: misc-feature
        (B) LOCATION: 6
        (D) OTHER INFORMATION: Xaa is Ala or Thr or Glu (ix) FEATURE:
        (A) NAME/KEY: misc-feature
        (B) LOCATION: 8
        (D) OTHER INFORMATION: Xaa is Ala or Glu (ix) FEATURE:
        (A) NAME/KEY: misc-feature
        (B) LOCATION: 13
        (D) OTHER INFORMATION: Xaa is Val or Ala or Leu (ix) FEATURE:
        (A) NAME/KEY: misc-feature
        (B) LOCATION: 14
        (D) OTHER INFORMATION: Xaa is Leu or Val or Ile (ix) FEATURE:
        (A) NAME/KEY: misc-feature
        (B) LOCATION: 15
        (D) OTHER INFORMATION: Xaa is Glu or Gly (ix) FEATURE:
        (A) NAME/KEY: misc-feature
        (B) LOCATION: 18
        (D) OTHER INFORMATION: Xaa is Val or Ile (ix) FEATURE:
        (A) NAME/KEY: misc-feature
        (B) LOCATION: 20
        (D) OTHER INFORMATION: Xaa is Phe or Tyr (xi) SEQUENCE DESCRIPTION: SEQ ID NO: 52:

Xaa Xaa Xaa Asp Gly Xaa Asn Xaa Xaa Thr Gly Asn Xaa Pro Gly Cys

```
1               5                  10                 15
Ser Phe Ser Ile
            20
```

(2) INFORMATION FOR SEQ ID NO: 53:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 2
        (D) OTHER INFORMATION: Xaa is Met or Ile (ix) FEATURE:
        (A) NAME/KEY: misc-feature
        (B) LOCATION: 3
        (D) OTHER INFORMATION: Xaa is Gly or Glu (ix) FEATURE:
        (A) NAME/KEY: misc-feature
        (B) LOCATION: 7
        (D) OTHER INFORMATION: Xaa is Leu or Val or Ile (ix) FEATURE:
        (A) NAME/KEY: misc-feature
        (B) LOCATION: 8
        (D) OTHER INFORMATION: Xaa is Val or Leu (ix) FEATURE:
        (A) NAME/KEY: misc-feature
        (B) LOCATION: 10
        (D) OTHER INFORMATION: Xaa is Ala or Gly (ix) FEATURE:
        (A) NAME/KEY: misc-feature
        (B) LOCATION: 12
        (D) OTHER INFORMATION: Xaa is Leu or Val or Ile (ix) FEATURE:
        (A) NAME/KEY: misc-feature
        (B) LOCATION: 15
        (D) OTHER INFORMATION: Xaa is Ala or Val (ix) FEATURE:
        (A) NAME/KEY: misc-feature
        (B) LOCATION: 16
        (D) OTHER INFORMATION: Xaa is Ala or Ser (ix) FEATURE:
        (A) NAME/KEY: misc-feature
        (B) LOCATION: 17
        (D) OTHER INFORMATION: Xaa is Arg or Ala (ix) FEATURE:
        (A) NAME/KEY: misc-feature
        (B) LOCATION: 18
        (D) OTHER INFORMATION: Xaa is Ala or Thr or Glu (ix) FEATURE:
        (A) NAME/KEY: misc-feature
        (B) LOCATION: 20
        (D) OTHER INFORMATION: Xaa is Ala or Glu (xi) SEQUENCE DESCRIPTION: SEQ ID NO: 53:

```
Leu Xaa Xaa Tyr Ile Pro Xaa Xaa Gly Xaa Pro Xaa Gly Gly Xaa Xaa
1               5                  10                 15
Xaa Xaa Leu Xaa
            20
```

(2) INFORMATION FOR SEQ ID NO: 54:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Pro or Gln (ix) FEATURE:
        (A) NAME/KEY: misc-feature
        (B) LOCATION: 2
        (D) OTHER INFORMATION: Xaa is Asn or Thr (ix) FEATURE:
        (A) NAME/KEY: misc-feature
        (B) LOCATION: 6
        (D) OTHER INFORMATION: Xaa is Arg or His (ix) FEATURE:
        (A) NAME/KEY: misc-feature
        (B) LOCATION: 7
        (D) OTHER INFORMATION: Xaa is Arg or Lys (ix) FEATURE:
        (A) NAME/KEY: misc-feature
        (B) LOCATION: 11
        (D) OTHER INFORMATION: Xaa is Leu or Val or Phe (ix) FEATURE:
        (A) NAME/KEY: misc-feature
        (B) LOCATION: 13
        (D) OTHER INFORMATION: Xaa is Lys or Arg (ix) FEATURE:
        (A) NAME/KEY: misc-feature
        (B) LOCATION: 18
        (D) OTHER INFORMATION: Xaa is Leu or Ile (xi) SEQUENCE DESCRIPTION: SEQ ID NO: 54:

```
Xaa Xaa Asp Pro Arg Xaa Xaa Ser Arg Asn Xaa Gly Xaa Val Ile Asp
1               5                   10                  15
Thr Xaa Thr Cys
        20
```

(2) INFORMATION FOR SEQ ID NO: 55:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Ser or Ala or Gln or Leu or Asn or Tyr or Arg or His (ix) FEATURE:
        (A) NAME/KEY: misc-feature
        (B) LOCATION: 2
        (D) OTHER INFORMATION: Xaa is Gly or Ser or Thr or Ala or Arg (ix) FEATURE:
        (A) NAME/KEY: misc-feature
        (B) LOCATION: 3

(D) OTHER INFORMATION: Xaa is Phe or Ile or Leu or Val (ix) FEATURE:
                    (A) NAME/KEY: misc-feature
                    (B) LOCATION: 4
                    (D) OTHER INFORMATION: Xaa is Val or Ala or Thr (ix) FEATURE:
                    (A) NAME/KEY: misc-feature
                    (B) LOCATION: 5
                    (D) OTHER INFORMATION: Xaa is Ser or Asp or Gly (ix) FEATURE:
                    (A) NAME/KEY: misc-feature
                    (B) LOCATION: 6
                    (D) OTHER INFORMATION: Xaa is Leu or Ile or Trp or Phe or Met (ix) FEATURE:
                    (A) NAME/KEY: misc-feature
                    (B) LOCATION: 7
                    (D) OTHER INFORMATION: Xaa is Leu or Ile or Phe (ix) FEATURE:
                    (A) NAME/KEY: misc-feature
                    (B) LOCATION: 8
                    (D) OTHER INFORMATION: Xaa is Ala or Thr or Asp or Ser (ix) FEATURE:
                    (A) NAME/KEY: misc-feature
                    (B) LOCATION: 9
                    (D) OTHER INFORMATION:   Xaa is Pro or Gln or Ser or Arg or
                    Leu or Ile or Thr (ix) FEATURE:
                    (A) NAME/KEY: misc-feature
                    (B) LOCATION: 11
                    (D) OTHER INFORMATION: Xaa is Ala or Pro or Ser (ix) FEATURE:
                    (A) NAME/KEY: misc-feature
                    (B) LOCATION: 12
                    (D) OTHER INFORMATION: Xaa is Lys or Ser or Gln or Ala or Arg (ix) FEATURE:
                    (A) NAME/KEY: misc-feature
                    (B) LOCATION: 14
                    (D) OTHER INFORMATION: Xaa is Asn or Lys or Asp or Arg (ix) FEATURE:
                    (A) NAME/KEY: misc-feature
                    (B) LOCATION: 15
                    (D) OTHER INFORMATION: Xaa is Val or Ile or Leu (ix) FEATURE:
                    (A) NAME/KEY: misc-feature
                    (B) LOCATION: 16
                    (D) OTHER INFORMATION: Xaa is Gln or Ser or Tyr (ix) FEATURE:
                    (A) NAME/KEY: misc-feature
                    (B) LOCATION: 18
                    (D) OTHER INFORMATION: Xaa is Ile or Val (ix) FEATURE:
                    (A) NAME/KEY: misc-feature
                    (B) LOCATION: 20
                    (D) OTHER INFORMATION: Xaa is Thr or Ser (xi) SEQUENCE DESCRIPTION: SEQ ID NO: 55:

Xaa Xaa Xaa Xaa Xaa Xaa Xaa Xaa Xaa Gly Xaa Xaa Gln Xaa Xaa Xaa
1               5                   10                  15

Leu Xaa Asn Xaa
            20

(2) INFORMATION FOR SEQ ID NO: 56:

```
    (i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 2
        (D) OTHER INFORMATION: Xaa is Asn or Lys or Asp or Arg (ix) FEATURE:
        (A) NAME/KEY: misc-feature
        (B) LOCATION: 3
        (D) OTHER INFORMATION: Xaa is Val or Ile or Leu (ix) FEATURE:
        (A) NAME/KEY: misc-feature
        (B) LOCATION: 4
        (D) OTHER INFORMATION: Xaa is Gln or Ser or Tyr (ix) FEATURE:
        (A) NAME/KEY: misc-feature
        (B) LOCATION: 6
        (D) OTHER INFORMATION: Xaa is Ile or Val (ix) FEATURE:
        (A) NAME/KEY: misc-feature
        (B) LOCATION: 8
        (D) OTHER INFORMATION: Xaa is Thr or Ser (ix) FEATURE:
        (A) NAME/KEY: misc-feature
        (B) LOCATION: 14
        (D) OTHER INFORMATION: Xaa is Leu or Ile (ix) FEATURE:
        (A) NAME/KEY: misc-feature
        (B) LOCATION: 16
        (D) OTHER INFORMATION: Xaa is Ser or Arg (xi) SEQUENCE DESCRIPTION: SEQ ID NO: 56:

Gln Xaa Xaa Xaa Leu Xaa Asn Xaa Asn Gly Ser Trp His Xaa Asn Xaa
1               5                   10                  15

Thr Ala Leu Asn
            20

(2) INFORMATION FOR SEQ ID NO: 57:

(i) SEQUENCE CHARACTERISTICS:
        (A) LENGTH: 278 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

Gly Val Ala Lys Ala Val Asp Phe Val Pro Val Glu Ser Met Glu Thr
1               5                   10                  15

Thr Met Arg Ser Pro Val Phe Thr Asp Asn Ser Ser Pro Pro Ala Val
            20                  25                  30

Pro Gln Thr Phe Gln Val Ala His Leu His Ala Pro Thr Gly Ser Gly
            35                  40                  45

Lys Ser Thr Lys Val Pro Ala Ala Tyr Ala Ala Gln Gly Tyr Lys Val
        50                  55                  60

Leu Val Leu Asn Pro Ser Val Ala Ala Thr Leu Gly Phe Gly Ala Tyr
65                  70                  75                  80
```

```
Met Ser Lys Ala His Gly Val Asp Pro Asn Ile Arg Thr Gly Val Arg
                85                  90                  95

Thr Ile Thr Thr Gly Ala Pro Ile Thr Tyr Ser Thr Tyr Gly Lys Phe
               100                 105                 110

Leu Ala Asp Gly Gly Cys Ser Gly Gly Ala Tyr Asp Ile Ile Ile Cys
               115                 120                 125

Asp Glu Cys His Ser Ile Asp Ser Thr Ser Ile Leu Gly Ile Gly Thr
           130                 135                 140

Val Leu Asp Gln Ala Glu Thr Ala Gly Ala Arg Leu Val Val Leu Ala
145                 150                 155                 160

Thr Ala Thr Pro Pro Gly Ser Val Thr Val Pro His Pro Asn Ile Glu
               165                 170                 175

Glu Val Ala Leu Ser Ser Thr Gly Glu Ile Pro Phe Tyr Gly Lys Ala
               180                 185                 190

Ile Pro Ile Glu Val Ile Lys Gly Gly Arg His Leu Ile Phe Cys His
               195                 200                 205

Ser Lys Lys Lys Cys Asp Glu Leu Ala Ala Lys Leu Ser Gly Phe Gly
               210                 215                 220

Ile Asn Ala Val Ala Tyr Tyr Arg Gly Leu Asp Val Ser Val Ile Pro
225                 230                 235                 240

Thr Ser Gly Asp Val Val Val Ala Thr Asp Ala Leu Met Thr Gly
               245                 250                 255

Phe Thr Gly Asp Phe Asp Ser Val Ile Asp Cys Asn Thr Cys Val Thr
               260                 265                 270

Gln Thr Val Asp Phe Ser
        275
```

(2) INFORMATION FOR SEQ ID NO: 58:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 2
        (D) OTHER INFORMATION: Xaa is Arg or Lys (ix) FEATURE:
        (A) NAME/KEY: misc-feature
        (B) LOCATION: 3
        (D) OTHER INFORMATION: Xaa is Ala or Ser or Thr (ix) FEATURE:
        (A) NAME/KEY: misc-feature
        (B) LOCATION: 5
        (D) OTHER INFORMATION: Xaa is Ala or Gly (ix) FEATURE:
        (A) NAME/KEY: misc-feature
        (B) LOCATION: 6
        (D) OTHER INFORMATION: Xaa is Gln or Lys or Arg (ix) FEATURE:
        (A) NAME/KEY: misc-feature
        (B) LOCATION: 9
        (D) OTHER INFORMATION: Xaa is Tyr or His (ix) FEATURE:
        (A) NAME/KEY: misc-feature
        (B) LOCATION: 15
        (D) OTHER INFORMATION: Xaa is Gly or Ala

```
(ix) FEATURE:
    (A) NAME/KEY: misc-feature
    (B) LOCATION: 17
    (D) OTHER INFORMATION: Xaa is Glu or Lys (ix) FEATURE:
    (A) NAME/KEY: misc-feature
    (B) LOCATION: 19
    (D) OTHER INFORMATION: Xaa is Cys or Met or Leu (ix) FEATURE:
    (A) NAME/KEY: misc-feature
    (B) LOCATION: 21
    (D) OTHER INFORMATION: Xaa is Trp or Leu (ix) FEATURE:
    (A) NAME/KEY: misc-feature
    (B) LOCATION: 34
    (D) OTHER INFORMATION: Xaa is Ser or Asn or Thr or Asp or His (ix) FEATURE:
    (A) NAME/KEY: misc-feature
    (B) LOCATION: 37
    (D) OTHER INFORMATION: Xaa is Pro or Gln (ix) FEATURE:
    (A) NAME/KEY: misc-feature
    (B) LOCATION: 38
    (D) OTHER INFORMATION: Xaa is Asn or Thr (ix) FEATURE:
    (A) NAME/KEY: misc-feature
    (B) LOCATION: 42
    (D) OTHER INFORMATION: Xaa is Arg or His (ix) FEATURE:
    (A) NAME/KEY: misc-feature
    (B) LOCATION: 43
    (D) OTHER INFORMATION: Xaa is Arg or Lys (ix) FEATURE:
    (A) NAME/KEY: misc-feature
    (B) LOCATION: 47
    (D) OTHER INFORMATION: Xaa is Leu or Val or Phe (ix) FEATURE:
    (A) NAME/KEY: misc-feature
    (B) LOCATION: 49
    (D) OTHER INFORMATION: Xaa is Lys or Arg (ix) FEATURE:
    (A) NAME/KEY: misc-feature
    (B) LOCATION: 54
    (D) OTHER INFORMATION: Xaa is Leu or Ile (ix) FEATURE:
    (A) NAME/KEY: misc-feature
    (B) LOCATION: 58
    (D) OTHER INFORMATION: Xaa is Phe or Leu (ix) FEATURE:
    (A) NAME/KEY: misc-feature
    (B) LOCATION: 62
    (D) OTHER INFORMATION: Xaa is Met or Ile (ix) FEATURE:
    (A) NAME/KEY: misc-feature
    (B) LOCATION: 63
    (D) OTHER INFORMATION: Xaa is Gly or Glu (ix) FEATURE:
    (A) NAME/KEY: misc-feature
    (B) LOCATION: 67
    (D) OTHER INFORMATION: Xaa is Leu or Val or Ile (ix) FEATURE:
    (A) NAME/KEY: misc-feature
    (B) LOCATION: 68
```

(D) OTHER INFORMATION: Xaa is Val or Leu (ix) FEATURE:
    (A) NAME/KEY: misc-feature
    (B) LOCATION: 70
    (D) OTHER INFORMATION: Xaa is Ala or Gly (ix) FEATURE:
    (A) NAME/KEY: misc-feature
    (B) LOCATION: 72
    (D) OTHER INFORMATION: Xaa is Leu or Val or Ile (ix) FEATURE:
    (A) NAME/KEY: misc-feature
    (B) LOCATION: 75
    (D) OTHER INFORMATION: Xaa is Ala or Val (ix) FEATURE:
    (A) NAME/KEY: misc-feature
    (B) LOCATION: 76
    (D) OTHER INFORMATION: Xaa is Ala or Ser (ix) FEATURE:
    (A) NAME/KEY: misc-feature
    (B) LOCATION: 77
    (D) OTHER INFORMATION: Xaa is Arg or Ala (ix) FEATURE:
    (A) NAME/KEY: misc-feature
    (B) LOCATION: 78
    (D) OTHER INFORMATION: Xaa is Ala or Thr or Glu (ix) FEATURE:
    (A) NAME/KEY: misc-feature
    (B) LOCATION: 80
    (D) OTHER INFORMATION: Xaa is Ala or Glu (ix) FEATURE:
    (A) NAME/KEY: misc-feature
    (B) LOCATION: 85
    (D) OTHER INFORMATION: Xaa is Val or Ala or Leu (ix) FEATURE:
    (A) NAME/KEY: misc-feature
    (B) LOCATION: 86
    (D) OTHER INFORMATION: Xaa is Leu or Val or Ile (ix) FEATURE:
    (A) NAME/KEY: misc-feature
    (B) LOCATION: 87
    (D) OTHER INFORMATION: Xaa is Glu or Gly (ix) FEATURE:
    (A) NAME/KEY: misc-feature
    (B) LOCATION: 90
    (D) OTHER INFORMATION: Xaa is Val or Ile (ix) FEATURE:
    (A) NAME/KEY: misc-feature
    (B) LOCATION: 92
    (D) OTHER INFORMATION: Xaa is Phe or Tyr (ix) FEATURE:
    (A) NAME/KEY: misc-feature
    (B) LOCATION: 93
    (D) OTHER INFORMATION: Xaa is Ala or Pro (ix) FEATURE:
    (A) NAME/KEY: misc-feature
    (B) LOCATION: 97
    (D) OTHER INFORMATION: Xaa is Leu or Ile (xi) SEQUENCE DESCRIPTION: SEQ ID NO: 58:

Gly Xaa Xaa Trp Xaa Xaa Pro Gly Xaa Pro Trp Pro Leu Tyr Xaa Asn
1               5                  10                  15

Xaa Gly Xaa Gly Xaa Ala Gly Trp Leu Leu Ser Pro Arg Gly Ser Arg
            20                  25                  30

```
Pro Xaa Trp Gly Xaa Xaa Asp Pro Arg Xaa Xaa Ser Arg Asn Xaa Gly
        35                  40                  45

Xaa Val Ile Asp Thr Xaa Thr Cys Gly Xaa Ala Asp Leu Xaa Xaa Tyr
 50                  55                  60

Ile Pro Xaa Xaa Gly Xaa Pro Xaa Gly Xaa Xaa Xaa Xaa Leu Xaa
65              70              75                      80

His Gly Val Arg Xaa Xaa Xaa Asp Gly Xaa Asn Xaa Xaa Thr Gly Asn
                85                  90                  95

Xaa Pro Gly Cys Ser Phe Ser Ile
            100
```

(2) INFORMATION FOR SEQ ID NO: 59:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 2
        (D) OTHER INFORMATION: Xaa is Arg or Lys (ix) FEATURE:
        (A) NAME/KEY: misc-feature
        (B) LOCATION: 3
        (D) OTHER INFORMATION: Xaa is Ala or Ser or Thr (ix) FEATURE:
        (A) NAME/KEY: misc-feature
        (B) LOCATION: 5
        (D) OTHER INFORMATION: Xaa is Ala or Gly (ix) FEATURE:
        (A) NAME/KEY: misc-feature
        (B) LOCATION: 6
        (D) OTHER INFORMATION: Xaa is Gln or Lys or Arg (ix) FEATURE:
        (A) NAME/KEY: misc-feature
        (B) LOCATION: 9
        (D) OTHER INFORMATION: Xaa is Tyr or His (ix) FEATURE:
        (A) NAME/KEY: misc-feature
        (B) LOCATION: 15
        (D) OTHER INFORMATION: Xaa is Gly or Ala (ix) FEATURE:
        (A) NAME/KEY: misc-feature
        (B) LOCATION: 17
        (D) OTHER INFORMATION: Xaa is Glu or Lys (ix) FEATURE:
        (A) NAME/KEY: misc-feature
        (B) LOCATION: 19
        (D) OTHER INFORMATION: Xaa is Cys or Met or Leu (ix) FEATURE:
        (A) NAME/KEY: misc-feature
        (B) LOCATION: 21
        (D) OTHER INFORMATION: Xaa is Trp or Leu (ix) FEATURE:
        (A) NAME/KEY: misc-feature
        (B) LOCATION: 34
        (D) OTHER INFORMATION: Xaa is Ser or Asn or Thr or Asp or His (ix) FEATURE:
        (A) NAME/KEY: misc-feature (B) LOCATION: 37
        (D) OTHER INFORMATION: Xaa is Pro or Gln (ix) FEATURE:
        (A) NAME/KEY: misc-feature
        (B) LOCATION: 38
        (D) OTHER INFORMATION: Xaa is Asn or Thr (ix) FEATURE:
        (A) NAME/KEY: misc-feature
        (B) LOCATION: 42
        (D) OTHER INFORMATION: Xaa is Arg or His (ix) FEATURE:
        (A) NAME/KEY: misc-feature
        (B) LOCATION: 43
        (D) OTHER INFORMATION: Xaa is Arg or Lys (ix) FEATURE:
        (A) NAME/KEY: misc-feature
        (B) LOCATION: 47
        (D) OTHER INFORMATION: Xaa is Leu or Val or Phe (ix) FEATURE:
        (A) NAME/KEY: misc-feature
        (B) LOCATION: 49
        (D) OTHER INFORMATION: Xaa is Lys or Arg (ix) FEATURE:
        (A) NAME/KEY: misc-feature
        (B) LOCATION: 54
        (D) OTHER INFORMATION: Xaa is Leu or Ile (ix) FEATURE:
        (A) NAME/KEY: misc-feature
        (B) LOCATION: 58
        (D) OTHER INFORMATION: Xaa is Phe or Leu (ix) FEATURE:
        (A) NAME/KEY: misc-feature
        (B) LOCATION: 62
        (D) OTHER INFORMATION: Xaa is Met or Ile (ix) FEATURE:
        (A) NAME/KEY: misc-feature
        (B) LOCATION: 63
        (D) OTHER INFORMATION: Xaa is Gly or Glu (ix) FEATURE:
        (A) NAME/KEY: misc-feature
        (B) LOCATION: 67
        (D) OTHER INFORMATION: Xaa is Leu or Val or Ile (ix) FEATURE:
        (A) NAME/KEY: misc-feature
        (B) LOCATION: 68
        (D) OTHER INFORMATION: Xaa is Val or Leu (ix) FEATURE:
        (A) NAME/KEY: misc-feature
        (B) LOCATION: 70
        (D) OTHER INFORMATION: Xaa is Ala or Gly (ix) FEATURE:
        (A) NAME/KEY: misc-feature
        (B) LOCATION: 72
        (D) OTHER INFORMATION: Xaa is Leu or Val or Ile (ix) FEATURE:
        (A) NAME/KEY: misc-feature
        (B) LOCATION: 75
        (D) OTHER INFORMATION: Xaa is Ala or Val (ix) FEATURE:
        (A) NAME/KEY: misc-feature
        (B) LOCATION: 76
        (D) OTHER INFORMATION: Xaa is Ala or Ser (xi) SEQUENCE DESCRIPTION: SEQ ID NO: 59:

```
Gly Xaa Xaa Trp Xaa Xaa Pro Gly Xaa Pro Trp Pro Leu Tyr Xaa Asn
1               5                   10                  15

Xaa Gly Xaa Gly Xaa Ala Gly Trp Leu Leu Ser Pro Arg Gly Ser Arg
            20                  25                  30

Pro Xaa Trp Gly Xaa Xaa Asp Pro Arg Xaa Xaa Ser Arg Asn Xaa Gly
        35                  40                  45

Xaa Val Ile Asp Thr Xaa Thr Cys Gly Xaa Ala Asp Leu Xaa Xaa Tyr
    50                  55                  60

Ile Pro Xaa Xaa Gly Xaa Pro Xaa Gly Gly Xaa Xaa
65                  70                  75
```

(2) INFORMATION FOR SEQ ID NO: 60:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Val or Ile (ix) FEATURE:
        (A) NAME/KEY: misc-feature
        (B) LOCATION: 3
        (D) OTHER INFORMATION: Xaa is Phe or Tyr (ix) FEATURE:
        (A) NAME/KEY: misc-feature
        (B) LOCATION: 4
        (D) OTHER INFORMATION: Xaa is Ala or Pro (ix) FEATURE:
        (A) NAME/KEY: misc-feature
        (B) LOCATION: 8
        (D) OTHER INFORMATION: Xaa is Leu or Ile (xi) SEQUENCE DESCRIPTION: SEQ ID NO: 60:

```
Xaa Asn Xaa Xaa Thr Gly Asn Xaa Pro Gly Cys Ser Phe Ser Ile
1               5                   10                  15
```

(2) INFORMATION FOR SEQ ID NO: 61:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 2
        (D) OTHER INFORMATION: Xaa is Phe or Leu (ix) FEATURE:
        (A) NAME/KEY: misc-feature
        (B) LOCATION: 6
        (D) OTHER INFORMATION: Xaa is Met or Ile (ix) FEATURE:
        (A) NAME/KEY: misc-feature
        (B) LOCATION: 7
        (D) OTHER INFORMATION: Xaa is Gly or Glu (ix) FEATURE:

```
        (A) NAME/KEY: misc-feature
        (B) LOCATION: 11
        (D) OTHER INFORMATION: Xaa is Leu or Val or Ile (ix) FEATURE:
        (A) NAME/KEY: misc-feature
        (B) LOCATION: 12
        (D) OTHER INFORMATION: Xaa is Val or Leu (ix) FEATURE:
        (A) NAME/KEY: misc-feature
        (B) LOCATION: 14
        (D) OTHER INFORMATION: Xaa is Ala or Gly (ix) FEATURE:
        (A) NAME/KEY: misc-feature
        (B) LOCATION: 16
        (D) OTHER INFORMATION: Xaa is Leu or Val or Ile (xi) SEQUENCE DESCRIPTION: SEQ ID NO: 61:

Gly Xaa Ala Asp Leu Xaa Xaa Tyr Ile Pro Xaa Xaa Gly Xaa Pro Xaa
1               5                   10                  15

(2) INFORMATION FOR SEQ ID NO: 62:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 2
        (D) OTHER INFORMATION: Xaa is Met or Ile (ix) FEATURE:
        (A) NAME/KEY: misc-feature
        (B) LOCATION: 3
        (D) OTHER INFORMATION: Xaa is Gly or Glu (ix) FEATURE:
        (A) NAME/KEY: misc-feature
        (B) LOCATION: 7
        (D) OTHER INFORMATION: Xaa is Leu or Val or Ile (ix) FEATURE:
        (A) NAME/KEY: misc-feature
        (B) LOCATION: 8
        (D) OTHER INFORMATION: Xaa is Val or Leu (ix) FEATURE:
        (A) NAME/KEY: misc-feature
        (B) LOCATION: 10
        (D) OTHER INFORMATION: Xaa is Ala or Gly (ix) FEATURE:
        (A) NAME/KEY: misc-feature
        (B) LOCATION: 12
        (D) OTHER INFORMATION: Xaa is Leu or Val or Ile (ix) FEATURE:
        (A) NAME/KEY: misc-feature
        (B) LOCATION: 15
        (D) OTHER INFORMATION: Xaa is Ala or Val (xi) SEQUENCE DESCRIPTION: SEQ ID NO: 62:

Gly Xaa Ala Asp Leu Xaa Xaa Tyr Ile Pro Xaa Xaa Gly Xaa Pro Xaa
1               5                   10                  15

(2) INFORMATION FOR SEQ ID NO: 63:

(i) SEQUENCE CHARACTERISTICS:
```

```
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Met or Ile (ix) FEATURE:
        (A) NAME/KEY: misc-feature
        (B) LOCATION: 2
        (D) OTHER INFORMATION: Xaa is Gly or Glu (ix) FEATURE:
        (A) NAME/KEY: misc-feature
        (B) LOCATION: 6
        (D) OTHER INFORMATION: Xaa is Leu or Val or Ile (ix) FEATURE:
        (A) NAME/KEY: misc-feature
        (B) LOCATION: 7
        (D) OTHER INFORMATION: Xaa is Val or Leu (ix) FEATURE:
        (A) NAME/KEY: misc-feature
        (B) LOCATION: 9
        (D) OTHER INFORMATION: Xaa is Ala or Gly (ix) FEATURE:
        (A) NAME/KEY: misc-feature
        (B) LOCATION: 11
        (D) OTHER INFORMATION: Xaa is Leu or Val or Ile (ix) FEATURE:
        (A) NAME/KEY: misc-feature
        (B) LOCATION: 14
        (D) OTHER INFORMATION: Xaa is Ala or Val (xi) SEQUENCE DESCRIPTION: SEQ ID NO: 63:

Xaa Xaa Tyr Ile Pro Xaa Xaa Gly Xaa Pro Xaa Gly Gly Xaa
1               5                  10

(2) INFORMATION FOR SEQ ID NO: 64:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 4
        (D) OTHER INFORMATION: Xaa is Leu or Val or Ile (ix) FEATURE:
        (A) NAME/KEY: misc-feature
        (B) LOCATION: 5
        (D) OTHER INFORMATION: Xaa is Val or Leu (ix) FEATURE:
        (A) NAME/KEY: misc-feature
        (B) LOCATION: 7
        (D) OTHER INFORMATION: Xaa is Ala or Gly (ix) FEATURE:
        (A) NAME/KEY: misc-feature
        (B) LOCATION: 9
        (D) OTHER INFORMATION: Xaa is Leu or Val or Ile (xi) SEQUENCE DESCRIPTION: SEQ ID NO: 64:
```

```
Tyr Ile Pro Xaa Xaa Gly Xaa Pro Xaa
1               5
```

(2) INFORMATION FOR SEQ ID NO: 65:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 3
        (D) OTHER INFORMATION: Xaa is Leu or Val or Ile (ix) FEATURE:
        (A) NAME/KEY: misc-feature
        (B) LOCATION: 4
        (D) OTHER INFORMATION: Xaa is Val or Leu (ix) FEATURE:
        (A) NAME/KEY: misc-feature
        (B) LOCATION: 6
        (D) OTHER INFORMATION: Xaa is Ala or Gly (ix) FEATURE:
        (A) NAME/KEY: misc-feature
        (B) LOCATION: 8
        (D) OTHER INFORMATION: Xaa is Leu or Val or Ile (xi) SEQUENCE DESCRIPTION: SEQ ID NO: 65:

```
Ile Pro Xaa Xaa Gly Xaa Pro Xaa
1               5
```

(2) INFORMATION FOR SEQ ID NO: 66:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Leu or Val or Ile (ix) FEATURE:
        (A) NAME/KEY: misc-feature
        (B) LOCATION: 2
        (D) OTHER INFORMATION: Xaa is Val or Leu (ix) FEATURE:
        (A) NAME/KEY: misc-feature
        (B) LOCATION: 4
        (D) OTHER INFORMATION: Xaa is Ala or Gly (ix) FEATURE:
        (A) NAME/KEY: misc-feature
        (B) LOCATION: 6
        (D) OTHER INFORMATION: Xaa is Leu or Val or Ile (ix) FEATURE:
        (A) NAME/KEY: misc-feature
        (B) LOCATION: 9
        (D) OTHER INFORMATION: Xaa is Ala or Val (xi) SEQUENCE DESCRIPTION: SEQ ID NO: 66:

```
Xaa Xaa Gly Xaa Pro Xaa Gly Gly Xaa
```

(2) INFORMATION FOR SEQ ID NO: 67:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

```
Leu Met Gly Tyr Ile Pro Leu Val Gly Ala Pro Leu Gly Ala Ala
 1               5                  10                  15

Arg Ala Leu Ala His Gly Val Arg Val Leu Glu Asp Gly Val Asn Tyr
             20                  25                  30

Ala Thr Gly Asn Leu Pro Gly Cys Ser Phe Ser Ile
             35                  40
```

(2) INFORMATION FOR SEQ ID NO: 68:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Val or Leu (ix) FEATURE:
        (A) NAME/KEY: misc-feature
        (B) LOCATION: 3
        (D) OTHER INFORMATION: Xaa is Ala or Gly (ix) FEATURE:
        (A) NAME/KEY: misc-feature
        (B) LOCATION: 5
        (D) OTHER INFORMATION: Xaa is Leu or Val or Ile (ix) FEATURE:
        (A) NAME/KEY: misc-feature
        (B) LOCATION: 8
        (D) OTHER INFORMATION: Xaa is Ala or Val (xi) SEQUENCE DESCRIPTION: SEQ ID NO: 68:

```
Xaa Gly Xaa Pro Xaa Gly Gly Xaa
 1               5
```

(2) INFORMATION FOR SEQ ID NO: 69:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 69:

```
Leu Met Gly Tyr Ile Pro Leu Val
 1               5
```

(2) INFORMATION FOR SEQ ID NO: 70:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 70:

Met Gly Tyr Ile Pro Leu Val
1               5

(2) INFORMATION FOR SEQ ID NO: 71:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 71:

Tyr Ile Pro Leu Val Gly Ala Pro Leu
1               5

(2) INFORMATION FOR SEQ ID NO: 72:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 72:

Ile Pro Leu Val Gly Ala Pro Leu
1               5

(2) INFORMATION FOR SEQ ID NO: 73:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 73:

Val Leu Glu Asp Ile Val Asn Tyr Ala Thr Gly Asn Leu Pro Gly Cys
1               5                  10                  15

Ser Phe Ser Ile
            20

(2) INFORMATION FOR SEQ ID NO: 74:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 2
            (D) OTHER INFORMATION: Xaa is Val or Ile

```
    (ix) FEATURE:
         (A) NAME/KEY: misc-feature
         (B) LOCATION: 4
         (D) OTHER INFORMATION: Xaa is Phe or Tyr (ix) FEATURE:
         (A) NAME/KEY: misc-feature
         (B) LOCATION: 5
         (D) OTHER INFORMATION: Xaa is Ala or Pro (ix) FEATURE:
         (A) NAME/KEY: misc-feature
         (B) LOCATION: 9
         (D) OTHER INFORMATION: Xaa is Leu or Ile (xi) SEQUENCE DESCRIPTION: SEQ ID NO: 74:

Gly Xaa Asn Xaa Xaa Thr Gly Asn Xaa
1               5

(2) INFORMATION FOR SEQ ID NO: 75:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: misc-feature
         (B) LOCATION: 1
         (D) OTHER INFORMATION: Xaa is Val or Ile (ix) FEATURE:
         (A) NAME/KEY: misc-feature
         (B) LOCATION: 3
         (D) OTHER INFORMATION: Xaa is Phe or Tyr (ix) FEATURE:
         (A) NAME/KEY: misc-feature
         (B) LOCATION: 4
         (D) OTHER INFORMATION: Xaa is Ala or Pro (ix) FEATURE:
         (A) NAME/KEY: misc-feature
         (B) LOCATION: 8
         (D) OTHER INFORMATION: Xaa is Leu or Ile (xi) SEQUENCE DESCRIPTION: SEQ ID NO: 75:

Xaa Asn Xaa Xaa Thr Gly Asn Xaa
1               5

(2) INFORMATION FOR SEQ ID NO: 76:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: misc-feature
         (B) LOCATION: 2
         (D) OTHER INFORMATION: Xaa is Leu or Ile (xi) SEQUENCE DESCRIPTION: SEQ ID NO: 76:

Asn Xaa Pro Gly Cys Ser Phe Ser Ile
1               5
```

(2) INFORMATION FOR SEQ ID NO: 77:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Leu or Ile (xi) SEQUENCE DESCRIPTION: SEQ ID NO: 77:

Xaa Pro Gly Cys Ser Phe Ser Ile
1           5

(2) INFORMATION FOR SEQ ID NO: 78:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 78:

Gly Val Asn Tyr Ala Thr Gly Asn Leu
1           5

(2) INFORMATION FOR SEQ ID NO: 79:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 79:

Gly Val Asn Tyr Ala Thr Gly Asn Leu
1           5

(2) INFORMATION FOR SEQ ID NO: 80:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

Asn Leu Pro Gly Cys Ser Phe Ser Ile
1           5

(2) INFORMATION FOR SEQ ID NO: 81:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

Leu Pro Gly Cys Ser Phe Ser Ile
1               5

(2) INFORMATION FOR SEQ ID NO: 82:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 1
            (D) OTHER INFORMATION: Xaa is Ala or Thr or Glu (ix) FEATURE:
            (A) NAME/KEY: misc-feature
            (B) LOCATION: 3
            (D) OTHER INFORMATION: Xaa is Ala or Glu (ix) FEATURE:
            (A) NAME/KEY: misc-feature
            (B) LOCATION: 8
            (D) OTHER INFORMATION: Xaa is Val or Ala or Leu (ix) FEATURE:
            (A) NAME/KEY: misc-feature
            (B) LOCATION: 9
            (D) OTHER INFORMATION: Xaa is Leu or Val or Ile (xi) SEQUENCE DESCRIPTION: SEQ ID NO: 82:

Xaa Leu Xaa His Gly Val Arg Xaa Xaa
1               5

(2) INFORMATION FOR SEQ ID NO: 83:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 2
            (D) OTHER INFORMATION: Xaa is Ala or Glu (ix) FEATURE:
            (A) NAME/KEY: misc-feature
            (B) LOCATION: 7
            (D) OTHER INFORMATION: Xaa is Val or Ala or Leu (ix) FEATURE:
            (A) NAME/KEY: misc-feature
            (B) LOCATION: 8
            (D) OTHER INFORMATION: Xaa is Leu or Val or Ile (xi) SEQUENCE DESCRIPTION: SEQ ID NO: 83:

Leu Xaa His Gly Val Arg Xaa Xaa
1               5

(2) INFORMATION FOR SEQ ID NO: 84:

(i) SEQUENCE CHARACTERISTICS:
            (A) LENGTH: 9 amino acids
            (B) TYPE: amino acid
            (C) STRANDEDNESS: single (D) TOPOLOGY: linear (ii) MOLECULE TYPE: peptide (ix) FEATURE:
            (A) NAME/KEY: misc-feature
            (B) LOCATION: 4
            (D) OTHER INFORMATION: Xaa is Val or Ala or Leu (ix) FEATURE:
            (A) NAME/KEY: misc-feature
            (B) LOCATION: 5
            (D) OTHER INFORMATION: Xaa is Leu or Val or Ile (ix) FEATURE:
            (A) NAME/KEY: misc-feature
            (B) LOCATION: 6
            (D) OTHER INFORMATION: Xaa is Glu or Gly (ix) FEATURE:
            (A) NAME/KEY: misc-feature
            (B) LOCATION: 9
            (D) OTHER INFORMATION: Xaa is Val or Ile (xi) SEQUENCE DESCRIPTION: SEQ ID NO: 84:

Gly Val Arg Xaa Xaa Xaa Asp Gly Xaa
1               5

(2) INFORMATION FOR SEQ ID NO: 85:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 3
            (D) OTHER INFORMATION: Xaa is Val or Ala or Leu (ix) FEATURE:
            (A) NAME/KEY: misc-feature
            (B) LOCATION: 4
            (D) OTHER INFORMATION: Xaa is Leu or Val or Ile (ix) FEATURE:
            (A) NAME/KEY: misc-feature
            (B) LOCATION: 5
            (D) OTHER INFORMATION: Xaa is Glu or Gly (ix) FEATURE:
            (A) NAME/KEY: misc-feature
            (B) LOCATION: 8
            (D) OTHER INFORMATION: Xaa is Val or Ile (xi) SEQUENCE DESCRIPTION: SEQ ID NO: 85:

Val Arg Xaa Xaa Xaa Asp Gly Xaa
1               5

(2) INFORMATION FOR SEQ ID NO: 86:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 2

(D) OTHER INFORMATION: Xaa is Val or Ala or Leu (ix) FEATURE:
            (A) NAME/KEY: misc-feature
            (B) LOCATION: 3
            (D) OTHER INFORMATION: Xaa is Leu or Val or Ile (ix) FEATURE:
            (A) NAME/KEY: misc-feature
            (B) LOCATION: 4
            (D) OTHER INFORMATION: Xaa is Glu or Gly (ix) FEATURE:
            (A) NAME/KEY: misc-feature
            (B) LOCATION: 7
            (D) OTHER INFORMATION: Xaa is Val or Ile (ix) FEATURE:
            (A) NAME/KEY: misc-feature
            (B) LOCATION: 9
            (D) OTHER INFORMATION: Xaa is Phe or Tyr (xi) SEQUENCE DESCRIPTION: SEQ ID NO: 86:

Arg Xaa Xaa Xaa Asp Gly Xaa Asn Xaa
1               5

(2) INFORMATION FOR SEQ ID NO: 87:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 1
            (D) OTHER INFORMATION: Xaa is Val or Ala or Leu (ix) FEATURE:
            (A) NAME/KEY: misc-feature
            (B) LOCATION: 2
            (D) OTHER INFORMATION: Xaa is Leu or Val or Ile (ix) FEATURE:
            (A) NAME/KEY: misc-feature
            (B) LOCATION: 3
            (D) OTHER INFORMATION: Xaa is Glu or Gly (ix) FEATURE:
            (A) NAME/KEY: misc-feature
            (B) LOCATION: 6
            (D) OTHER INFORMATION: Xaa is Val or Ile (ix) FEATURE:
            (A) NAME/KEY: misc-feature
            (B) LOCATION: 8
            (D) OTHER INFORMATION: Xaa is Phe or Tyr (xi) SEQUENCE DESCRIPTION: SEQ ID NO: 87:

Xaa Xaa Xaa Asp Gly Xaa Asn Xaa
1               5

(2) INFORMATION FOR SEQ ID NO: 88:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 88:

Ala Leu Ala His Gly Val Arg Val Leu
1               5

(2) INFORMATION FOR SEQ ID NO: 89:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 89:

Leu Ala His Gly Val Arg Val Leu
1               5

(2) INFORMATION FOR SEQ ID NO: 90:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

Val Arg Val Leu Glu Asp Gly Val
1               5

(2) INFORMATION FOR SEQ ID NO: 91:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 91:

Arg Val Leu Glu Asp Gly Val
1               5

(2) INFORMATION FOR SEQ ID NO: 92:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 92:

Val Leu Glu Asp Gly Val Asn Tyr
1               5

(2) INFORMATION FOR SEQ ID NO: 93:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 93:

Leu Glu Asp Gly Val Asn Tyr
1               5

(2) INFORMATION FOR SEQ ID NO: 94:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 94:

Leu Val Gly Ala Pro Leu Gly Gly Ala
1               5

(2) INFORMATION FOR SEQ ID NO: 95:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 95:

Val Gly Ala Pro Leu Gly Gly Ala
1               5

(2) INFORMATION FOR SEQ ID NO: 96:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 2
        (D) OTHER INFORMATION: Xaa is Leu or Val or Phe (ix) FEATURE:
        (A) NAME/KEY: misc-feature
        (B) LOCATION: 4
        (D) OTHER INFORMATION: Xaa is Lys or Arg (ix) FEATURE:
        (A) NAME/KEY: misc-feature
        (B) LOCATION: 9
        (D) OTHER INFORMATION: Xaa is Leu or Ile (xi) SEQUENCE DESCRIPTION: SEQ ID NO: 96:

Asn Xaa Gly Xaa Val Ile Asp Thr Xaa
1               5

(2) INFORMATION FOR SEQ ID NO: 97:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: misc-feature
         (B) LOCATION: 1
         (D) OTHER INFORMATION: Xaa is Leu or Val or Phe (ix) FEATURE:
         (A) NAME/KEY: misc-feature
         (B) LOCATION: 3
         (D) OTHER INFORMATION: Xaa is Lys or Arg (ix) FEATURE:
         (A) NAME/KEY: misc-feature
         (B) LOCATION: 8
         (D) OTHER INFORMATION: Xaa is Leu or Ile (xi) SEQUENCE DESCRIPTION: SEQ ID NO: 97:

Xaa Gly Xaa Val Ile Asp Thr Xaa
1               5

(2) INFORMATION FOR SEQ ID NO: 98:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

Asn Leu Gly Lys Val Ile Asp Thr Leu
1               5

(2) INFORMATION FOR SEQ ID NO: 99:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: misc-feature
         (B) LOCATION: 2
         (D) OTHER INFORMATION: Xaa is Arg or Lys (ix) FEATURE:
         (A) NAME/KEY: misc-feature
         (B) LOCATION: 3
         (D) OTHER INFORMATION: Xaa is Ala or Ser or Thr (ix) FEATURE:
         (A) NAME/KEY: misc-feature
         (B) LOCATION: 5
         (D) OTHER INFORMATION: Xaa is Ala or Gly (ix) FEATURE:
         (A) NAME/KEY: misc-feature
         (B) LOCATION: 6
         (D) OTHER INFORMATION: Xaa is Gln or Lys or Arg (ix) FEATURE:
         (A) NAME/KEY: misc-feature
         (B) LOCATION: 9
         (D) OTHER INFORMATION: Xaa is Tyr or His (ix) FEATURE:
         (A) NAME/KEY: misc-feature
         (B) LOCATION: 15
         (D) OTHER INFORMATION: Xaa is Gly or Ala (ix) FEATURE:
```

(A) NAME/KEY: misc-feature
            (B) LOCATION: 17
            (D) OTHER INFORMATION: Xaa is Glu or Lys (ix) FEATURE:
            (A) NAME/KEY: misc-feature
            (B) LOCATION: 19
            (D) OTHER INFORMATION: Xaa is Cys or Met or Leu (xi) SEQUENCE DESCRIPTION: SEQ ID NO: 99:

Gly Xaa Xaa Trp Xaa Xaa Pro Gly Xaa Pro Trp Pro Leu Tyr Xaa Asn
1               5                   10                  15

Xaa Gly Xaa Gly
            20

(2) INFORMATION FOR SEQ ID NO: 100:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 1
            (D) OTHER INFORMATION: Xaa is Ala or Ser or Thr (ix) FEATURE:
            (A) NAME/KEY: misc-feature
            (B) LOCATION: 3
            (D) OTHER INFORMATION: Xaa is Ala or Gly (ix) FEATURE:
            (A) NAME/KEY: misc-feature
            (B) LOCATION: 4
            (D) OTHER INFORMATION: Xaa is Gln or Lys or Arg (ix) FEATURE:
            (A) NAME/KEY: misc-feature
            (B) LOCATION: 7
            (D) OTHER INFORMATION: Xaa is Tyr or His (xi) SEQUENCE DESCRIPTION: SEQ ID NO: 100:

Xaa Trp Xaa Xaa Pro Gly Xaa Pro Trp
1               5

(2) INFORMATION FOR SEQ ID NO: 101:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 2
            (D) OTHER INFORMATION: Xaa is Ala or Gly (ix) FEATURE:
            (A) NAME/KEY: misc-feature
            (B) LOCATION: 3
            (D) OTHER INFORMATION: Xaa is Gln or Lys or Arg (ix) FEATURE:
            (A) NAME/KEY: misc-feature
            (B) LOCATION: 6
            (D) OTHER INFORMATION: Xaa is Tyr or His (xi) SEQUENCE DESCRIPTION: SEQ ID NO: 101:

Trp Xaa Xaa Pro Gly Xaa Pro Trp
1               5

(2) INFORMATION FOR SEQ ID NO: 102:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 102:

Thr Trp Ala Gln Pro Gly Tyr Pro Trp
1               5

(2) INFORMATION FOR SEQ ID NO: 103:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 103:

Trp Ala Gln Pro Gly Tyr Pro Trp
1               5

(2) INFORMATION FOR SEQ ID NO: 104:

(i) SEQUENCE CHARACTERISTICS:
       (A) LENGTH: 147 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 104:

Thr Pro Thr Val Ala Thr Thr Arg Asp Gly Lys Leu Pro Ala Thr Gln
1               5                   10                  15

Leu Arg Arg His Ile Asp Leu Leu Val Gly Ser Ala Thr Leu Cys Ser
            20                  25                  30

Ala Leu Tyr Val Gly Asp Leu Cys Gly Ser Val Gln Leu Phe Thr Phe
            35                  40                  45

Ser Pro Arg Arg His Trp Thr Thr Gln Gly Cys Asn Cys Ser Ile Tyr
    50                  55                  60

Pro Gly His Ile Thr Gly His Arg Met Ala Trp Asp Met Met Met Asn
65                  70                  75                  80

Trp Ser Pro Thr Ala Ala Leu Val Met Ala Gln Leu Leu Arg Ile Pro
                85                  90                  95

Gln Ala Ile Leu Asp Met Ile Ala Gly Ala His Trp Gly Val Leu Ala
            100                 105                 110

Gly Ile Ala Tyr Phe Ser Met Val Gly Asn Met Ala Lys Val Leu Val
            115                 120                 125

Val Leu Leu Leu Phe Ala Gly Val Asp Ala Glu Thr Ile Val Ser Gly
    130                 135                 140

Gly Gln Ala
145

(2) INFORMATION FOR SEQ ID NO: 105:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 105:

```
Thr Pro Thr Val Ala Thr Thr Arg Asp Gly Lys Leu Pro Ala Thr Gln
1               5                   10                  15

Leu Arg
```

(2) INFORMATION FOR SEQ ID NO: 106:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 106:

```
Leu Pro Ala Thr Gln Leu Arg Arg His Ile Asp Leu Leu Val Gly Ser
1               5                   10                  15

Ala Thr Leu Cys Ser Ala Leu Tyr Val Gly Asp Leu Cys Gly Ser Val
                20                  25                  30

Gln Leu Phe Thr Phe Ser Pro Arg Arg His Trp Thr Thr Gln Gly Cys
            35                  40                  45

Asn Cys Ser Ile Tyr Pro Gly His Ile Thr Gly His Arg Met Ala Trp
    50                  55                  60

Asp Met Met Met Asn Trp Ser Pro Thr Ala Ala Leu
65                  70                  75
```

(2) INFORMATION FOR SEQ ID NO: 107:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 107:

```
Met Asn Trp Ser Pro Thr Ala Ala Leu Val Met Ala Gln Leu Leu Arg
1               5                   10                  15

Ile Pro Gln Ala Ile Leu Asp Met Ile Ala Gly Ala His Trp Gly Val
                20                  25                  30

Leu Ala Gly Ile Ala Tyr Phe Ser Met Val Gly Asn Met Ala Lys Val
            35                  40                  45

Leu Val Val Leu Leu Leu Phe Ala Gly Val Asp Ala Glu Thr Ile Val
    50                  55                  60

Ser Gly Gly Gln Ala
65
```

(2) INFORMATION FOR SEQ ID NO: 108:

(i) SEQUENCE CHARACTERISTICS:

```
       (A) LENGTH: 70 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: misc-feature
       (B) LOCATION: 2
       (D) OTHER INFORMATION: Xaa is Gly or Arg (ix) FEATURE:
       (A) NAME/KEY: misc-feature
       (B) LOCATION: 3
       (D) OTHER INFORMATION: Xaa is Gly or Ala or Lys (ix) FEATURE:
       (A) NAME/KEY: misc-feature
       (B) LOCATION: 4
       (D) OTHER INFORMATION: Xaa is Ala or Val or Gly or Ser or Asp (ix) FEATURE:
       (A) NAME/KEY: misc-feature
       (B) LOCATION: 5
       (D) OTHER INFORMATION: Xaa is Gly or Phe or Tyr (ix) FEATURE:
       (A) NAME/KEY: misc-feature
       (B) LOCATION: 7
       (D) OTHER INFORMATION: Xaa is Asn or His or Arg or Leu or Ala
       or Ser (ix) FEATURE:
       (A) NAME/KEY: misc-feature
       (B) LOCATION: 8
       (D) OTHER INFORMATION: Xaa is Thr or Ser (ix) FEATURE:
       (A) NAME/KEY: misc-feature
       (B) LOCATION: 9
       (D) OTHER INFORMATION: Xaa is Met or Ile or bond (ix) FEATURE:
       (A) NAME/KEY: misc-feature
       (B) LOCATION: 10
       (D) OTHER INFORMATION: Xaa is Asp or bond (ix) FEATURE:
       (A) NAME/KEY: misc-feature
       (B) LOCATION: 12
       (D) OTHER INFORMATION: Xaa is His or Leu or Val or Thr or Ile (ix) FEATURE:
       (A) NAME/KEY: misc-feature
       (B) LOCATION: 21
       (D) OTHER INFORMATION: Xaa is His or Tyr (ix) FEATURE:
       (A) NAME/KEY: misc-feature
       (B) LOCATION: 23
       (D) OTHER INFORMATION: Xaa is Asp or Glu (ix) FEATURE:
       (A) NAME/KEY: misc-feature
       (B) LOCATION: 24
       (D) OTHER INFORMATION: Xaa is Ala or Thr (ix) FEATURE:
       (A) NAME/KEY: misc-feature
       (B) LOCATION: 27
       (D) OTHER INFORMATION: Xaa is Ser or Thr or Ile or Leu (ix) FEATURE:
       (A) NAME/KEY: misc-feature
       (B) LOCATION: 28
       (D) OTHER INFORMATION: Xaa is Arg or Lys (ix) FEATURE:
```

```
            (A) NAME/KEY: misc-feature
            (B) LOCATION: 31
            (D) OTHER INFORMATION: Xaa is Ser or Ala (ix) FEATURE:
            (A) NAME/KEY: misc-feature
            (B) LOCATION: 34
            (D) OTHER INFORMATION: Xaa is Trp or Leu (ix) FEATURE:
            (A) NAME/KEY: misc-feature
            (B) LOCATION: 35
            (D) OTHER INFORMATION: Xaa is Ile or Leu (ix) FEATURE:
            (A) NAME/KEY: misc-feature
            (B) LOCATION: 40
            (D) OTHER INFORMATION: Xaa is Leu or Met or Ile (ix) FEATURE:
            (A) NAME/KEY: misc-feature
            (B) LOCATION: 41
            (D) OTHER INFORMATION: Xaa is Val or Ile (ix) FEATURE:
            (A) NAME/KEY: misc-feature
            (B) LOCATION: 54
            (D) OTHER INFORMATION: Xaa is Ile or Val or Phe or Leu (ix) FEATURE:
            (A) NAME/KEY: misc-feature
            (B) LOCATION: 56
            (D) OTHER INFORMATION: Xaa is Tyr or Phe (ix) FEATURE:
            (A) NAME/KEY: misc-feature
            (B) LOCATION: 57
            (D) OTHER INFORMATION: Xaa is Thr or Ser or Ala (ix) FEATURE:
            (A) NAME/KEY: misc-feature
            (B) LOCATION: 58
            (D) OTHER INFORMATION: Xaa is Ile or Val (ix) FEATURE:
            (A) NAME/KEY: misc-feature
            (B) LOCATION: 61
            (D) OTHER INFORMATION: Xaa is Ile or Val or Ala (ix) FEATURE:
            (A) NAME/KEY: misc-feature
            (B) LOCATION: 64
            (D) OTHER INFORMATION: Xaa is Tyr or Phe (xi) SEQUENCE DESCRIPTION: SEQ ID NO: 108:

Ile Xaa Xaa Xaa Xaa Asn Xaa Xaa Xaa Leu Xaa Cys Pro Thr Asp
1               5                  10                  15

Cys Phe Arg Lys Xaa Pro Xaa Xaa Thr Tyr Xaa Xaa Cys Gly Xaa Gly
            20                  25                  30

Pro Xaa Xaa Thr Pro Arg Cys Xaa Xaa Asp Tyr Pro Tyr Arg Leu Trp
        35                  40                  45

His Tyr Pro Cys Thr Xaa Asn Xaa Xaa Xaa Phe Lys Xaa Arg Met Xaa
    50                  55                  60

Val Gly Gly Val Glu His
65                  70

(2) INFORMATION FOR SEQ ID NO: 109:

(i) SEQUENCE CHARACTERISTICS:
            (A) LENGTH: 9 amino acids
            (B) TYPE: amino acid
            (C) STRANDEDNESS: single
            (D) TOPOLOGY: linear
```

```
    (ii) MOLECULE TYPE: peptide (ix) FEATURE:
         (A) NAME/KEY: misc-feature
         (B) LOCATION: 1
         (D) OTHER INFORMATION: Xaa is Gln or Ser or Tyr (ix) FEATURE:
         (A) NAME/KEY: misc-feature
         (B) LOCATION: 3
         (D) OTHER INFORMATION: Xaa is Ile or Val (ix) FEATURE:
         (A) NAME/KEY: misc-feature
         (B) LOCATION: 5
         (D) OTHER INFORMATION: Xaa is Thr or Ser (xi) SEQUENCE DESCRIPTION: SEQ ID NO: 109:

Xaa Leu Xaa Asn Xaa Asn Gly Ser Trp
1               5

(2) INFORMATION FOR SEQ ID NO: 110:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: misc-feature
         (B) LOCATION: 2
         (D) OTHER INFORMATION: Xaa is Ile or Val (ix) FEATURE:
         (A) NAME/KEY: misc-feature
         (B) LOCATION: 4
         (D) OTHER INFORMATION: Xaa is Thr or Ser (xi) SEQUENCE DESCRIPTION: SEQ ID NO: 110:

Leu Xaa Asn Xaa Asn Gly Ser Trp
1               5

(2) INFORMATION FOR SEQ ID NO: 111:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: misc-feature
         (B) LOCATION: 4
         (D) OTHER INFORMATION: Xaa is Leu or Ile (ix) FEATURE:
         (A) NAME/KEY: misc-feature
         (B) LOCATION: 6
         (D) OTHER INFORMATION: Xaa is Ser or Arg (xi) SEQUENCE DESCRIPTION: SEQ ID NO: 111:

Ser Trp His Xaa Asn Xaa Thr Ala Leu
1               5

(2) INFORMATION FOR SEQ ID NO: 112:

(i) SEQUENCE CHARACTERISTICS:
```

```
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 4
        (D) OTHER INFORMATION: Xaa is Leu or Ile (ix) FEATURE:
        (A) NAME/KEY: misc-feature
        (B) LOCATION: 6
        (D) OTHER INFORMATION: Xaa is Ser or Arg (xi) SEQUENCE DESCRIPTION: SEQ ID NO: 112:

Ser Trp His Xaa Asn Xaa Thr Ala Leu
1               5

(2) INFORMATION FOR SEQ ID NO: 113:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 113:

Gln Leu Ile Asn Thr Asn Gly Ser Trp
1               5

(2) INFORMATION FOR SEQ ID NO: 114:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 114:

Leu Ile Asn Thr Asn Gly Ser Trp
1               5

(2) INFORMATION FOR SEQ ID NO: 115:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 115:

Ser Trp His Ile Asn Ser Thr Ala Leu
1               5

(2) INFORMATION FOR SEQ ID NO: 116:

(i) SEQUENCE CHARACTERISTICS:
        (A) LENGTH: 8 amino acids
        (B) TYPE: amino acid
        (C) STRANDEDNESS: single
        (D) TOPOLOGY: linear
```

```
    (ii) MOLECULE TYPE: peptide (xi) SEQUENCE DESCRIPTION: SEQ ID NO: 116:

Trp His Ile Asn Ser Thr Ala Leu
1               5

(2) INFORMATION FOR SEQ ID NO: 117:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 117:

Trp His Ile Asn Ser Thr Ala Leu
1               5

(2) INFORMATION FOR SEQ ID NO: 118:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 118:

Gly Gly Val Ala Ala Arg Ala Leu Ala His Gly Val Arg Val Leu Glu
1               5                   10                  15

Asp Gly Val Asn Tyr
            20

(2) INFORMATION FOR SEQ ID NO: 119:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Thr or Ser (ix) FEATURE:
        (A) NAME/KEY: misc-feature
        (B) LOCATION: 2
        (D) OTHER INFORMATION: Xaa is Met or Ile (ix) FEATURE:
        (A) NAME/KEY: misc-feature
        (B) LOCATION: 3
        (D) OTHER INFORMATION: Xaa is Asp (ix) FEATURE:
        (A) NAME/KEY: misc-feature
        (B) LOCATION: 5
        (D) OTHER INFORMATION: Xaa is His or Leu or Val or Thr or Ile (xi) SEQUENCE DESCRIPTION: SEQ ID NO: 119:

Xaa Glx Glx Leu Xaa Cys Pro Thr Asp Cys Phe
1               5                   10
```

(2) INFORMATION FOR SEQ ID NO: 120:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 4
        (D) OTHER INFORMATION: Xaa is His or Tyr (ix) FEATURE:
        (A) NAME/KEY: misc-feature
        (B) LOCATION: 6
        (D) OTHER INFORMATION: Xaa is Asp or Glu (ix) FEATURE:
        (A) NAME/KEY: misc-feature
        (B) LOCATION: 7
        (D) OTHER INFORMATION: Xaa is Ala or Thr (xi) SEQUENCE DESCRIPTION: SEQ ID NO: 120:

Phe Arg Lys Xaa Pro Xaa Xaa Thr Tyr
1               5

(2) INFORMATION FOR SEQ ID NO: 121:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature
        (B) LOCATION: 1
        (D) OTHER INFORMATION: Xaa is Trp or Leu (ix) FEATURE:
        (A) NAME/KEY: misc-feature
        (B) LOCATION: 2
        (D) OTHER INFORMATION: Xaa is Ile or Leu (ix) FEATURE:
        (A) NAME/KEY: misc-feature
        (B) LOCATION: 7
        (D) OTHER INFORMATION: Xaa is Leu or Met or Ile (ix) FEATURE:
        (A) NAME/KEY: misc-feature
        (B) LOCATION: 8
        (D) OTHER INFORMATION: Xaa is Val or Ile (xi) SEQUENCE DESCRIPTION: SEQ ID NO: 121:

Xaa Xaa Thr Pro Arg Cys Xaa Xaa
1               5

(2) INFORMATION FOR SEQ ID NO: 122:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc-feature

```
            (B) LOCATION: 1
            (D) OTHER INFORMATION: Xaa is Leu or Met or Ile (ix) FEATURE:
            (A) NAME/KEY: misc-feature
            (B) LOCATION: 2
            (D) OTHER INFORMATION: Xaa is Val or Ile (xi) SEQUENCE DESCRIPTION: SEQ ID NO: 122:

Xaa Xaa Asp Tyr Pro Tyr Arg Leu
1               5

(2) INFORMATION FOR SEQ ID NO: 123:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 1
            (D) OTHER INFORMATION: Xaa is Val or Ile (xi) SEQUENCE DESCRIPTION: SEQ ID NO: 123:

Xaa Asp Tyr Pro Tyr Arg Leu Trp
1               5

(2) INFORMATION FOR SEQ ID NO: 124:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 124:

Tyr Pro Tyr Arg Leu Trp His Tyr
1               5

(2) INFORMATION FOR SEQ ID NO: 125:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 8
            (D) OTHER INFORMATION: Xaa is Ile or Val or Phe or Leu (xi) SEQUENCE DESCRIPTION: SEQ ID NO: 125:

Leu Trp His Tyr Pro Cys Thr Xaa
1               5

(2) INFORMATION FOR SEQ ID NO: 126:

(i) SEQUENCE CHARACTERISTICS:
            (A) LENGTH: 8 amino acids
            (B) TYPE: amino acid
            (C) STRANDEDNESS: single
            (D) TOPOLOGY: linear
```

```
        (ii) MOLECULE TYPE: peptide (ix) FEATURE:
             (A) NAME/KEY: misc-feature
             (B) LOCATION: 1
             (D) OTHER INFORMATION: Xaa is Ile or Val or Phe or Leu (ix) FEATURE:
             (A) NAME/KEY: misc-feature
             (B) LOCATION: 3
             (D) OTHER INFORMATION: Xaa is Tyr or Phe (ix) FEATURE:
             (A) NAME/KEY: misc-feature
             (B) LOCATION: 4
             (D) OTHER INFORMATION: Xaa is Thr or Ser or Ala (ix) FEATURE:
             (A) NAME/KEY: misc-feature
             (B) LOCATION: 5
             (D) OTHER INFORMATION: Xaa is Ile or Val (ix) FEATURE:
             (A) NAME/KEY: misc-feature
             (B) LOCATION: 8
             (D) OTHER INFORMATION: Xaa is Ile or Val or Ala (xi) SEQUENCE DESCRIPTION: SEQ ID NO: 126:

Xaa Asn Xaa Xaa Xaa Phe Lys Xaa
1               5

(2) INFORMATION FOR SEQ ID NO: 127:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: misc-feature
             (B) LOCATION: 1
             (D) OTHER INFORMATION: Xaa is Tyr or Phe (ix) FEATURE:
             (A) NAME/KEY: misc-feature
             (B) LOCATION: 2
             (D) OTHER INFORMATION: Xaa is Thr or Ser or Ala (ix) FEATURE:
             (A) NAME/KEY: misc-feature
             (B) LOCATION: 3
             (D) OTHER INFORMATION: Xaa is Ile or Val (ix) FEATURE:
             (A) NAME/KEY: misc-feature
             (B) LOCATION: 6
             (D) OTHER INFORMATION: Xaa is Ile or Val or Ala (xi) SEQUENCE DESCRIPTION: SEQ ID NO: 127:

Xaa Xaa Xaa Phe Lys Xaa Arg Met
1               5

(2) INFORMATION FOR SEQ ID NO: 128:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide
```

```
    (ix) FEATURE:
          (A) NAME/KEY: misc-feature
          (B) LOCATION: 1
          (D) OTHER INFORMATION: Xaa is Ile or Val (ix) FEATURE:
          (A) NAME/KEY: misc-feature
          (B) LOCATION: 4
          (D) OTHER INFORMATION: Xaa is Ile or Val or Ala (ix) FEATURE:
          (A) NAME/KEY: misc-feature
          (B) LOCATION: 7
          (D) OTHER INFORMATION: Xaa is Tyr or Phe (xi) SEQUENCE DESCRIPTION: SEQ ID NO: 128:

Xaa Phe Lys Xaa Arg Met Xaa Val
1               5

(2) INFORMATION FOR SEQ ID NO: 129:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: misc-feature
          (B) LOCATION: 1
          (D) OTHER INFORMATION: Xaa is Ile or Val or Ala (ix) FEATURE:
          (A) NAME/KEY: misc-feature
          (B) LOCATION: 4
          (D) OTHER INFORMATION: Xaa is Tyr or Phe (xi) SEQUENCE DESCRIPTION: SEQ ID NO: 129:

Xaa Arg Met Xaa Val Gly Gly Val
1               5

(2) INFORMATION FOR SEQ ID NO: 130:

(i) SEQUENCE CHARACTERISTICS:
          (A) LENGTH: 22 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: misc-feature
          (B) LOCATION: 2
          (D) OTHER INFORMATION: Xaa is Gly or Arg (ix) FEATURE:
          (A) NAME/KEY: misc-feature
          (B) LOCATION: 3
          (D) OTHER INFORMATION: Xaa is Gly or Ala or Lys (ix) FEATURE:
          (A) NAME/KEY: misc-feature
          (B) LOCATION: 4
          (D) OTHER INFORMATION: Xaa is Ala or Val or Gly or Ser or Asp (ix) FEATURE:
          (A) NAME/KEY: misc-feature
          (B) LOCATION: 5
          (D) OTHER INFORMATION: Xaa is Gly or Phe or Tyr (ix) FEATURE:
```

```
            (A) NAME/KEY: misc-feature
            (B) LOCATION: 7
            (D) OTHER INFORMATION: Xaa is Asn or His or Arg or Leu or Ala
            or Ser (ix) FEATURE:
            (A) NAME/KEY: misc-feature
            (B) LOCATION: 8
            (D) OTHER INFORMATION: Xaa is Thr or Ser (ix) FEATURE:
            (A) NAME/KEY: misc-feature
            (B) LOCATION: 9
            (D) OTHER INFORMATION: Xaa is Met or Ile (ix) FEATURE:
            (A) NAME/KEY: misc-feature
            (B) LOCATION: 10
            (D) OTHER INFORMATION: Xaa is Asp (ix) FEATURE:
            (A) NAME/KEY: misc-feature
            (B) LOCATION: 12
            (D) OTHER INFORMATION: Xaa is His or Leu or Val or Thr or Ile (ix) FEATURE:
            (A) NAME/KEY: misc-feature
            (B) LOCATION: 21
            (D) OTHER INFORMATION: Xaa is His or Tyr (xi) SEQUENCE DESCRIPTION: SEQ ID NO: 130:

Ile Xaa Xaa Xaa Xaa Asn Xaa Xaa Glx Glx Leu Xaa Cys Pro Thr Asp
1               5                   10                  15

Cys Phe Arg Lys Xaa Pro
            20

(2) INFORMATION FOR SEQ ID NO: 131:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: misc-feature
            (B) LOCATION: 7
            (D) OTHER INFORMATION: Xaa is His or Tyr (ix) FEATURE:
            (A) NAME/KEY: misc-feature
            (B) LOCATION: 9
            (D) OTHER INFORMATION: Xaa is Asp or Glu (ix) FEATURE:
            (A) NAME/KEY: misc-feature
            (B) LOCATION: 10
            (D) OTHER INFORMATION: Xaa is Ala or Thr (ix) FEATURE:
            (A) NAME/KEY: misc-feature
            (B) LOCATION: 13
            (D) OTHER INFORMATION: Xaa is Ser or Thr or Ile or Leu (ix) FEATURE:
            (A) NAME/KEY: misc-feature
            (B) LOCATION: 14
            (D) OTHER INFORMATION: Xaa is Arg or Lys (ix) FEATURE:
            (A) NAME/KEY: misc-feature
            (B) LOCATION: 17
            (D) OTHER INFORMATION: Xaa is Ser or Ala
```

(ix) FEATURE:
              (A) NAME/KEY: misc-feature
              (B) LOCATION: 20
              (D) OTHER INFORMATION: Xaa is Trp or Leu (xi) SEQUENCE DESCRIPTION: SEQ ID NO: 131:

Thr Asp Cys Phe Arg Lys Xaa Pro Xaa Xaa Thr Tyr Xaa Xaa Cys Gl
1               5                  10                  15

Xaa Gly Pro Xaa
            20

(2) INFORMATION FOR SEQ ID NO: 132:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: misc-feature
              (B) LOCATION: 1
              (D) OTHER INFORMATION: Xaa is Ser or Thr or Ile or Leu (ix) FEATURE:
              (A) NAME/KEY: misc-feature
              (B) LOCATION: 2
              (D) OTHER INFORMATION: Xaa is Arg or Lys (ix) FEATURE:
              (A) NAME/KEY: misc-feature
              (B) LOCATION: 5
              (D) OTHER INFORMATION: Xaa is Ser or Ala (ix) FEATURE:
              (A) NAME/KEY: misc-feature
              (B) LOCATION: 8
              (D) OTHER INFORMATION: Xaa is Trp or Leu (ix) FEATURE:
              (A) NAME/KEY: misc-feature
              (B) LOCATION: 9
              (D) OTHER INFORMATION: Xaa is Ile or Leu (ix) FEATURE:
              (A) NAME/KEY: misc-feature
              (B) LOCATION: 14
              (D) OTHER INFORMATION: Xaa is Leu or Met or Ile (ix) FEATURE:
              (A) NAME/KEY: misc-feature
              (B) LOCATION: 15
              (D) OTHER INFORMATION: Xaa is Val or Ile (xi) SEQUENCE DESCRIPTION: SEQ ID NO: 132:

Xaa Xaa Cys Gly Xaa Gly Pro Xaa Xaa Thr Pro Arg Cys Xaa Xaa Asp
1               5                  10                  15

Tyr Pro Tyr Arg
            20

(2) INFORMATION FOR SEQ ID NO: 133:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (ix) FEATURE:

(A) NAME/KEY: misc-feature
                (B) LOCATION: 2
                (D) OTHER INFORMATION: Xaa is Leu or Met or Ile (ix) FEATURE:
                (A) NAME/KEY: misc-feature
                (B) LOCATION: 3
                (D) OTHER INFORMATION: Xaa is Val or Ile (ix) FEATURE:
                (A) NAME/KEY: misc-feature
                (B) LOCATION: 16
                (D) OTHER INFORMATION: Xaa is Ile or Val or Phe or Leu (ix) FEATURE:
                (A) NAME/KEY: misc-feature
                (B) LOCATION: 18
                (D) OTHER INFORMATION: Xaa is Tyr or Phe (ix) FEATURE:
                (A) NAME/KEY: misc-feature
                (B) LOCATION: 19
                (D) OTHER INFORMATION: Xaa is Thr or Ser or Ala (ix) FEATURE:
                (A) NAME/KEY: misc-feature
                (B) LOCATION: 20
                (D) OTHER INFORMATION: Xaa is Ile or Val (xi) SEQUENCE DESCRIPTION: SEQ ID NO: 133:

Cys Xaa Xaa Asp Tyr Pro Tyr Arg Leu Trp His Tyr Pro Cys Thr Xaa
1               5                   10                  15

Asn Xaa Xaa Xaa
            20

(2) INFORMATION FOR SEQ ID NO: 134:

(i) SEQUENCE CHARACTERISTICS:
                (A) LENGTH: 20 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: misc-feature
                (B) LOCATION: 4
                (D) OTHER INFORMATION: Xaa is Ile or Val or Phe or Leu (ix) FEATURE:
                (A) NAME/KEY: misc-feature
                (B) LOCATION: 6
                (D) OTHER INFORMATION: Xaa is Tyr or Phe (ix) FEATURE:
                (A) NAME/KEY: misc-feature
                (B) LOCATION: 7
                (D) OTHER INFORMATION: Xaa is Thr or Ser or Ala (ix) FEATURE:
                (A) NAME/KEY: misc-feature
                (B) LOCATION: 8
                (D) OTHER INFORMATION: Xaa is Ile or Val (ix) FEATURE:
                (A) NAME/KEY: misc-feature
                (B) LOCATION: 11
                (D) OTHER INFORMATION: Xaa is Ile or Val or Ala (ix) FEATURE:
                (A) NAME/KEY: misc-feature
                (B) LOCATION: 14
                (D) OTHER INFORMATION: Xaa is Tyr or Phe (xi) SEQUENCE DESCRIPTION: SEQ ID NO: 134:

```
Pro Cys Thr Xaa Asn Xaa Xaa Xaa Phe Lys Xaa Arg Met Xaa Val Gly
 1               5                  10                  15

Gly Val Glu His
             20
```

(2) INFORMATION FOR SEQ ID NO: 135:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 135:

```
Val Ala Lys Ala Val Asp Phe Val
 1               5
```

(2) INFORMATION FOR SEQ ID NO: 136:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 136:

```
Val Ala Lys Ala Val Asp Phe Ile
 1               5
```

(2) INFORMATION FOR SEQ ID NO: 137:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 137:

```
Val Glu Ser Met Glu Thr Thr Met
 1               5
```

(2) INFORMATION FOR SEQ ID NO: 138:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 138:

```
Ala Val Pro Gln Thr Phe Gln Val
 1               5
```

(2) INFORMATION FOR SEQ ID NO: 139:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 139:

Tyr Ala Ala Gln Gly Tyr Lys Val
1               5

(2) INFORMATION FOR SEQ ID NO: 140:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 140:

Val Leu Val Leu Asn Pro Ser Val Ala
1               5

(2) INFORMATION FOR SEQ ID NO: 141:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 141:

Tyr Met Ser Lys Ala His Gly Val
1               5

(2) INFORMATION FOR SEQ ID NO: 142:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 142:

Ile Arg Thr Gly Val Arg Thr Ile
1               5

(2) INFORMATION FOR SEQ ID NO: 143:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 143:

Tyr Ser Thr Tyr Gly Lys Phe Leu
1               5

(2) INFORMATION FOR SEQ ID NO: 144:

(i) SEQUENCE CHARACTERISTICS:
            (A) LENGTH: 8 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO: 144:

Ile Leu Gly Ile Gly Thr Val Leu
1               5

(2) INFORMATION FOR SEQ ID NO: 145:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 145:

Val Thr Val Pro His Pro Asn Ile
1               5

(2) INFORMATION FOR SEQ ID NO: 146:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 146:

Ile Pro Phe Tyr Gly Lys Ala Ile
1               5

(2) INFORMATION FOR SEQ ID NO: 147:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 147:

Phe Tyr Gly Lys Ala Ile Pro Ile
1               5

(2) INFORMATION FOR SEQ ID NO: 148:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 148:

Val Ile Lys Gly Gly Arg His Leu
1               5

(2) INFORMATION FOR SEQ ID NO: 149:

(i) SEQUENCE CHARACTERISTICS:
            (A) LENGTH: 8 amino acids
            (B) TYPE: amino acid (C) STRANDEDNESS: single
            (D) TOPOLOGY: linear (ii) MOLECULE TYPE: peptide (xi) SEQUENCE DESCRIPTION: SEQ ID NO: 149:

Ile Lys Gly Gly Arg His Leu Ile
1               5

(2) INFORMATION FOR SEQ ID NO: 150:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 150:

Phe Cys His Ser Lys Lys Lys Cys
1               5

(2) INFORMATION FOR SEQ ID NO: 151:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 151:

Cys Asp Glu Leu Ala Ala Lys Leu
1               5

(2) INFORMATION FOR SEQ ID NO: 152:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 152:

Leu Ala Ala Lys Leu Ser Gly Phe Gly
1               5

(2) INFORMATION FOR SEQ ID NO: 153:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 153:

Ser Gly Phe Gly Ile Asn Ala Val
1               5

(2) INFORMATION FOR SEQ ID NO: 154:

(i) SEQUENCE CHARACTERISTICS:
            (A) LENGTH: 8 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 154:

Phe Gly Ile Asn Ala Val Ala Tyr
1               5

(2) INFORMATION FOR SEQ ID NO: 155:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 155:

Tyr Arg Gly Leu Asp Val Ser Val
1               5

(2) INFORMATION FOR SEQ ID NO: 156:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 156:

Val Ile Pro Thr Ser Gly Asp Val
1               5

(2) INFORMATION FOR SEQ ID NO: 157:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 157:

Ile Pro Thr Ser Gly Asp Val Val
1               5

(2) INFORMATION FOR SEQ ID NO: 158:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 158:

Val Val Val Ala Thr Asp Ala Leu
1               5

(2) INFORMATION FOR SEQ ID NO: 159:

(i) SEQUENCE CHARACTERISTICS:

(A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 159:

Val Val Ala Thr Asp Ala Leu Met
1               5

(2) INFORMATION FOR SEQ ID NO: 160:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 160:

Met Thr Gly Phe Thr Gly Asp Phe
1               5

(2) INFORMATION FOR SEQ ID NO: 161:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 161:

Phe Thr Gly Asp Phe Asp Ser Val
1               5

(2) INFORMATION FOR SEQ ID NO: 162:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 162:

Val Ile Asp Cys Asn Thr Cys Val
1               5

(2) INFORMATION FOR SEQ ID NO: 163:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 163:

Ala Leu Met Gly Tyr Ile Pro Leu Val
1               5

(2) INFORMATION FOR SEQ ID NO: 164:

```
    (i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 164:

Tyr Gln Val Arg Asn Ser Thr Gly Leu Tyr His Val Thr Asn Asp Cys
1               5                   10                  15

Pro Asn Ser Ser Ile Val Tyr Glu Ala His Asp Ala Ile Leu His Thr
            20                  25                  30

Pro Gly Cys Val Pro Cys Val Arg Glu Gly Asn
        35                  40

(2) INFORMATION FOR SEQ ID NO: 165:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 165:

Gln Val Arg Asn Ser Thr Gly Leu Tyr His Val Thr Asn Asp Cys Pro
1               5                   10                  15

Asn Ser Ser Ile Val Tyr Glu Ala His Asp Ala Ile Leu His Thr Pro
            20                  25                  30

Gly Cys Val Pro Cys Val Arg Glu Gly Asn
        35                  40

(2) INFORMATION FOR SEQ ID NO: 166:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 166:

Lys Leu Val Ala Leu Gly Ile Asn Ala Val
1               5                   10

(2) INFORMATION FOR SEQ ID NO: 167:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 167:

Ala Ser Arg Cys Trp Val Ala Met
1               5

(2) INFORMATION FOR SEQ ID NO: 168:

(i) SEQUENCE CHARACTERISTICS:
        (A) LENGTH: 13 amino acids
        (B) TYPE: amino acid
```

(C) STRANDEDNESS: single
        (D) TOPOLOGY: linear (ii) MOLECULE TYPE: peptide (xi) SEQUENCE DESCRIPTION: SEQ ID NO: 168:

Leu Met Ala Leu Thr Leu Ser Pro Tyr Tyr Lys Arg Tyr
 1               5                  10

(2) INFORMATION FOR SEQ ID NO: 169:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 169:

Arg Ala Leu Ala His Gly Val Arg Val Leu Glu Asp Gly
 1               5                  10

(2) INFORMATION FOR SEQ ID NO: 170:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 170:

Arg Met Ala Trp Asp Met Met
 1               5

(2) INFORMATION FOR SEQ ID NO: 171:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 171:

Pro Thr Asp Cys Phe Arg Lys His Pro
 1               5

(2) INFORMATION FOR SEQ ID NO: 172:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 172:

Tyr Pro Tyr Arg Leu Trp His
 1               5

(2) INFORMATION FOR SEQ ID NO: 173:

(i) SEQUENCE CHARACTERISTICS:
        (A) LENGTH: 7 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 173:

Gly Lys Ser Thr Lys Val Pro
 1               5

(2) INFORMATION FOR SEQ ID NO: 174:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 174:

Pro Ser Val Ala Ala Thr
 1               5

(2) INFORMATION FOR SEQ ID NO: 175:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 175:

Ile Gly Thr Val Leu Asp Gln Ala Glu
 1               5

(2) INFORMATION FOR SEQ ID NO: 176:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 176:

Ala Val Ala Tyr Tyr Arg
 1               5

(2) INFORMATION FOR SEQ ID NO: 177:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 177:

Ala Ser Arg Cys Trp Val Ala Met
 1               5

(2) INFORMATION FOR SEQ ID NO: 178:

(i) SEQUENCE CHARACTERISTICS:
```

```
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 178:

Thr Gly Asp Phe Asp Ser Val Ile Asp
  1               5

(2) INFORMATION FOR SEQ ID NO: 179:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 179:

Arg Ala Leu Ala His Gly Val Arg Val Leu Glu Asp Gly
  1               5                  10

(2) INFORMATION FOR SEQ ID NO: 180:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 180:

Arg Met Ala Trp Asp Met Met
  1               5

(2) INFORMATION FOR SEQ ID NO: 181:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 181:

Ala Ser Arg Cys Trp Val Ala Met
  1               5
```